United States Patent
Arcaro et al.

(10) Patent No.: US 12,059,344 B2
(45) Date of Patent: *Aug. 13, 2024

(54) LEAFLET FRAME ATTACHMENT FOR PROSTHETIC VALVES

(71) Applicant: EDWARDS LIFESCIENCES CORPORATION, Irvine, CA (US)

(72) Inventors: David J. Arcaro, Flagstaff, AZ (US); Stephen M. Probert, Flagstaff, AZ (US); Dustin V. Dienno, Flagstaff, AZ (US); Cody L. Hartman, Flagstaff, AZ (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 291 days.

This patent is subject to a terminal disclaimer.

(21) Appl. No.: 17/183,014

(22) Filed: Feb. 23, 2021

(65) Prior Publication Data

US 2021/0177589 A1    Jun. 17, 2021

Related U.S. Application Data

(63) Continuation of application No. 16/129,651, filed on Sep. 12, 2018, now Pat. No. 10,959,842.

(60) Provisional application No. 62/564,031, filed on Sep. 27, 2017, provisional application No. 62/557,586, filed on Sep. 12, 2017.

(51) Int. Cl.
A61F 2/24    (2006.01)

(52) U.S. Cl.
CPC .......... *A61F 2/2418* (2013.01); *A61F 2/2415* (2013.01); *A61F 2/2433* (2013.01); *A61F 2/2463* (2013.01); *A61F 2/2436* (2013.01); *A61F 2/246* (2013.01); *A61F 2/2466* (2013.01); *A61F 2210/0014* (2013.01); *A61F 2220/0016* (2013.01); *A61F 2220/0025* (2013.01); *A61F 2220/005* (2013.01); *A61F 2220/0075* (2013.01); *A61F 2230/0054* (2013.01);

(Continued)

(58) Field of Classification Search
None
See application file for complete search history.

(56) References Cited

U.S. PATENT DOCUMENTS

| | | | |
|---|---|---|---|
| 654,799 | A | 7/1900 | Levett |
| 3,739,402 | A | 6/1973 | Kahn et al. |

(Continued)

FOREIGN PATENT DOCUMENTS

| | | |
|---|---|---|
| AU | 2013363172 A1 | 7/2015 |
| AU | 2017202405 A1 | 4/2017 |

(Continued)

OTHER PUBLICATIONS

Priority Document for U.S. Appl. No. 61/739,721, received by the International Bureau Jan. 3, 2014, 1 page.

(Continued)

*Primary Examiner* — Megan Y Wolf
(74) *Attorney, Agent, or Firm* — Debra R. Bruce; KLARQUIST SPARKMAN, LLP

(57) ABSTRACT

Described embodiments are directed toward centrally-opening leaflet prosthetic valves having a frame and a leaflet construct. Leaflet frame attachments for prosthetic valves include the leaflet construct being at least partially coupled to a frame outer side by a looped structure.

33 Claims, 23 Drawing Sheets

(52) U.S. Cl.
CPC .............. *A61F 2230/0069* (2013.01); *A61F 2250/0069* (2013.01)

(56) References Cited

U.S. PATENT DOCUMENTS

| | | |
|---|---|---|
| 3,953,566 A | 4/1976 | Gore |
| 4,178,639 A | 12/1979 | Bokros |
| 4,187,390 A | 2/1980 | Gore |
| 4,222,126 A | 9/1980 | Boretos et al. |
| 4,265,694 A | 5/1981 | Boretos et al. |
| 4,332,035 A | 6/1982 | Mano |
| 4,340,091 A | 7/1982 | Skelton et al. |
| 4,477,930 A | 10/1984 | Totten et al. |
| 4,556,996 A | 12/1985 | Wallace |
| 4,626,255 A | 12/1986 | Reichart et al. |
| 4,759,759 A | 7/1988 | Walker et al. |
| 4,851,000 A | 7/1989 | Gupta |
| 4,877,661 A | 10/1989 | House et al. |
| 4,955,899 A | 9/1990 | Della et al. |
| 5,026,513 A | 6/1991 | House et al. |
| 5,064,435 A | 11/1991 | Porter |
| 5,071,609 A | 12/1991 | Tu et al. |
| 5,123,918 A | 6/1992 | Perrier et al. |
| 5,163,955 A | 11/1992 | Love et al. |
| 5,415,667 A | 5/1995 | Frater |
| 5,469,868 A | 11/1995 | Reger |
| 5,476,589 A | 12/1995 | Bacino |
| 5,489,297 A | 2/1996 | Duran |
| 5,534,007 A | 7/1996 | St et al. |
| 5,549,663 A | 8/1996 | Cottone, Jr. |
| 5,554,183 A | 9/1996 | Nazari |
| 5,554,185 A | 9/1996 | Block et al. |
| 5,562,729 A | 10/1996 | Purdy |
| 5,628,791 A | 5/1997 | Bokros et al. |
| 5,673,102 A | 9/1997 | Suzuki et al. |
| 5,708,044 A | 1/1998 | Branca |
| 5,718,973 A | 2/1998 | Lewis et al. |
| 5,749,852 A | 5/1998 | Schwab et al. |
| 5,752,934 A | 5/1998 | Campbell et al. |
| 5,759,192 A | 6/1998 | Saunders |
| 5,769,884 A | 6/1998 | Solovay |
| 5,772,884 A | 6/1998 | Tanaka et al. |
| 5,788,626 A | 8/1998 | Thompson |
| 5,814,405 A | 9/1998 | Branca et al. |
| 5,824,043 A | 10/1998 | Cottone, Jr. |
| 5,843,158 A | 12/1998 | Lenker et al. |
| 5,843,161 A | 12/1998 | Solovay |
| 5,843,171 A | 12/1998 | Campbell et al. |
| 5,853,419 A | 12/1998 | Imran |
| 5,925,061 A | 7/1999 | Ogi et al. |
| 5,928,281 A | 7/1999 | Huynh et al. |
| 5,935,162 A | 8/1999 | Dang |
| 5,935,163 A | 8/1999 | Gabbay |
| 5,944,654 A | 8/1999 | Crawford |
| 5,957,974 A | 9/1999 | Thompson et al. |
| 6,010,529 A | 1/2000 | Herweck et al. |
| 6,013,854 A | 1/2000 | Moriuchi |
| 6,019,785 A | 2/2000 | Strecker |
| 6,042,588 A | 3/2000 | Munsinger et al. |
| 6,042,605 A | 3/2000 | Martin et al. |
| 6,042,606 A | 3/2000 | Frantzen |
| 6,086,612 A | 7/2000 | Jansen |
| 6,110,198 A | 8/2000 | Fogarty et al. |
| 6,117,169 A | 9/2000 | Moe |
| 6,129,758 A | 10/2000 | Love |
| 6,161,399 A | 12/2000 | Jayaraman |
| 6,165,211 A | 12/2000 | Thompson |
| 6,171,335 B1 | 1/2001 | Wheatley et al. |
| 6,174,329 B1 | 1/2001 | Callol et al. |
| 6,174,331 B1 | 1/2001 | Moe et al. |
| 6,190,406 B1 | 2/2001 | Duerig et al. |
| 6,197,143 B1 | 3/2001 | Bodnar |
| 6,217,609 B1 | 4/2001 | Haverkost |
| 6,245,012 B1 | 6/2001 | Kleshinski |
| 6,261,320 B1 | 7/2001 | Tam et al. |
| 6,261,620 B1 | 7/2001 | Leadbeater |
| 6,283,994 B1 | 9/2001 | Moe et al. |
| 6,283,995 B1 | 9/2001 | Moe et al. |
| 6,287,334 B1 | 9/2001 | Moll et al. |
| 6,328,763 B1 | 12/2001 | Love et al. |
| 6,334,873 B1 | 1/2002 | Lane et al. |
| 6,336,937 B1 | 1/2002 | Vonesh et al. |
| 6,352,552 B1 | 3/2002 | Levinson et al. |
| 6,379,382 B1 | 4/2002 | Yang |
| 6,436,132 B1 | 8/2002 | Patel et al. |
| 6,454,798 B1 | 9/2002 | Moe |
| 6,454,799 B1 | 9/2002 | Schreck |
| 6,461,382 B1 | 10/2002 | Cao |
| 6,461,665 B1 | 10/2002 | Scholander |
| 6,482,228 B1 | 11/2002 | Norred |
| 6,488,701 B1 | 12/2002 | Nolting et al. |
| 6,541,589 B1 | 4/2003 | Baillie |
| 6,558,418 B2 | 5/2003 | Carpentier et al. |
| 6,562,069 B2 | 5/2003 | Cai et al. |
| 6,582,464 B2 | 6/2003 | Gabbay |
| 6,613,086 B1 | 9/2003 | Moe et al. |
| 6,620,190 B1 | 9/2003 | Colone |
| 6,626,939 B1 | 9/2003 | Burnside et al. |
| 6,645,244 B2 | 11/2003 | Shu et al. |
| 6,666,885 B2 | 12/2003 | Moe |
| 6,673,102 B1 | 1/2004 | Vonesh et al. |
| 6,673,107 B1 | 1/2004 | Brandt et al. |
| 6,726,715 B2 | 4/2004 | Sutherland |
| 6,730,118 B2 | 5/2004 | Spenser et al. |
| 6,730,120 B2 | 5/2004 | Berg et al. |
| 6,755,856 B2 | 6/2004 | Fierens et al. |
| 6,755,857 B2 | 6/2004 | Peterson et al. |
| 6,758,858 B2 | 7/2004 | McCrea et al. |
| 6,890,350 B1 | 5/2005 | Walak |
| 6,893,460 B2 | 5/2005 | Spenser et al. |
| 6,916,338 B2 | 7/2005 | Speziali |
| 6,936,067 B2 | 8/2005 | Buchanan |
| 6,953,332 B1 | 10/2005 | Kurk et al. |
| 7,022,132 B2 | 4/2006 | Kocur |
| 7,049,380 B1 | 5/2006 | Chang et al. |
| 7,083,642 B2 | 8/2006 | Sirhan et al. |
| 7,105,018 B1 | 9/2006 | Yip et al. |
| 7,137,184 B2 | 11/2006 | Schreck |
| 7,163,556 B2 | 1/2007 | Xie et al. |
| 7,238,200 B2 | 7/2007 | Lee et al. |
| 7,247,167 B2 | 7/2007 | Gabbay |
| 7,306,729 B2 | 12/2007 | Bacino et al. |
| 7,381,218 B2 | 6/2008 | Schreck |
| 7,419,678 B2 | 9/2008 | Falotico |
| 7,462,675 B2 | 12/2008 | Chang et al. |
| 7,510,575 B2 | 3/2009 | Spenser et al. |
| 7,513,909 B2 | 4/2009 | Lane et al. |
| 7,531,611 B2 | 5/2009 | Sabol et al. |
| 7,563,277 B2 | 7/2009 | Case et al. |
| 7,708,775 B2 | 5/2010 | Rowe et al. |
| 7,727,274 B2 | 6/2010 | Zilla et al. |
| 7,758,640 B2 | 7/2010 | Vesely |
| 7,780,725 B2 | 8/2010 | Haug et al. |
| 7,789,908 B2 | 9/2010 | Sowinski et al. |
| 7,803,186 B1 | 9/2010 | Li et al. |
| 7,811,314 B2 | 10/2010 | Fierens et al. |
| 7,815,763 B2 | 10/2010 | Fierens et al. |
| 7,879,085 B2 | 2/2011 | Sowinski et al. |
| 7,887,562 B2 | 2/2011 | Young et al. |
| 7,914,569 B2 | 3/2011 | Nguyen et al. |
| 7,927,364 B2 | 4/2011 | Fierens et al. |
| 7,927,365 B2 | 4/2011 | Fierens et al. |
| 7,935,141 B2 | 5/2011 | Randall et al. |
| 7,967,829 B2 | 6/2011 | Gunderson et al. |
| 7,967,853 B2 | 6/2011 | Eidenschink et al. |
| 7,993,394 B2 | 8/2011 | Hariton et al. |
| 8,048,440 B2 | 11/2011 | Chang et al. |
| 8,062,359 B2 | 11/2011 | Marquez et al. |
| 8,092,523 B2 | 1/2012 | Li et al. |
| 8,167,935 B2 | 5/2012 | McGuckin et al. |
| 8,226,710 B2 | 7/2012 | Nguyen et al. |
| 8,246,678 B2 | 8/2012 | Salahieh et al. |
| 8,252,037 B2 | 8/2012 | Styrc et al. |
| 8,303,647 B2 | 11/2012 | Case |

(56) References Cited

U.S. PATENT DOCUMENTS

| | | |
|---|---|---|
| 8,349,000 B2 | 1/2013 | Schreck |
| 8,409,274 B2 | 4/2013 | Li et al. |
| 8,475,512 B2 | 7/2013 | Hunt |
| 8,545,525 B2 | 10/2013 | Surti et al. |
| 8,568,475 B2 | 10/2013 | Nguyen et al. |
| 8,585,753 B2 | 11/2013 | Scanlon et al. |
| 8,585,757 B2 | 11/2013 | Agathos |
| 8,628,566 B2 | 1/2014 | Eberhardt et al. |
| 8,637,144 B2 | 1/2014 | Ford |
| 8,709,077 B2 | 4/2014 | Schreck |
| 8,722,178 B2 | 5/2014 | Ashmead et al. |
| 8,728,103 B2 | 5/2014 | Surti et al. |
| 8,728,154 B2 | 5/2014 | Alkhatib |
| 8,784,481 B2 | 7/2014 | Alkhatib et al. |
| 8,801,774 B2 | 8/2014 | Silverman |
| 8,808,848 B2 | 8/2014 | Bacino |
| 8,845,709 B2 | 9/2014 | Styrc et al. |
| 8,845,721 B2 | 9/2014 | Braido et al. |
| 8,852,272 B2 | 10/2014 | Gross et al. |
| 8,870,948 B1 | 10/2014 | Erzberger et al. |
| 8,936,634 B2 | 1/2015 | Irwin et al. |
| 8,945,212 B2 | 2/2015 | Bruchman et al. |
| 8,961,599 B2 | 2/2015 | Bruchman et al. |
| 8,992,608 B2 | 3/2015 | Haug et al. |
| 9,039,757 B2 | 5/2015 | McLean et al. |
| 9,101,469 B2 | 8/2015 | Bruchman et al. |
| 9,101,696 B2 | 8/2015 | Leontein et al. |
| 9,107,771 B2 | 8/2015 | Wubbeling et al. |
| 9,125,740 B2 | 9/2015 | Morriss et al. |
| 9,139,669 B2 | 9/2015 | Xu et al. |
| 9,144,492 B2 | 9/2015 | Bruchman et al. |
| 9,168,131 B2 | 10/2015 | Yohanan et al. |
| 9,198,787 B2 | 12/2015 | Kratzberg et al. |
| 9,241,695 B2 | 1/2016 | Peavey et al. |
| 9,259,313 B2 | 2/2016 | Wheatley |
| 9,283,072 B2 | 3/2016 | Bruchman et al. |
| 9,295,552 B2 | 3/2016 | McLean et al. |
| 9,314,355 B2 | 4/2016 | Styrc et al. |
| 9,345,601 B2 | 5/2016 | Jantzen et al. |
| 9,375,308 B2 | 6/2016 | Norris |
| 9,393,110 B2 | 7/2016 | Levi et al. |
| 9,398,952 B2 | 7/2016 | Bruchman et al. |
| 9,399,085 B2 | 7/2016 | Cleek et al. |
| 9,504,565 B2 | 11/2016 | Armstrong |
| 9,554,786 B2 | 1/2017 | Carley et al. |
| 9,554,900 B2 | 1/2017 | Bruchman et al. |
| 9,597,181 B2 | 3/2017 | Christianson et al. |
| 9,629,718 B2 | 4/2017 | Gloss et al. |
| 9,681,948 B2 | 6/2017 | Levi et al. |
| 9,737,398 B2 | 8/2017 | Bruchman et al. |
| 9,737,422 B2 | 8/2017 | Armstrong et al. |
| 9,743,932 B2 | 8/2017 | Amplatz et al. |
| 9,795,496 B2 | 10/2017 | Armstrong et al. |
| 9,801,712 B2 | 10/2017 | Bruchman et al. |
| 9,827,089 B2 | 11/2017 | Bruchman et al. |
| 9,827,094 B2 | 11/2017 | Bennett |
| 9,839,540 B2 | 12/2017 | Armstrong et al. |
| 9,855,141 B2 | 1/2018 | Dienno et al. |
| 9,931,193 B2 | 4/2018 | Cully et al. |
| 9,931,204 B2 | 4/2018 | Rothstein et al. |
| 9,937,037 B2 | 4/2018 | Dienno et al. |
| 9,968,443 B2 | 5/2018 | Bruchman et al. |
| 10,039,638 B2 | 8/2018 | Bruchman et al. |
| 10,166,128 B2 | 1/2019 | Armstrong et al. |
| 10,279,084 B2 | 5/2019 | Goepfrich et al. |
| 10,285,808 B2 | 5/2019 | Bruchman et al. |
| 10,314,697 B2 | 6/2019 | Gassler |
| 10,321,986 B2 | 6/2019 | Bruchman et al. |
| 10,335,298 B2 | 7/2019 | Armstrong et al. |
| 10,342,659 B2 | 7/2019 | Bennett |
| 10,368,984 B2 | 8/2019 | Armstrong |
| 10,376,360 B2 | 8/2019 | Bruchman et al. |
| 10,441,416 B2 | 10/2019 | Oba et al. |
| 10,463,478 B2 | 11/2019 | Bruchman et al. |
| 10,507,124 B2 | 12/2019 | Armstrong et al. |
| 10,639,144 B2 | 5/2020 | Bruchman et al. |
| 10,660,745 B2 | 5/2020 | Bruchman et al. |
| 10,881,507 B2 | 1/2021 | Bruchman et al. |
| 10,959,842 B2 * | 3/2021 | Arcaro .................. A61F 2/2463 |
| 10,980,633 B2 | 4/2021 | Dienno et al. |
| 11,020,221 B2 | 6/2021 | Arcaro et al. |
| 11,039,917 B2 | 6/2021 | Bruchman et al. |
| D926,322 S | 7/2021 | Bennett et al. |
| 11,065,112 B2 | 7/2021 | Gassler |
| 11,090,153 B2 | 8/2021 | Haarer et al. |
| 11,109,963 B2 | 9/2021 | Dienno et al. |
| 11,123,183 B2 | 9/2021 | Bennett et al. |
| 11,439,502 B2 | 9/2022 | Busalacchi et al. |
| 11,471,276 B2 | 10/2022 | Bennett |
| 2001/0053929 A1 | 12/2001 | Vonesh et al. |
| 2002/0045936 A1 | 4/2002 | Moe |
| 2002/0055773 A1 | 5/2002 | Campbell et al. |
| 2002/0076542 A1 | 6/2002 | Kramer et al. |
| 2002/0082687 A1 | 6/2002 | Moe |
| 2002/0133226 A1 | 9/2002 | Marquez et al. |
| 2002/0151953 A1 | 10/2002 | Chobotov et al. |
| 2002/0151956 A1 | 10/2002 | Chobotov et al. |
| 2002/0183840 A1 | 12/2002 | Lapeyre et al. |
| 2002/0198588 A1 | 12/2002 | Armstrong et al. |
| 2002/0198594 A1 | 12/2002 | Schreck |
| 2003/0014105 A1 | 1/2003 | Cao |
| 2003/0027332 A1 | 2/2003 | Hugues et al. |
| 2003/0055494 A1 | 3/2003 | Bezuidenhout et al. |
| 2003/0055496 A1 | 3/2003 | Cai et al. |
| 2003/0060871 A1 | 3/2003 | Hill et al. |
| 2003/0074052 A1 | 4/2003 | Besselink et al. |
| 2003/0097175 A1 | 5/2003 | O'Connor et al. |
| 2003/0114913 A1 | 6/2003 | Spenser et al. |
| 2003/0125805 A1 | 7/2003 | Johnson et al. |
| 2003/0180488 A1 | 9/2003 | Lim et al. |
| 2003/0209835 A1 | 11/2003 | Chun et al. |
| 2003/0229394 A1 | 12/2003 | Ogle et al. |
| 2004/0024442 A1 | 2/2004 | Sowinski et al. |
| 2004/0024448 A1 | 2/2004 | Chang et al. |
| 2004/0024451 A1 | 2/2004 | Johnson et al. |
| 2004/0026245 A1 | 2/2004 | Agarwal et al. |
| 2004/0039436 A1 | 2/2004 | Spenser et al. |
| 2004/0044400 A1 | 3/2004 | Cheng et al. |
| 2004/0044401 A1 | 3/2004 | Bales et al. |
| 2004/0133266 A1 | 7/2004 | Clerc et al. |
| 2004/0170782 A1 | 9/2004 | Wang et al. |
| 2004/0176839 A1 | 9/2004 | Huynh et al. |
| 2004/0224442 A1 | 11/2004 | Grigg |
| 2004/0243222 A1 | 12/2004 | Osborne et al. |
| 2004/0260277 A1 | 12/2004 | Maguire |
| 2004/0260389 A1 | 12/2004 | Case et al. |
| 2004/0260393 A1 | 12/2004 | Rahdert et al. |
| 2005/0027348 A1 | 2/2005 | Case et al. |
| 2005/0080476 A1 | 4/2005 | Gunderson et al. |
| 2005/0119722 A1 | 6/2005 | Styrc et al. |
| 2005/0137680 A1 | 6/2005 | Ortiz et al. |
| 2005/0137682 A1 | 6/2005 | Justino |
| 2005/0203614 A1 | 9/2005 | Forster et al. |
| 2005/0261765 A1 | 11/2005 | Liddicoat |
| 2005/0283224 A1 | 12/2005 | King |
| 2006/0008497 A1 | 1/2006 | Gabbay |
| 2006/0009835 A1 | 1/2006 | Osborne et al. |
| 2006/0015171 A1 | 1/2006 | Armstrong |
| 2006/0036311 A1 | 2/2006 | Nakayama et al. |
| 2006/0041091 A1 | 2/2006 | Chang et al. |
| 2006/0106337 A1 | 5/2006 | Blankenship |
| 2006/0118236 A1 | 6/2006 | House et al. |
| 2006/0122693 A1 | 6/2006 | Biadillah et al. |
| 2006/0135985 A1 | 6/2006 | Cox et al. |
| 2006/0154365 A1 | 7/2006 | Ratcliffe et al. |
| 2006/0161241 A1 | 7/2006 | Barbut et al. |
| 2006/0190070 A1 | 8/2006 | Dieck et al. |
| 2006/0229718 A1 | 10/2006 | Marquez |
| 2006/0229719 A1 | 10/2006 | Marquez et al. |
| 2006/0259133 A1 | 11/2006 | Sowinski et al. |
| 2006/0259136 A1 | 11/2006 | Nguyen et al. |
| 2006/0265053 A1 | 11/2006 | Hunt |
| 2006/0271091 A1 | 11/2006 | Campbell et al. |
| 2006/0276813 A1 | 12/2006 | Greenberg |

(56) References Cited

U.S. PATENT DOCUMENTS

| | | |
|---|---|---|
| 2006/0276883 A1 | 12/2006 | Greenberg et al. |
| 2006/0276888 A1 | 12/2006 | Lee et al. |
| 2006/0282162 A1 | 12/2006 | Nguyen et al. |
| 2006/0287719 A1 | 12/2006 | Rowe et al. |
| 2006/0290027 A1 | 12/2006 | O'Connor et al. |
| 2007/0010876 A1 | 1/2007 | Salahieh et al. |
| 2007/0012624 A1 | 1/2007 | Bacino et al. |
| 2007/0021826 A1 | 1/2007 | Case et al. |
| 2007/0060999 A1 | 3/2007 | Randall et al. |
| 2007/0100435 A1 | 5/2007 | Case et al. |
| 2007/0118210 A1 | 5/2007 | Pinchuk |
| 2007/0129786 A1 | 6/2007 | Beach et al. |
| 2007/0207186 A1 | 9/2007 | Scanlon et al. |
| 2007/0207816 A1 | 9/2007 | Spain, Jr. |
| 2007/0208417 A1 | 9/2007 | Agnew |
| 2007/0208421 A1 | 9/2007 | Quigley |
| 2007/0213800 A1 | 9/2007 | Fierens et al. |
| 2007/0244552 A1 | 10/2007 | Salahieh et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0009940 A1 | 1/2008 | Cribier |
| 2008/0026190 A1 | 1/2008 | King et al. |
| 2008/0039934 A1 | 2/2008 | Styrc |
| 2008/0051876 A1 | 2/2008 | Ta et al. |
| 2008/0065198 A1 | 3/2008 | Quintessenza |
| 2008/0071369 A1 | 3/2008 | Tuval et al. |
| 2008/0082154 A1 | 4/2008 | Tseng et al. |
| 2008/0097301 A1 | 4/2008 | Alpini et al. |
| 2008/0097401 A1 | 4/2008 | Trapp et al. |
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0133004 A1 | 6/2008 | White |
| 2008/0140178 A1 | 6/2008 | Rasmussen et al. |
| 2008/0195199 A1 | 8/2008 | Kheradvar et al. |
| 2008/0208327 A1 | 8/2008 | Rowe |
| 2008/0220041 A1 | 9/2008 | Brito et al. |
| 2008/0228263 A1 | 9/2008 | Ryan |
| 2008/0300678 A1 | 12/2008 | Eidenschink et al. |
| 2008/0319531 A1 | 12/2008 | Doran et al. |
| 2009/0005854 A1 | 1/2009 | Huang et al. |
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0099640 A1 | 4/2009 | Weng |
| 2009/0104247 A1 | 4/2009 | Pacetti |
| 2009/0117334 A1 | 5/2009 | Sogard et al. |
| 2009/0138079 A1 | 5/2009 | Tuval et al. |
| 2009/0157175 A1 | 6/2009 | Benichou |
| 2009/0182413 A1 | 7/2009 | Burkart et al. |
| 2009/0240320 A1 | 9/2009 | Tuval et al. |
| 2009/0264997 A1 | 10/2009 | Salahieh et al. |
| 2009/0276039 A1 | 11/2009 | Meretei |
| 2009/0281609 A1 | 11/2009 | Benichou et al. |
| 2009/0287305 A1 | 11/2009 | Amalaha |
| 2009/0292350 A1 | 11/2009 | Eberhardt et al. |
| 2009/0306762 A1 | 12/2009 | McCullagh et al. |
| 2009/0306766 A1 | 12/2009 | McDermott et al. |
| 2010/0016940 A1 | 1/2010 | Shokoohi et al. |
| 2010/0023114 A1 | 1/2010 | Chambers et al. |
| 2010/0036021 A1 | 2/2010 | Lee et al. |
| 2010/0036484 A1 | 2/2010 | Hariton et al. |
| 2010/0049294 A1 | 2/2010 | Zukowski et al. |
| 2010/0082089 A1 | 4/2010 | Quadri et al. |
| 2010/0082094 A1 | 4/2010 | Quadri et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0114307 A1 | 5/2010 | Agnew et al. |
| 2010/0131056 A1 | 5/2010 | Lapeyre |
| 2010/0137998 A1 | 6/2010 | Sobrino-Serrano et al. |
| 2010/0145438 A1 | 6/2010 | Barone |
| 2010/0159171 A1 | 6/2010 | Clough |
| 2010/0168839 A1 | 7/2010 | Braido et al. |
| 2010/0185274 A1 | 7/2010 | Moaddeb et al. |
| 2010/0185277 A1 | 7/2010 | Braido et al. |
| 2010/0191320 A1 | 7/2010 | Straubinger et al. |
| 2010/0204781 A1 | 8/2010 | Alkhatib |
| 2010/0204785 A1 | 8/2010 | Alkhatib |
| 2010/0211165 A1 | 8/2010 | Schreck |
| 2010/0217382 A1 | 8/2010 | Chau et al. |
| 2010/0248324 A1 | 9/2010 | Xu et al. |
| 2010/0249923 A1 | 9/2010 | Alkhatib et al. |
| 2010/0256738 A1 | 10/2010 | Berglund |
| 2010/0262231 A1 | 10/2010 | Tuval et al. |
| 2010/0286760 A1 | 11/2010 | Beach et al. |
| 2010/0298931 A1 | 11/2010 | Quadri et al. |
| 2010/0305682 A1 | 12/2010 | Furst |
| 2011/0009953 A1 | 1/2011 | Luk et al. |
| 2011/0040366 A1 | 2/2011 | Goetz et al. |
| 2011/0054515 A1 | 3/2011 | Bridgeman et al. |
| 2011/0064781 A1 | 3/2011 | Cleek et al. |
| 2011/0087318 A1 | 4/2011 | Daugherty et al. |
| 2011/0160836 A1 | 6/2011 | Behan |
| 2011/0172784 A1 | 7/2011 | Richter et al. |
| 2011/0208283 A1 | 8/2011 | Rust |
| 2011/0218619 A1 | 9/2011 | Benichou et al. |
| 2011/0251678 A1 | 10/2011 | Eidenschink et al. |
| 2011/0257739 A1 | 10/2011 | Corbett |
| 2011/0282439 A1 | 11/2011 | Thill et al. |
| 2011/0295363 A1 | 12/2011 | Girard et al. |
| 2012/0035722 A1 | 2/2012 | Tuval |
| 2012/0078357 A1 | 3/2012 | Conklin |
| 2012/0083839 A1 | 4/2012 | Letac et al. |
| 2012/0089223 A1 | 4/2012 | Nguyen et al. |
| 2012/0101567 A1 | 4/2012 | Jansen |
| 2012/0101571 A1 | 4/2012 | Thambar et al. |
| 2012/0116496 A1 | 5/2012 | Chuter et al. |
| 2012/0116498 A1 | 5/2012 | Chuter et al. |
| 2012/0123529 A1 | 5/2012 | Levi et al. |
| 2012/0123530 A1 | 5/2012 | Carpentier et al. |
| 2012/0130468 A1 | 5/2012 | Khosravi et al. |
| 2012/0130471 A1 | 5/2012 | Shoemaker et al. |
| 2012/0185038 A1 | 7/2012 | Fish et al. |
| 2012/0215303 A1 | 8/2012 | Quadri et al. |
| 2012/0253453 A1 | 10/2012 | Bruchman et al. |
| 2012/0277734 A1 | 11/2012 | Goetz et al. |
| 2012/0290082 A1 | 11/2012 | Quint et al. |
| 2012/0323211 A1 | 12/2012 | Ogle et al. |
| 2012/0323315 A1 | 12/2012 | Bruchman et al. |
| 2013/0018456 A1 | 1/2013 | Li et al. |
| 2013/0018458 A1 | 1/2013 | Yohanan et al. |
| 2013/0079700 A1 | 3/2013 | Ballard et al. |
| 2013/0110229 A1 | 5/2013 | Bokeriya et al. |
| 2013/0116655 A1 | 5/2013 | Bacino et al. |
| 2013/0131780 A1 | 5/2013 | Armstrong et al. |
| 2013/0150956 A1 | 6/2013 | Yohanan et al. |
| 2013/0158647 A1 | 6/2013 | Norris et al. |
| 2013/0166021 A1 | 6/2013 | Bruchman et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |
| 2013/0204360 A1 | 8/2013 | Gainor |
| 2013/0253466 A1 | 9/2013 | Campbell et al. |
| 2013/0297003 A1 | 11/2013 | Pinchuk |
| 2013/0338755 A1 | 12/2013 | Goetz et al. |
| 2014/0005771 A1 | 1/2014 | Braido et al. |
| 2014/0005773 A1 | 1/2014 | Wheatley |
| 2014/0031924 A1 | 1/2014 | Bruchman et al. |
| 2014/0031927 A1 | 1/2014 | Bruchman et al. |
| 2014/0094898 A1 | 4/2014 | Borck |
| 2014/0106951 A1 | 4/2014 | Brandon |
| 2014/0135897 A1 | 5/2014 | Cully et al. |
| 2014/0163671 A1 | 6/2014 | Bruchman et al. |
| 2014/0163673 A1 | 6/2014 | Bruchman et al. |
| 2014/0172066 A1 | 6/2014 | Goepfrich et al. |
| 2014/0172069 A1 | 6/2014 | Roeder et al. |
| 2014/0172077 A1 | 6/2014 | Bruchman et al. |
| 2014/0172078 A1 | 6/2014 | Bruchman et al. |
| 2014/0172079 A1 | 6/2014 | Bruchman et al. |
| 2014/0172082 A1 | 6/2014 | Bruchman et al. |
| 2014/0172083 A1 | 6/2014 | Bruchman et al. |

(56) References Cited

U.S. PATENT DOCUMENTS

| | | |
|---|---|---|
| 2014/0180400 A1 | 6/2014 | Bruchman et al. |
| 2014/0180402 A1 | 6/2014 | Bruchman et al. |
| 2014/0194968 A1 | 7/2014 | Zukowski |
| 2014/0222140 A1 | 8/2014 | Schreck |
| 2014/0236289 A1 | 8/2014 | Alkhatib |
| 2014/0277413 A1 | 9/2014 | Arnold et al. |
| 2014/0277418 A1 | 9/2014 | Miller |
| 2014/0296969 A1 | 10/2014 | Tegels et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0343670 A1 | 11/2014 | Bakis et al. |
| 2015/0005870 A1 | 1/2015 | Kovach et al. |
| 2015/0018944 A1 | 1/2015 | O'Connell et al. |
| 2015/0088250 A1 | 3/2015 | Zeng et al. |
| 2015/0105856 A1 | 4/2015 | Rowe et al. |
| 2015/0142100 A1 | 5/2015 | Morriss et al. |
| 2015/0157456 A1 | 6/2015 | Armstrong |
| 2015/0157770 A1 | 6/2015 | Cully et al. |
| 2015/0224231 A1 | 8/2015 | Bruchman et al. |
| 2015/0245910 A1 | 9/2015 | Righini et al. |
| 2015/0313871 A1 | 11/2015 | Li et al. |
| 2015/0366663 A1 | 12/2015 | Bruchman et al. |
| 2015/0366664 A1 | 12/2015 | Guttenberg et al. |
| 2016/0001469 A1 | 1/2016 | Bacchereti et al. |
| 2016/0015422 A1 | 1/2016 | De et al. |
| 2016/0074161 A1 | 3/2016 | Bennett |
| 2016/0106537 A1 | 4/2016 | Christianson et al. |
| 2016/0113699 A1 | 4/2016 | Sverdlik et al. |
| 2016/0157998 A1 | 6/2016 | Bruchman et al. |
| 2016/0175095 A1 | 6/2016 | Dienno et al. |
| 2016/0175096 A1 | 6/2016 | Dienno et al. |
| 2016/0206424 A1 | 7/2016 | Al-Jilaihawi et al. |
| 2016/0213465 A1 | 7/2016 | Girard et al. |
| 2016/0235525 A1 | 8/2016 | Rothstein et al. |
| 2016/0250051 A1 | 9/2016 | Im et al. |
| 2016/0310268 A1 | 10/2016 | Oba et al. |
| 2016/0317299 A1 | 11/2016 | Alkhatib |
| 2017/0027727 A1 | 2/2017 | Wuebbeling et al. |
| 2017/0042674 A1 | 2/2017 | Armstrong |
| 2017/0056169 A1 | 3/2017 | Johnson et al. |
| 2017/0065400 A1 | 3/2017 | Armstrong et al. |
| 2017/0095330 A1 | 4/2017 | Malewicz et al. |
| 2017/0095331 A1 | 4/2017 | Spenser et al. |
| 2017/0100236 A1 | 4/2017 | Robertson et al. |
| 2017/0105854 A1 | 4/2017 | Treacy et al. |
| 2017/0106176 A1 | 4/2017 | Taft et al. |
| 2017/0128199 A1 | 5/2017 | Gurovich et al. |
| 2017/0156859 A1 | 6/2017 | Chang et al. |
| 2017/0165066 A1 | 6/2017 | Rothstein |
| 2017/0165067 A1 | 6/2017 | Barajas-Torres et al. |
| 2017/0216062 A1 | 8/2017 | Armstrong et al. |
| 2017/0224481 A1 | 8/2017 | Spenser et al. |
| 2017/0252153 A1 | 9/2017 | Chau et al. |
| 2017/0348101 A1 | 12/2017 | Vaughn et al. |
| 2018/0021128 A1 | 1/2018 | Bruchman et al. |
| 2018/0021129 A1 | 1/2018 | Peterson et al. |
| 2018/0125646 A1 | 5/2018 | Bruchman et al. |
| 2018/0177583 A1 | 6/2018 | Cully et al. |
| 2018/0221144 A1 | 8/2018 | Bruchman et al. |
| 2018/0271651 A1 | 9/2018 | Christianson et al. |
| 2018/0271653 A1 | 9/2018 | Vidlund et al. |
| 2018/0318070 A1 | 11/2018 | Bruchman et al. |
| 2019/0076245 A1 | 3/2019 | Arcaro et al. |
| 2019/0091014 A1 | 3/2019 | Arcaro et al. |
| 2019/0091015 A1 | 3/2019 | Dienno et al. |
| 2019/0110893 A1 | 4/2019 | Haarer et al. |
| 2019/0125517 A1 | 5/2019 | Cully et al. |
| 2019/0125528 A1 | 5/2019 | Busalacchi et al. |
| 2019/0125530 A1 | 5/2019 | Arcaro et al. |
| 2019/0125531 A1 | 5/2019 | Bennett et al. |
| 2019/0125534 A1 | 5/2019 | Arcaro et al. |
| 2019/0209292 A1 | 7/2019 | Bruchman et al. |
| 2019/0209739 A1 | 7/2019 | Goepfrich et al. |
| 2019/0216592 A1 | 7/2019 | Cully et al. |
| 2019/0247185 A1 | 8/2019 | Gassler |
| 2019/0254815 A1 | 8/2019 | Bruchman et al. |
| 2019/0269505 A1 | 9/2019 | Bruchman et al. |
| 2019/0314154 A1 | 10/2019 | Armstrong |
| 2019/0328525 A1 | 10/2019 | Noe et al. |
| 2019/0374339 A1 | 12/2019 | Bennett |
| 2020/0000578 A1 | 1/2020 | Bruchman et al. |
| 2020/0022828 A1 | 1/2020 | Armstrong et al. |
| 2020/0179663 A1 | 6/2020 | Mcdaniel et al. |
| 2020/0237497 A1 | 7/2020 | Silverman et al. |
| 2020/0237505 A1 | 7/2020 | Bruchman et al. |
| 2020/0246137 A1 | 8/2020 | Bruchman et al. |
| 2020/0276014 A1 | 9/2020 | Burkart et al. |
| 2020/0323631 A1 | 10/2020 | Chuter et al. |
| 2021/0121289 A1 | 4/2021 | Bruchman et al. |
| 2021/0205074 A1 | 7/2021 | Bruchman et al. |
| 2021/0307905 A1 | 10/2021 | Arcaro et al. |
| 2021/0338422 A1 | 11/2021 | Dienno et al. |
| 2021/0346156 A1 | 11/2021 | Haarer et al. |
| 2021/0361420 A1 | 11/2021 | Bennett et al. |
| 2021/0393399 A1 | 12/2021 | Arcaro et al. |
| 2022/0000611 A1 | 1/2022 | Arcaro et al. |
| 2022/0023032 A1 | 1/2022 | Bruchman et al. |
| 2022/0183831 A1 | 6/2022 | Burkart et al. |
| 2022/0257369 A1 | 8/2022 | Burkart et al. |
| 2022/0273426 A1 | 9/2022 | Hagaman et al. |
| 2022/0378575 A1 | 12/2022 | Busalacchi et al. |
| 2023/0000623 A1 | 1/2023 | Bennett |

FOREIGN PATENT DOCUMENTS

| | | |
|---|---|---|
| CA | 2297536 A1 | 12/2000 |
| CA | 2462509 A1 | 4/2003 |
| CA | 2849030 A1 | 4/2013 |
| CA | 2878691 A1 | 1/2014 |
| CA | 2964546 A1 | 1/2014 |
| CA | 2960034 A1 | 3/2016 |
| CN | 101057796 A | 10/2007 |
| CN | 101091675 A | 12/2007 |
| CN | 101188985 A | 5/2008 |
| CN | 101374477 A | 2/2009 |
| CN | 101420913 A | 4/2009 |
| CN | 101849863 A | 10/2010 |
| CN | 101902989 A | 12/2010 |
| CN | 101926699 A | 12/2010 |
| CN | 201744060 U | 2/2011 |
| CN | 102015009 A | 4/2011 |
| CN | 102119013 A | 7/2011 |
| CN | 102292053 A | 12/2011 |
| CN | 102438546 A | 5/2012 |
| CN | 102573703 A | 7/2012 |
| CN | 102652694 A | 9/2012 |
| CN | 102764169 A | 11/2012 |
| CN | 102791223 A | 11/2012 |
| CN | 102883684 A | 1/2013 |
| CN | 103079498 A | 5/2013 |
| CN | 103228232 A | 7/2013 |
| CN | 103237524 A | 8/2013 |
| CN | 103384505 A | 11/2013 |
| CN | 103732183 A | 4/2014 |
| CN | 103781439 A | 5/2014 |
| CN | 103945796 A | 7/2014 |
| CN | 104114127 A | 10/2014 |
| CN | 104487023 A | 4/2015 |
| CN | 104507417 A | 4/2015 |
| CN | 104869948 A | 8/2015 |
| CN | 105101911 A | 11/2015 |
| CN | 105263445 A | 1/2016 |
| CN | 105662651 A | 6/2016 |
| CN | 105792780 A | 7/2016 |
| CN | 106668949 A | 5/2017 |
| CN | 106714733 A | 5/2017 |
| CN | 106794065 A | 5/2017 |
| CN | 107106294 A | 8/2017 |
| CN | 107690323 A | 2/2018 |
| CN | 108578016 A | 9/2018 |
| DE | 212013000104 U1 | 11/2014 |
| EP | 0293090 A2 | 11/1988 |
| EP | 0313263 A2 | 4/1989 |

(56) References Cited

FOREIGN PATENT DOCUMENTS

| | | |
|---|---|---|
| EP | 0582870 A2 | 2/1994 |
| EP | 0775472 A2 | 5/1997 |
| EP | 0815806 A2 | 1/1998 |
| EP | 0893108 A2 | 1/1999 |
| EP | 1057460 A1 | 12/2000 |
| EP | 1318775 A1 | 6/2003 |
| EP | 1666003 A1 | 6/2006 |
| EP | 1395205 B1 | 7/2008 |
| EP | 1235537 B1 | 12/2008 |
| EP | 2193762 A1 | 6/2010 |
| EP | 2255750 A2 | 12/2010 |
| EP | 2400923 A1 | 1/2012 |
| EP | 2489331 A2 | 8/2012 |
| EP | 2359774 B1 | 1/2013 |
| EP | 2591100 A2 | 5/2013 |
| EP | 2109417 B1 | 11/2013 |
| EP | 3142608 A1 | 3/2017 |
| EP | 3797738 A1 | 3/2021 |
| FR | 2591100 A1 | 6/1987 |
| GB | 2312485 A | 10/1997 |
| GB | 2513194 A | 10/2014 |
| IN | 102724937 A | 10/2012 |
| IN | 105007955 A | 10/2015 |
| JP | 44-032400 | 12/1969 |
| JP | 1969-032400 B | 12/1969 |
| JP | 02-000645 A | 1/1990 |
| JP | 09-241412 A | 9/1997 |
| JP | 10-507097 A | 7/1998 |
| JP | 11-290448 A | 10/1999 |
| JP | 11-512635 A | 11/1999 |
| JP | 2000-511459 A | 9/2000 |
| JP | 2000-513248 A | 10/2000 |
| JP | 2001-000460 A | 1/2001 |
| JP | 2001-508681 A | 7/2001 |
| JP | 2001-509702 A | 7/2001 |
| JP | 2001-511030 A | 8/2001 |
| JP | 2002-525169 A | 8/2002 |
| JP | 2002-541915 A | 12/2002 |
| JP | 2004-510471 A | 4/2004 |
| JP | 2005-500101 A | 1/2005 |
| JP | 2005-512611 A | 5/2005 |
| JP | 2005-514108 A | 5/2005 |
| JP | 2007-525291 A | 9/2007 |
| JP | 2007-526098 A | 9/2007 |
| JP | 2007-536989 A | 12/2007 |
| JP | 2008-506459 A | 3/2008 |
| JP | 2008-535572 A | 9/2008 |
| JP | 4335487 B2 | 9/2009 |
| JP | 2010-500107 A | 1/2010 |
| JP | 2010-504174 A | 2/2010 |
| JP | 2010-517623 A | 5/2010 |
| JP | 2010-528761 A | 8/2010 |
| JP | 2010-188189 A | 9/2010 |
| JP | 2010-535075 A | 11/2010 |
| JP | 2010-536527 A | 12/2010 |
| JP | 2012-504031 A | 2/2012 |
| JP | 2012-152563 A | 8/2012 |
| JP | 2013-506439 A | 2/2013 |
| JP | 2013-543399 A | 12/2013 |
| JP | 2014-513585 A | 6/2014 |
| JP | 2014-517720 A | 7/2014 |
| JP | 2015-523168 A | 8/2015 |
| JP | 2016-501104 A | 1/2016 |
| JP | 2016-501115 A | 1/2016 |
| JP | 2016-509932 A | 4/2016 |
| JP | 2016-510645 A | 4/2016 |
| JP | 2016-512753 A | 5/2016 |
| JP | 2016-518948 A | 6/2016 |
| JP | 2017-527397 A | 9/2017 |
| JP | 2018-079352 A | 5/2018 |
| JP | 6392778 B2 | 9/2018 |
| JP | 6802300 B2 | 12/2020 |
| NO | 95/05555 A1 | 2/1995 |
| RU | 2124986 C1 | 1/1999 |
| RU | 2434604 C1 | 11/2011 |
| WO | 94/13224 A1 | 6/1994 |
| WO | 94/16802 A1 | 8/1994 |
| WO | 95/09586 A1 | 4/1995 |
| WO | 96/02212 A1 | 2/1996 |
| WO | 96/07370 A1 | 3/1996 |
| WO | 96/40348 A1 | 12/1996 |
| WO | 97/10871 A1 | 3/1997 |
| WO | 99/26558 A1 | 6/1999 |
| WO | 00/18333 A1 | 4/2000 |
| WO | 00/41649 A1 | 7/2000 |
| WO | 00/47271 A1 | 8/2000 |
| WO | 00/62716 A1 | 10/2000 |
| WO | 01/28453 A2 | 4/2001 |
| WO | 01/41679 A1 | 6/2001 |
| WO | 01/64278 A1 | 9/2001 |
| WO | 01/74272 A2 | 10/2001 |
| WO | 02/07795 A2 | 1/2002 |
| WO | 02/24118 A1 | 3/2002 |
| WO | 02/24119 A1 | 3/2002 |
| WO | 02/45933 A2 | 6/2002 |
| WO | 02/47468 A1 | 6/2002 |
| WO | 02/60506 A1 | 8/2002 |
| WO | 2002/100301 A1 | 12/2002 |
| WO | 03/03946 A1 | 1/2003 |
| WO | 03/07795 A1 | 1/2003 |
| WO | 03/47468 A1 | 6/2003 |
| WO | 03/90834 A2 | 11/2003 |
| WO | 2004/000375 A1 | 12/2003 |
| WO | 2005/084595 A1 | 9/2005 |
| WO | 2005/112827 A1 | 12/2005 |
| WO | 2006/019626 A2 | 2/2006 |
| WO | 2006/058322 A2 | 6/2006 |
| WO | 2006/108090 A2 | 10/2006 |
| WO | 2007/016251 A2 | 2/2007 |
| WO | 2008/021002 A1 | 2/2008 |
| WO | 2008/028964 A2 | 3/2008 |
| WO | 2008/036870 A2 | 3/2008 |
| WO | 2008/049045 A2 | 4/2008 |
| WO | 2008/052421 A1 | 5/2008 |
| WO | 2008/091589 A1 | 7/2008 |
| WO | 2008/021006 A3 | 8/2008 |
| WO | 2008/097589 A1 | 8/2008 |
| WO | 2008/097592 A2 | 8/2008 |
| WO | 2008/150529 A1 | 12/2008 |
| WO | 2009/017827 A1 | 2/2009 |
| WO | 2009/029199 A1 | 3/2009 |
| WO | 2009/045332 A2 | 4/2009 |
| WO | 2009/100210 A1 | 8/2009 |
| WO | 2009/108355 A1 | 9/2009 |
| WO | 2010/006783 A1 | 1/2010 |
| WO | 2010/008570 A1 | 1/2010 |
| WO | 2010/030766 A1 | 3/2010 |
| WO | 2010/037141 A1 | 4/2010 |
| WO | 2010/057262 A1 | 5/2010 |
| WO | 2010/086460 A1 | 8/2010 |
| WO | 2010/132707 A1 | 11/2010 |
| WO | 2010/150208 A2 | 12/2010 |
| WO | 2011/098565 A1 | 8/2011 |
| WO | 2011/109450 A2 | 9/2011 |
| WO | 2011/109801 A2 | 9/2011 |
| WO | 2011/112706 A2 | 9/2011 |
| WO | 2012/004460 A2 | 1/2012 |
| WO | 2012/011261 A1 | 1/2012 |
| WO | 2012/040643 A2 | 3/2012 |
| WO | 2012/047644 A2 | 4/2012 |
| WO | 2012/065080 A2 | 5/2012 |
| WO | 2012/082952 A2 | 6/2012 |
| WO | 2012/099979 A1 | 7/2012 |
| WO | 2012/110767 A2 | 8/2012 |
| WO | 2012/116368 A2 | 8/2012 |
| WO | 2012/135603 A2 | 10/2012 |
| WO | 2012/158944 A1 | 11/2012 |
| WO | 2012/167131 A1 | 12/2012 |
| WO | 2013/074663 A2 | 5/2013 |
| WO | 2013/074990 A1 | 5/2013 |
| WO | 2013/096854 A2 | 6/2013 |
| WO | 2013/109337 A1 | 7/2013 |
| WO | 2014/018189 A2 | 1/2014 |
| WO | 2014/018432 A2 | 1/2014 |

(56) References Cited

FOREIGN PATENT DOCUMENTS

| | | |
|---|---|---|
| WO | 2014/099150 A1 | 6/2014 |
| WO | 2014/099163 A1 | 6/2014 |
| WO | 2014/099722 A1 | 6/2014 |
| WO | 2014/144937 A2 | 9/2014 |
| WO | 2014/149319 A1 | 9/2014 |
| WO | 2014/181188 A2 | 11/2014 |
| WO | 2015/045002 A1 | 4/2015 |
| WO | 2015/085138 A1 | 6/2015 |
| WO | 2015/171743 A2 | 11/2015 |
| WO | 2015/173794 A1 | 11/2015 |
| WO | 2016/028591 A1 | 2/2016 |
| WO | 2016/044223 A1 | 3/2016 |
| WO | 2016/100913 A1 | 6/2016 |
| WO | 2016/172349 A1 | 10/2016 |
| WO | 2016/186909 A1 | 11/2016 |
| WO | 2017/038145 A1 | 3/2017 |
| WO | 2017/096157 A1 | 6/2017 |
| WO | 2019/067219 A1 | 4/2019 |
| WO | 2019/067220 A1 | 4/2019 |
| WO | 2019/074607 A1 | 4/2019 |
| WO | 2019/074869 A1 | 4/2019 |
| WO | 2019/089138 A1 | 5/2019 |
| WO | 2019/246268 A1 | 12/2019 |

OTHER PUBLICATIONS

Application Data Sheet, Drawings, Specification, Claims, and Abstract filed under U.S. Appl. No. 13/843,196 on Mar. 15, 2013, 52 pages.
Clough, Norman E. Introducing a New Family of GORE ePTFE Fibers (2007), pp. 1-10.
English translation of RU2434604 (C1), filed Apr. 30, 2010, translation powered by EPO and Google, 8 pages.
International Search Report and Written Opinion issued in PCT/US2018/050764, mailed Nov. 23, 2018, 13 pages.
Mano Thubrikar, "The Aortic Valve", Chapter 1: Geometry of the Aortic Valve, CRC Press, Inc., Informa Healthcare, 2011, 40 pages.
Norman E. Clough. Introducing a New Family of GORE (Trademark) ePTFE Fibers (2007).
Opposition from EP16196687.4, mailed on Dec. 12, 2019, 38 pages.
Opposition from EP17187595.8, filed Sep. 12, 2019, 50 pages.
Google Image Search Results, "S-Shaped", accessed Nov. 1, 2013.
International Preliminary Report on Patentability received for PCT Patent Application No. PCT/US15/50113, mailed on Mar. 30, 2017, 9 pages.
International Preliminary Report on Patentability received for PCT Patent Application No. PCT/US2018/050764, mailed on Mar. 26, 2020, 9 pages.
International Preliminary Report on Patentability received for PCT Patent Application No. PCT/US2020/027921, mailed on Oct. 21, 2021, 11 pages.
International Search Report and Written Opinion from PCT/US2018/050766, dated Mar. 11, 2019, 16 pages.
International Search Report and Written Opinion issued in PCT/US2018/050778, mailed Nov. 29, 2018, 11 pages.
International Search Report and Written Opinion received for PCT Patent Application No. PCT/US2020/027921, mailed on Jul. 24, 2020, 16 pages.
Nakayama, Yasuhide. Microporous Stent Achieves Brain Aneurysm Occlusion Without Disturbing Branching Flow. NeuroNews Nov. 2012; 8:1-2.
Nishi S, Nakayama Y, Ishibashi-Ueda FI, Okamoto Y, Yoshida M. Development of microporous self-expanding stent grafts for treating cerebral aneurysms: designing micropores to control intimal hyperplasia. J Artif Organs 2011; 14:348-356.
Forward citations for E12 obtained from: https://scholar.google.com/scholar?cites=5981833429320176658&assdt=2005&sciodt=0,5&hl=en.
International Preliminary Report on Patentability received for PCT Patent Application No. PCT/US2020/044603, mailed on Feb. 10, 2022, 9 pages.
International Search Report and Written Opinion received for PCT Patent Application No. PCT/US2020/044603, mailed on Oct. 20, 2020, 12 pages.
Cardiac Surgery in the Adult, Third Edition, Chapter 2 2008.
EPO Form 1002 for EP16196687.4 Filed Dec. 28, 2016.

* cited by examiner

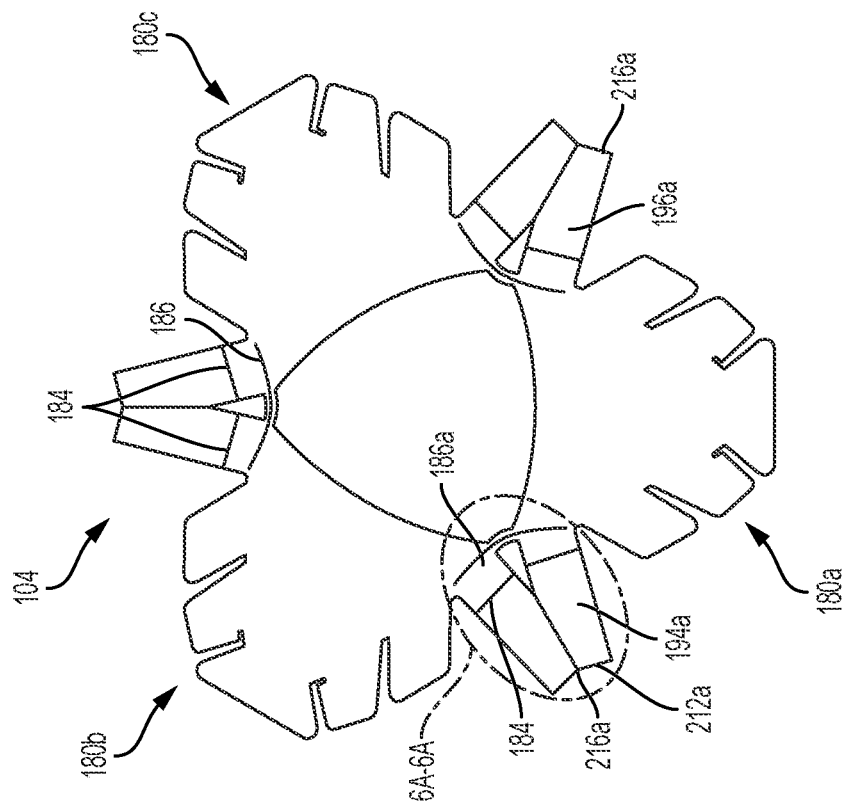
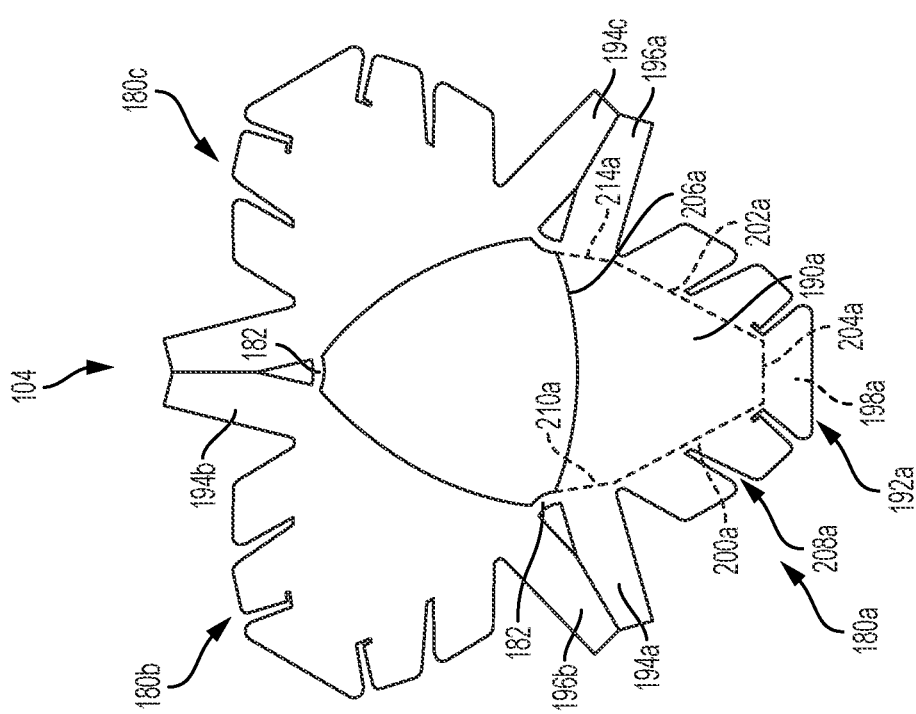

LEAFLET FRAME ATTACHMENT FOR PROSTHETIC VALVES

CROSS-REFERENCE TO RELATED APPLICATION

This application is a continuation of U.S. application Ser. No. 16/129,651, filed Sep. 12, 2018, which claims the benefit of U.S. Provisional Application No. 62/557,586, filed Sep. 12, 2017, and U.S. Provisional Application No. 62/564, 031, filed Sep. 27, 2017, both of which are incorporated herein by reference in their entireties for all purposes.

FIELD

The present disclosure relates to prosthetic valves, including prosthetic heart valves.

BACKGROUND

A number of fabrication techniques have been used to couple prosthetic valve leaflets to associated prosthetic valve frames, including sewing, injection molding, and dip coating polymeric leaflet material onto frames. In operation, prosthetic valve leaflets typically open after upstream fluid pressure exceeds downstream fluid pressure and close after downstream fluid pressure exceeds upstream fluid pressure. The terminal edges of the prosthetic valve leaflets will generally come into contact and coapt under the influence of downstream fluid pressure, closing the prosthetic valve to form a temporary seal that inhibits downstream blood from flowing retrograde through the prosthetic valve. The repeated opening and closing of leaflets can give rise to reliability issues, or even failure over time.

SUMMARY

Various embodiments are directed toward prosthetic valves having a frame and a leaflet construct, where the leaflet is at least partially coupled to a frame outer side by a looped structure. Some examples are directed to apparatuses, systems, and methods for valve replacement, such as cardiac valve replacement, although a variety of applications are contemplated.

According to one example, ("Example 1"), a prosthetic valve includes a frame having a central longitudinal axis, an inner side, and an outer side, the frame including a plurality of frame members and a plurality of commissure posts spaced circumferentially about the frame, the frame defining a plurality of leaflet attachment regions, the plurality of commissure posts including a first commissure post extending in a longitudinal direction and having a first slot formed through the first commissure post in a longitudinal direction, the first slot having a height and a width; a leaflet construct including a plurality of leaflets spaced circumferentially about the leaflet construct, the plurality of leaflets including a first leaflet and a second leaflet positioned circumferentially-adjacent to the first leaflet, the first leaflet including a first outer retaining element, a body portion having a first side and a second side, a first commissure tab extending from the first side, and a second commissure tab extending from the second side of the body portion, the first commissure tab having a first portion that extends through the first slot and a second portion that extends through the first slot to define a first outer loop portion on the outer side of the frame, the first outer loop portion encircling the first outer retaining element such that the first outer loop portion has a width that is greater than the width of the first slot to secure the first outer loop portion from being pulled through the first slot.

According to another example ("Example 2") further to Example 1, the second leaflet includes a second outer retaining element, a body portion having a first side and a second side, a first commissure tab extending from the first side of the body portion, and a second commissure tab extending from the second side of the body portion, the second commissure tab of the second leaflet having a first portion that extends through the first slot and a second portion that extends through the first slot to define a second outer loop portion on the outer side of the frame, the second outer loop portion encircling the second outer retaining element such that the second outer loop portion has a width that is greater than the width of the first slot to secure the second outer loop portion from being pulled through the first slot.

According to another example ("Example 3") further to Example 1, the first commissure post has a second slot formed through the first commissure post in a longitudinal direction, the second slot having a height and a width, and further wherein the second leaflet includes a second outer retaining element, a body portion having a first side and a second side, a first commissure tab extending from the first side of the body portion, and a second commissure tab extending from the second side of the body portion, the second commissure tab of the second leaflet having a first portion that extends through the second slot and a second portion that extends through the second slot to define a second outer loop portion on the outer side of the frame, the second outer loop portion encircling the second outer retaining element such that the second outer loop portion has a width that is greater than the width of the second slot to secure the second outer loop portion from being pulled through the second slot.

According to another example, ("Example 4") further to Examples 2 or 3, the first and second outer retaining elements are continuous to define a continuous outer retaining element extending between the first and second leaflets.

According to another example, ("Example 5") further to Example 4, the first commissure post further includes a hanging feature over which the outer continuous retaining element is hung to axially support the leaflet construct relative to the frame.

According to another example ("Example 6") further to any of the preceding Examples 1 to 5, the first leaflet further includes a first inner retaining element and the first commissure tab of the first leaflet further defines a first inner loop portion on the inner side of the frame, the first inner loop portion encircling the first inner retaining element such that the first inner loop portion has a width that is greater than the width of the first slot to secure the first inner loop portion from being pulled through the first slot.

According to another example ("Example 7"), further to Example 6 at least one of the first inner retaining element and the first outer retaining element is formed of one or more of a suture, a thread, a monofilament, a multifilament, and a bead of material.

According to another example ("Example 8"), further to Example 6 the first inner retaining element and the first outer retaining element are continuous to define a continuous retaining element.

According to another example ("Example 9"), further to any of the preceding examples, the leaflet construct defines a bridge between the first and second leaflets.

According to another example ("Example 10"), further to any of the preceding examples, wherein the first outer retaining element of the first leaflet is coupled to the first commissure tab by being molded, adhered and/or bonded to the first commissure tab of the first leaflet or wherein the leaflet includes a polymeric membrane and the first outer retaining element is coupled to the polymeric membrane by being molded, adhered and/or bonded to the polymeric membrane.

According to another example ("Example 11"), a prosthetic valve comprises a leaflet construct including a first leaflet and a first retaining element coupled to the first leaflet; and a frame having a slot operable to receive a portion of the leaflet therethrough that defines a first outer loop portion on an outer side of the frame through which a portion of the first retaining element is received, the frame further including a projection over which the first retaining element is received to axially support the leaflet construct.

According to another example ("Example 12") further to Example 11, the prosthetic valve further comprises a second leaflet, a portion of which is passed through the slot of the frame to define a second outer loop portion.

According to another example ("Example 13") further to Example 11, where the slot of the frame is a first slot and the frame further defines a second slot adjacent the first slot and the leaflet construct further includes a second leaflet, a portion of which is passed through the second slot of the frame to define a second outer loop portion.

According to another example ("Example 14") further to Example 11 the first leaflet defines a tab portion that extends through the slot at least two times, wherein the tab portion defines the outer loop portion.

According to another example ("Example 15") further to Example 11, the first leaflet defines a tab portion that extends through the slot at least three times, wherein the tab portion defines the outer loop portion and an inner loop portion on an inner side of the frame.

According to another example ("Example 16") further to Example 15, the leaflet construct further includes a second retaining element that extends through the inner loop portion.

According to another example ("Example 17") further to any of preceding Examples 14 to 16, a terminal end of the tab portion is coupled to another part of the tab portion by being molded, adhered, and/or bonded to another part of the tab portion.

According to another example ("Example 18") further to any of preceding Examples 14 to 16 a terminal end of the tab portion is coupled to another part of the first leaflet by being molded, adhered, and/or bonded to the other part of the first leaflet.

According to another example ("Example 19") further to any one of preceding Examples 11 to 18, the first leaflet includes a first tab portion a second tab portion, and a body portion between the first tab portion and the second tab portion, each of the first and second tab portions having a terminal end and a leaflet end opposite the terminal end, the first tab portion forming the first outer loop portion.

According to another example ("Example 20") further to Example 19, wherein the terminal end of the first tab portion is coupled to another part of the leaflet by being molded, adhered and/or bonded to the other part of the leaflet.

According to another example ("Example 21") a prosthetic valve includes a leaflet construct including a first leaflet; a first retaining element coupled to the first leaflet; a second retaining element coupled to the first leaflet; and a frame having a central longitudinal axis and a slot operable to receive a portion of the first leaflet therethrough that defines a first outer loop portion on an outer side of the frame through which a portion of the first retaining element is received and a first inner loop portion on an inner side of the frame through which a portion of the second retaining element is received.

According to another example ("Example 22") further to Example 21, the frame further includes a projection over which at least one of the first and second retaining elements is received to axially support the leaflet construct.

According to another example ("Example 23") further to any of preceding Examples 21 to 22, the leaflet construct includes a second leaflet and a bridge interconnecting the first and the second leaflets, wherein the bridge hangs over the projection.

According to another example ("Example 24") further to Example 21, the first leaflet includes a body portion, a first tab portion extending from a first side of the body portion to a terminal end, and a second tab portion extending from a second side of the body portion to a terminal end, the first tab portion forming the first inner loop portion and the first outer loop portion and the terminal end of the first tab portion be positioned adjacent the outer side of the frame.

According to another example ("Example 25"), further to any of preceding Examples 21 to 24 where the slot is a closed slot or where the slot extends from an open end to a closed end.

According to another example ("Example 26"), further to any of preceding Examples 21 to 25 where the first and second retaining elements are continuous.

According to another example ("Example 27"), further to any preceding Examples 21 to 26 where the slot is formed through the frame in a radial direction relative to a central longitudinal axis of the frame or the slot is formed at an angle to a radial direction relative to the central longitudinal axis of the frame.

According to another example ("Example 28"), further to any preceding claims 21 to 27 where tension on the first leaflet reduces a width of the slot.

According to another example ("Example 29"), further to any preceding Examples 21 to 28 where a cross-sectional area of the first retaining element and the outer loop portion is greater than a width of the slot.

According to another example ("Example 30"), further to any preceding Examples 21 to 29 where the first retaining element and the second retaining element define a continuous, closed loop portion.

According to another example ("Example 31"), a prosthetic valve comprises a leaflet construct including a first leaflet having a body portion, a first tab portion extending from the body portion, and a second tab portion extending from the body portion opposite to the first tab portion; a first retaining element coupled to the first leaflet; and a frame having a central longitudinal axis and a slot through which the first tab portion extends multiple times, including a first pass, a second pass, and a third pass through the slot.

According to another example ("Example 32"), further to Example 31 the first pass and the third pass are coupled and positioned adjacent to one other.

According to another example ("Example 33"), further to Example 31 the first pass is adjacent the second pass which is adjacent the third pass.

According to another example ("Example 34"), further to any preceding Examples 31 to 33 the first, second, and third passes are coupled to each other.

According to another example ("Example 35"), further to any preceding Examples 31 to 34 the first tab portion forms a first outer loop portion adjacent an outer side of the frame and that is restrained from pulling through the slot.

According to another example ("Example 36"), further to any preceding Examples 31 to 35 the first tab portion forms a first inner loop portion adjacent an inner side of the frame and that is restrained from pulling through the slot.

According to another example ("Example 37"), further to any preceding Examples 35 to 36 a first retaining element extends through the first outer loop portion.

According to another example ("Example 38"), further to Example 37 the first retaining element is coupled to the first outer loop portion.

According to another example ("Example 39"), further to any preceding Examples 35 to 38 a second retaining element extends through the first inner loop portion.

According to another example ("Example 40"), further to Example 39 the second retaining element is coupled to the first inner loop portion.

According to another example ("Example 41"), further to any preceding Examples 39 to 40 the first and second retaining elements are continuous.

According to another example ("Example 42"), further to Example 31, the first tab portion forms a first loop, and the leaflet construct further includes a second leaflet having a second tab portion defining a second loop, and further wherein the first retaining element extends into the first loop of the first leaflet and into the second loop of the second leaflet.

According to another example ("Example 43"), further to any preceding Examples at least one end of the first retaining element is enlarged relative to an adjacent portion of the first retaining element.

According to another example ("Example 44"), a prosthetic valve includes a frame having a central longitudinal axis; a leaflet construct including a first leaflet defining a first commissure tab, a second commissure tab, and a body portion therebetween, each tab portion having a terminal end and a leaflet end opposite the terminal end; a first retaining element; and a second retaining element, the frame having an inner side and an outer side and defining a slot through which the first tab portion is received, the first tab portion passing through the slot from the inner side to the outer side, passing from the outer side to the inner side, and passing again from the inner side to the outer side to define a first loop defining a first outer loop portion adjacent the outer side of the frame through which a first retaining element is received and a second loop between the inner side and outer side through which a second retaining element is received.

According to another example ("Example 45"), further to Example 44 the first leaflet defines a plurality of attachment tabs around a perimeter of the first leaflet that extend over the frame and coupled to the outer side of the frame.

According to another example ("Example 46"), further to Example 45 where each the attachment tabs is separated from an adjacent attachment tab by an opening for receiving a portion of the frame and optionally wherein the attachment tabs of the leaflets each include a plurality of apertures.

According to another example ("Example 47"), further to any one of Examples 44 to 46, in which the frame defines a plurality of commissure posts each including a first post leg and a second post leg that are spaced to define a slot.

According to another example ("Example 48"), further to Example 47 the leaflet construct includes a plurality of leaflets interconnected with one another by a plurality of bridges that pass through the slots of the commissure posts.

According to another example ("Example 49"), further to any one of Examples 44 to 48, the frame includes a plurality of frame elements that define a plurality of leaflet attachment regions each having a shape of an isosceles trapezoid having two leaflet attachment region sides diverging from a leaflet base.

According to another example ("Example 50"), further to Example 49 the leaflet base is perpendicular to the frame central longitudinal axis.

According to another example ("Example 51"), further to any one of Examples 44 to 49 the leaflet construct comprises at least one fluoropolymer membrane layer.

According to another example ("Example 52"), further to Example 52 a second material is contained within a porous structure of the expanded fluoropolymer membrane layer, coated on one or both sides of the expanded fluoropolymer membrane layer, or a combination of coated on and contained within the expanded fluoropolymer membrane layer.

According to another example ("Example 53"), further to any one of Examples 44 to 52 the leaflet construct comprises a composite having more than one fluoropolymer membrane layer.

According to another example ("Example 54"), further to any one of Examples 44 to 53 the frame comprises a metal, such as a shape memory metal, stainless steel, and/or a nickel-titanium alloy.

According to another example ("Example 55"), further to any one of Examples 44 to 54, wherein the leaflet construct comprises a fluoropolymer membrane layer including ePTFE.

According to another example ("Example 56"), further to any one of Examples 44 to 55 the leaflet construct defines a continuous annular ring.

According to another example ("Example 57"), a method of implanting a prosthetic valve in a body of a patient includes positioning a prosthetic valve according to any one of the preceding examples at a desired treatment location within the body and securing the prosthetic valve at the desired treatment location.

According to another example ("Example 58"), further to Example 57, the desired treatment location is a native aortic valve orifice and the method includes positioning the prosthetic valve at the native aortic valve orifice and securing the prosthetic valve at the native aortic valve orifice.

According to another example ("Example 59"), further to any one of Examples 57 or 58, the method includes positioning the prosthetic valve at the desired treatment location endoluminally with a transcatheter delivery system.

According to another example ("Example 60"), further to any one of Examples 57 to 59 the prosthetic valve is a self-expanding prosthetic valve.

According to another example ("Example 61"), further to any one of Examples 57 to 59 the prosthetic valve is a balloon expandable prosthetic valve.

According to another example ("Example 62"), further to any one of Examples 57 or 58, the method includes surgically positioning the prosthetic valve at the desired treatment location.

According to another example ("Example 63"), further to any one of Examples 57, 58, or 62, the prosthetic valve is a fixed frame, non-expandable prosthetic valve.

According to another example ("Example 64"), further to any preceding example, each of the plurality of leaflets defines two termini at an intersection of a leaflet free edge and a leaflet attachment region, the leaflet attachment region of each leaflet being coupled to the frame at a commissure attachment region of the frame such that the leaflet attachment regions adjacent the termini of two adjacent leaflets diverge relative to each other.

According to another example ("Example 65"), further to any preceding Example, the frame defines a pair of commissure attachment regions that diverge relative to each other toward a commissure post tip, and each leaflet is coupled to one of the commissure attachment regions such that adjacent leaflets define diverging free edges adjacent the commissure attachment regions.

According to another example ("Example 66"), further to any preceding Example, the frame defines a pair of adjacent commissure attachment regions that diverge relative to each other from a location away from a commissure post tip in an outflow direction towards the commissure post tip and a pair of adjacent leaflets of the plurality of leaflets is coupled to a respective one of the pair of adjacent commissure attachment regions such that the respective leaflet free edges of the pair of adjacent leaflets diverge from another at the adjacent commissure attachment regions when the pair of adjacent leaflets are in a closed, coapted configuration.

According to another example ("Example 67"), further to any preceding Example, each leaflet is attached to the frame such that adjacent leaflet free edges at the frame diverge relative to each other.

According to another example ("Example 68"), further to any preceding Example, each leaflet is attached to the frame at a diverging region of the frame such that adjacent leaflet free edges at the frame diverge relative to each other, wherein stress within each leaflet along the diverging region is reduced more than 40% relative to a non-diverging attachment when exposed to peak closing pressures of about 135 mmHg in the leaflet adjacent the free edges at the frame.

According to another example ("Example 69"), further to any one of Examples 1 to 10 or 64 to 68, a method of making the prosthetic valve includes coupling the first retaining element of a first leaflet to the first commissure tab of the first leaflet; and coupling the leaflet construct to the frame by extending the first portion and the second portion of the first commissure tab through the first slot of the frame to define the first outer loop portion on the outer side of the frame such that the first outer loop portion encircles the first outer retaining element and the first outer loop portion has a width that is greater than the width of the first slot to secure the first outer loop portion from being pulled through the first slot.

According to another example, ("Example 70"), further to any one of Examples 11 to 56 or 64 to 68, a method of making the prosthetic valve includes coupling the first retaining element to a first leaflet; and coupling the first leaflet of the leaflet construct to the frame by, receiving a portion of the leaflet through the slot that defines the first outer loop portion on the outer side of the frame with the first retaining element received through the first outer loop portion on the outer side of the frame, and receiving the first retaining element over the hanging feature of the frame to axially support the leaflet construct.

While multiple examples are disclosed, still other embodiments will become apparent to those skilled in the art from the following detailed description, which shows and describes illustrative examples. Accordingly, the drawings and detailed description are to be regarded as illustrative in nature and not restrictive.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

FIG. 5 is flat view of a leaflet construct prior to assembly to a frame, according to some embodiments.

FIG. 6 is a flat view of the leaflet construct of FIG. 5, shown with retaining elements, according to some embodiments.

Figure 1:
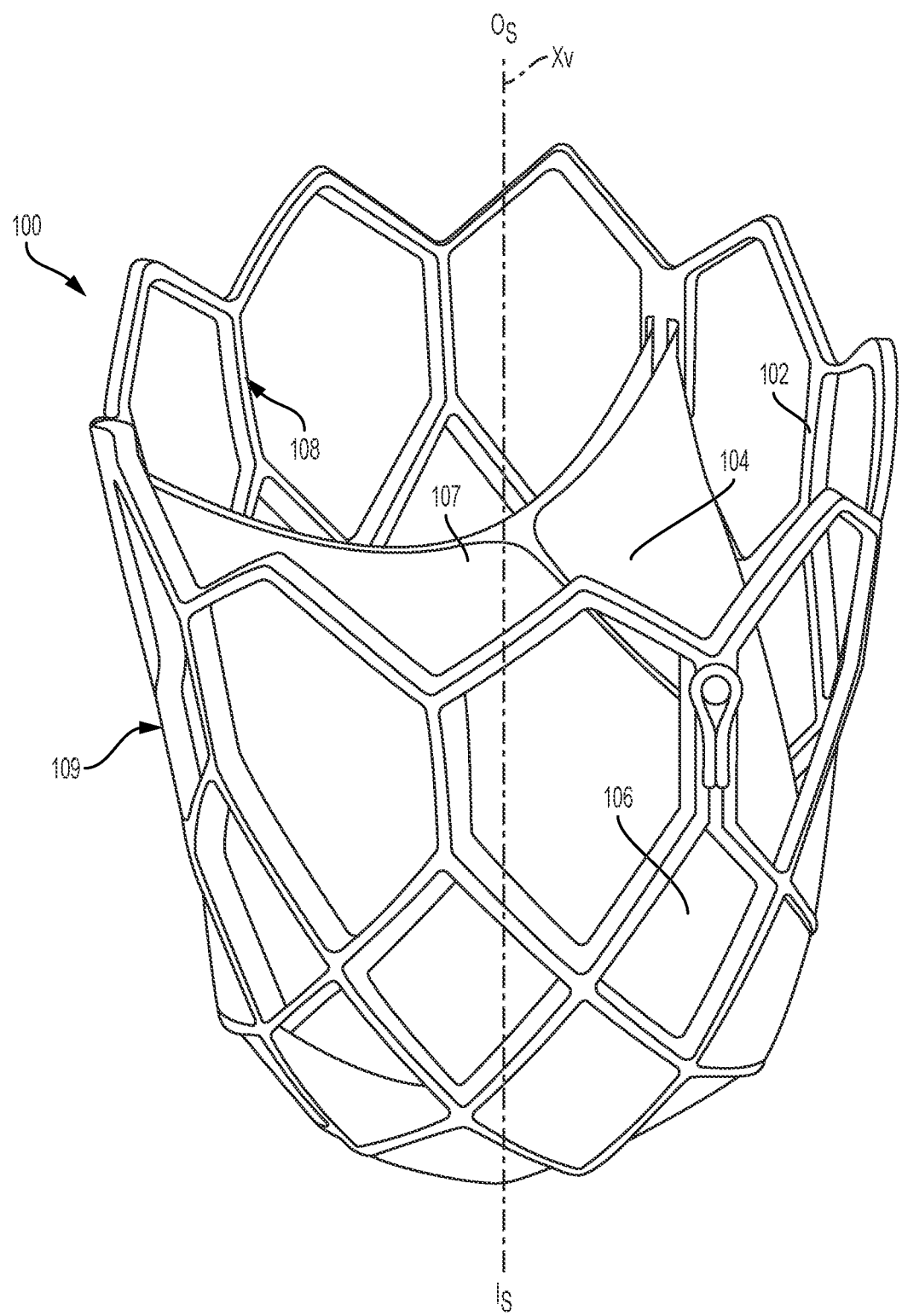
FIG. 1 is an isometric view of a prosthetic valve, according to some embodiments.

Persons skilled in the art will readily appreciate that various aspects of the present disclosure can be realized by any number of methods and apparatus configured to perform the intended functions. Stated differently, other methods and apparatuses can be incorporated herein to perform the intended functions. It should also be noted that the accompanying drawing figures referred to herein are not necessarily drawn to scale, but may be exaggerated or represented schematically to illustrate various aspects of the present disclosure, and in that regard, the drawing figures should not be construed as limiting.

DETAILED DESCRIPTION

The present disclosure relates to prosthetic valves used for cardiac valve replacement or other applications associated with native valve or other valve orifices, and related systems, methods, and apparatuses. In various examples, the prosthetic valve is operable as a one-way prosthetic valve that defines a valve orifice into which leaflets open to permit flow and close so as to block or occlude the valve orifice and partially or entirely prevent flow in response to differential fluid pressure.

In the instant disclosure, the examples are primarily described in association with surgical or transcatheter cardiac valve applications, although it should be readily appreciated embodiments within the scope of this disclosure can be applied toward any prosthetic valve or mechanism of similar structure and/or function. For example, the prosthetic valve 100 of FIG. 1 can be applied in non-cardiac applications, such as respiratory or gastrointestinal tract applications. Implantable valve orifices include anatomical structures into which a prosthetic valve can be placed. Such anatomical structures include, but are not limited to, a location wherein a cardiac valve may or may not have been surgically removed. Other anatomical structures that can receive a prosthetic valve include, but are not limited to, veins, arteries, ducts and shunts. A valve orifice or implant site may also refer to a location in a synthetic or biological conduit that may receive a prosthetic valve.

The term "leaflet" as used in the context of prosthetic valves is generally a flexible component operable to move between an open and closed position under the influence of pressure differentials. In an open position, the leaflet allows blood to flow through the prosthetic valve. In a closed position, the leaflet substantially blocks retrograde flow through the prosthetic valve. This retrograde flow is at least partially blocked, and typically fully blocked by the leaflet. In embodiments comprising multiple leaflets, each leaflet cooperates with at least one neighboring leaflet to block the retrograde flow of blood. Various embodiments relate to attachment mechanisms for coupling leaflets to an associated frame such that the leaflets resist inward forces, outward forces, and/or axial forces on the leaflets relative to the associated frame. The leaflet frame attachment mechanisms for prosthetic valves include the leaflet construct being at least partially coupled to a frame outer side by a looped structure. Such looped structures can help provide reduced stress concentrations, greater reliability of attachment, and ease of manufacture.

The pressure differential in the blood actuating the leaflets is caused, for example, by the contraction of a ventricle or atrium of the heart, such pressure differential typically resulting from a fluid pressure building up on one side of the leaflets when closed. As the pressure on an inflow side of the prosthetic valve rises above the pressure on the outflow side of the prosthetic valve, the leaflets open and blood flows therethrough. As blood flows through the prosthetic valve into a neighboring chamber or blood vessel, the pressure on the inflow side equalizes with the pressure on the outflow side. As the pressure on the outflow side of the prosthetic valve raises above the blood pressure on the inflow side of the prosthetic valve, the leaflet returns to the closed position to partially or fully block retrograde flow of blood through the prosthetic valve.

FIG. 1 is an isometric view of a prosthetic valve 100, according to some embodiments. As shown, the prosthetic valve 100 includes a frame 102, also described as a frame assembly or leaflet frame, a leaflet construct 104, also described as a leaflet assembly or leaflet module, and an attachment element 106, which can also be described as an attachment substrate or an attachment treatment. The prosthetic valve 100 can include any of a variety of additional features, such as one more sealing cuffs, for example. The leaflet construct 104 has a plurality of leaflets 180 (FIG. 5) that come together where free edges 206 (FIG. 5) flatten together (e.g., in a Y-shaped pattern in the case of three leaflets when viewed from the top), which can also be described as a coaptation region 107. As the free edges 206 come together the prosthetic valve 100 closes. The prosthetic valve 100 closes in this fashion when the pressure of the blood on the outflow side $O_s$ is greater than the pressure of the blood on the inflow side $I_s$ of the prosthetic valve 100. The leaflet free edges of leaflet construct 104 move apart to open the prosthetic valve 100 and to let blood flow through the prosthetic valve 100 from the inflow side $I_s$ when the pressure of the blood on the inflow side $I_s$ of the prosthetic valve 100 is greater than the pressure on the outflow side $O_s$ of the prosthetic valve 100. As shown, the prosthetic valve 100 defines a central longitudinal axis Xv, as well as an inner side 108 corresponding to a central lumen and an outer side 109 corresponding to the exterior of the prosthetic valve 100.

Figure 2:
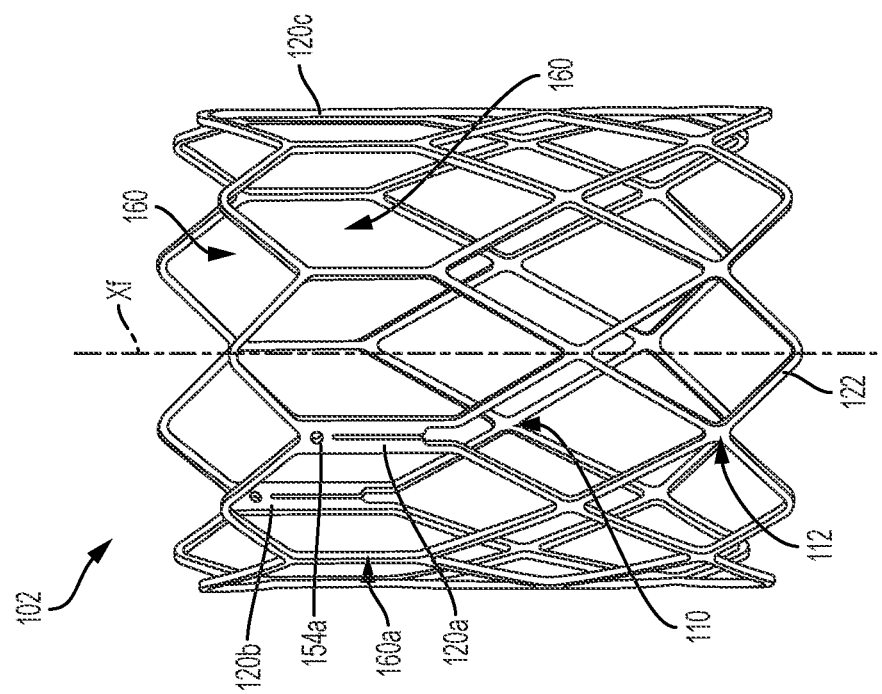
FIG. 2 is an isometric view of a frame of the prosthetic valve of FIG. 1, according to some embodiments.

FIG. 2 is a perspective view of the frame 102 of the prosthetic valve 100, according to some embodiments. In various examples, the frame 102 serves to operatively support the leaflet construct 104 in a desired location within a patient (not shown). The frame 102 is optionally collapsible to a reduced profile, delivery configuration and then expandable (e.g., self-expanding or expanded by the application of an external force, such as by balloon expansion) in situ. As shown in FIG. 2, the frame 102 is optionally annular, defining a cylinder (e.g., a right circular cylinder) or cylindrical shape, and has a central longitudinal axis Xf.

Although the frame 102 generally defines a circular transverse cross-section, it should be understood that any variety of cross-sections (e.g., oval- or rectangular-shaped) cross-sections are also contemplated. The frame 102 has an inner side 110 and an outer side 112 opposite the inner side 110. The inner side 110 faces toward the central longitudinal axis Xf, and the outer side 112 faces outwardly, or away from the central longitudinal axis Xf. As shown, the frame 102 includes a plurality of commissure posts 120 (FIG. 3) and a plurality of frame elements 122.

The frame 102 can be etched, cut, laser cut, stamped, three-dimensional printed or wire wound, among other suitable processes. The frame 102 can comprise, such as, but not limited to, any metallic or polymeric material, such as an elastically (e.g., nitinol) or plastically (e.g., stainless steel) deformable metallic or polymeric material that is generally biocompatible. Other materials suitable for the frame 102 include, but are not limited to, other titanium alloys, stainless steel, cobalt-nickel alloy, polypropylene, acetyl homopolymer, acetyl copolymer, a drawn filled tube (e.g., nitinol wire with a platinum core), other alloys or polymers, or any other material that is generally biocompatible having adequate physical and mechanical properties to function as a frame 102 as described herein.

In some embodiments, the plurality of commissure posts 120 are spaced from one another, and arranged at desired locations (e.g., equally spaced locations) around a circumference of the frame 102. As shown, the plurality of commissure posts 120 extend parallel to the central longitudinal axis Xf, although angled configurations (e.g., commissure posts angled inwardly toward the central longitudinal axis Xf or outwardly away from the central longitudinal axis Xf) are also contemplated. Although three, equally circumferentially-spaced commissure posts 120 are shown, any number and spacing of commissure posts are contemplated. The plurality of commissure posts 120 define circumferentially-adjacent ones, or simply adjacent ones of the plurality of commissure posts 120 moving about the perimeter of the frame 102. As shown in FIG. 2, other than location and orientation, each of the commissure posts 120 has a similar design, although examples where the commissure posts differ from one another in various respects are also contemplated. For ease of understanding, the features of each of the commissure posts 120 will be described in association with a first commissure post 120a, an enlarged view of which is shown in FIG. 3.

The features of the first commissure post 120a will generally be referenced with a numeral followed by an "a." Similar features of a second commissure post may be subsequently referenced with the same numeral as the first commissure post 120a, but followed by a "b." Similar features of a third commissure post may be subsequently referenced with the same numeral as the first commissure post 120a, but followed by a "c." Similarly, when features of each of the commissure posts 120 are referenced collectively, those features are referenced with the same numeral as identified for the first commissure post 120a, but not followed by a letter.

Figure 3:
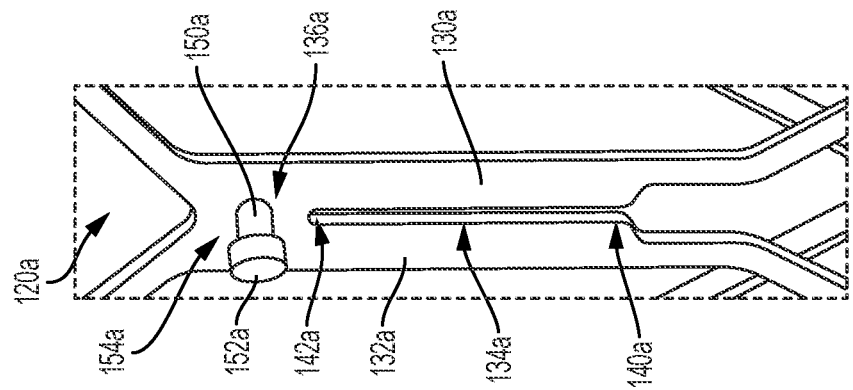
FIG. 3 is an enlarged view of a portion of the frame of FIG. 2, according to some embodiments.

As shown in FIG. 3, the first commissure post 120a, includes a first leg 130a, a second leg 132a, a slot 134a between the first leg 130a and the second leg 132a, which can also be described as a post slot, and a hanging feature 136a, which can also be described as a protuberance, hook, or projection. The first commissure post 120a has an outer side corresponding to the frame outer side 112 (FIG. 2) and a post inner side corresponding to the frame inner side 110 (FIG. 2).

As shown, the first and second legs 130a, 132a extend longitudinally, or in a longitudinal direction. In some examples, the first and second legs 130a, 132a extend in a longitudinal direction that is parallel to the central longitudinal axis Xf (FIG. 2) of the frame 102. In other examples, the first and second legs 130a, 132a extend longitudinally, but at some offset relative to the central longitudinal axis Xf (e.g., angularly offset inwardly, toward the central longitudinal axis Xf, angularly offset transversely relative to the central longitudinal axis Xf, or a combination thereof).

The slot 134a is optionally formed between the first and second legs 130a, 132a and extends through a thickness of the first commissure post 120a, from the inner side 110 (FIG. 2) of the frame 102 to the outer side 112 (FIG. 2) of the frame 102. The slot 134a is formed through the frame 102 in a radial direction relative to a central longitudinal axis Xf of the frame 102 or the slot 134a is formed at an angle to a radial direction relative to the central longitudinal axis Xf of the frame 102. As shown, the slot 134a extends in a longitudinal direction that is parallel to the central longitudinal axis Xf (FIG. 2) of the frame 102. In other examples, the slot 134a extends longitudinally, but at some offset relative to the central longitudinal axis Xf (e.g., angularly offset inwardly, toward the central longitudinal axis Xf, angularly offset transversely relative to the central longitudinal axis Xf, or a combination thereof). As shown, the slot 134a is elongate in shape, with a length, or height, greater than its width (e.g., more than 2×, 5×, 10×, 20×, or 30×, although a variety of dimensions are suitable), and extends from a first end 140a to a second end 142a. As shown, the first end 140a of the slot 134a is open and the second end 142a of the slot 134a is closed. For example, the first end 140a is "open" in the sense that it opens to a much wider area in the frame 102 (e.g., more than 5×, 10×, or 20×), whereas the second end 142a is "closed" in the sense that it terminates at a distance from the first end 140a of the slot 134a. The width of the slot 134a is generally selected to allow a desired number of passes or loops of leaflet material through the slot 134a as described below.

In some embodiments, the hanging feature 136a, which can also be described as a hanger, a protuberance, a projection a shoulder, a pin, or a hook, for example, includes a body portion 150a and a head portion 152a, where the body portion 150a is secured through a hole 154a, or aperture, in the frame 102 (the receiving hole is hidden in FIG. 3, but can be seen in FIG. 2 without the hanging feature 136a for ease of understanding). The head portion 152a generally defines a shoulder, and forms a channel 156a between the head portion 152a and the frame 102. The depth and width of the channel 156a is generally selected to receive and retain a filament or other desired portion of the leaflet construct 104 for axially supporting the leaflet construct 104. As shown, the hanging feature 136a is located longitudinally-adjacent the second end 142a of the slot 134a, and generally in alignment with the slot 134a. In other examples, the hanging feature 136a is offset from the slot 134a (e.g., laterally/circumferentially).

Figure 4:
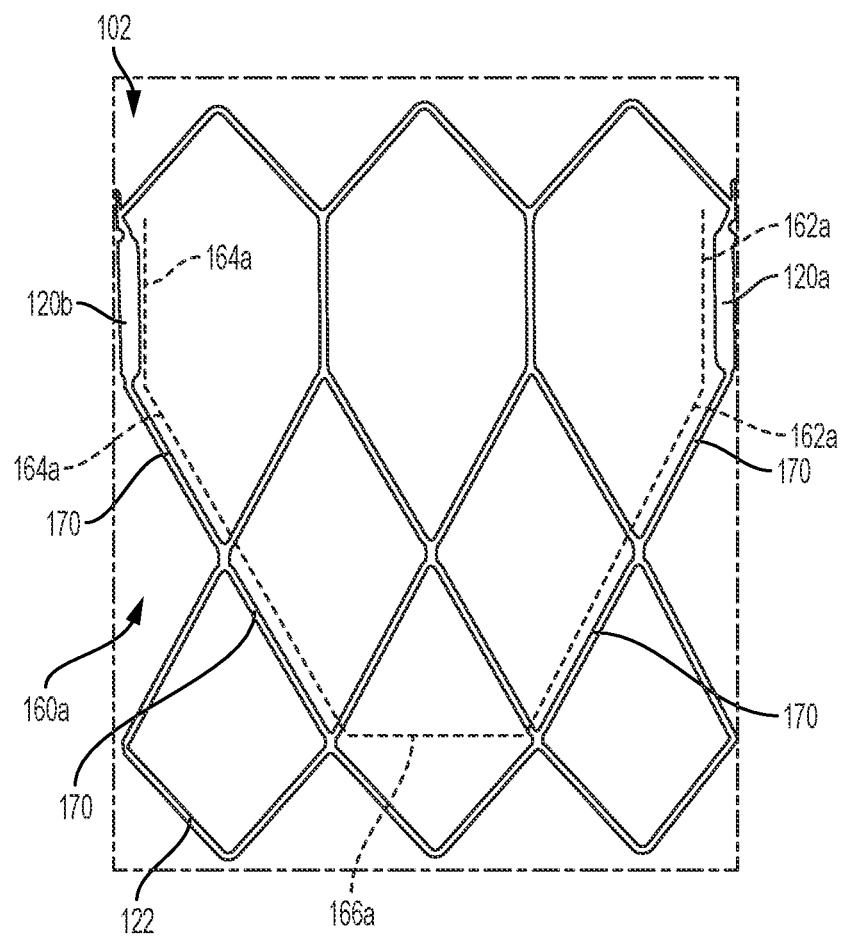
FIG. 4 is an enlarged, schematic view of a portion of the frame of FIG. 3 corresponding to a first leaflet attachment region, according to some embodiments.

FIG. 4 is an enlarged, flattened view of a first leaflet attachment region 160a of the frame 102 between two adjacent commissure posts 120, the first commissure post 120a and second commissure post 120b, according to some embodiments. The first leaflet attachment region 160a defines a first side 162a, a second side 164a, and a base 166a. Similar leaflet attachment regions 160 are defined between each of the adjacent commissure posts 120, according to some embodiments. In FIG. 4, the first leaflet attachment region 160a of the frame 102 is represented in a flattened form for ease of illustration, although it should be understood that the frame 102 is three-dimensional and generally annular. As shown in FIG. 4, the first commissure post 120a is located at a first side of the first leaflet attachment region 160a of the frame 102 and a second commissure post 120b of the plurality of commissure posts 120 is located at a second side of the first leaflet attachment region 160a of the frame 102 shown in FIG. 4. In particular, the frame 102 defines the first leaflet attachment region 160a between the first and second commissure posts 120a, 120b, as well as leaflet attachment regions between the remaining commissure posts of the plurality of commissure posts 120.

In some embodiments, the frame elements 122 of the frame 102 include a plurality of leaflet attachment frame elements 170, or simply leaflet attachment elements, that define leaflet attachment regions similar to the first leaflet attachment region 160*a* shown in FIG. 4. The leaflet attachment frame elements 170 are arranged to support the leaflet construct 104 and to help define a shape of leaflets 180 (FIG. 5) of the leaflet construct 104, where that leaflet 180 will project from the corresponding leaflet attachment region, such as the first leaflet attachment region 160*a*. In the example shown in FIG. 2, the frame 102 defines three sets of the leaflet attachment frame elements 170 corresponding to three leaflet attachment regions 160 that each generally follows the shape of an outline of a leaflet of the leaflet construct 104. In different terms, the leaflet attachment frame elements 170 optionally support leaflets around at least a portion of each of the leaflets 180 except at the free edges 206 (FIG. 5).

FIG. 5 shows the leaflet construct 104 as a flattened, plan view prior to assembly with the frame 102. This flattened plan view can also be described as a cut pattern, or simply a leaflet pattern. From FIG. 1, for example, it should be understood that the leaflet construct 104 is folded and formed into a cylindrical shape when assembled to the frame 102. As shown in FIG. 5, the leaflet construct 104 includes a plurality of leaflets 180 and a plurality of bridges 182, or bridge regions, interconnecting the circumferentially-adjacent leaflets 180. In some embodiments, the plurality of leaflets 180 are spaced from one another, and arranged at desired locations around a circumference of the leaflet construct 104 corresponding to the respective leaflet attachment regions 160 and commissure posts 120. As shown in FIGS. 5 and 6, the leaflet pattern defines a connected and continuous (e.g., monolithic, contiguous or seamless) annular ring formed as a single piece and including the plurality of leaflets 180 and bridges 182 between each of the plurality of leaflets 180.

Although three leaflets 180 are shown, any number of leaflets is contemplated. The plurality of leaflets 180 define circumferentially-adjacent ones, or simply adjacent ones of the plurality of leaflets 180 moving about the circumference of the leaflet construct 104. The leaflet construct 104 can be formed in a variety of manners, including cutting a cylinder of material into a desired shape, cutting a sheet of material into a desired shape, and/or molding (e.g., compression or injection molding) the leaflet construct 104 with a desired shape.

As shown in FIG. 6, the leaflet construct 104 also includes a plurality of first retaining elements 184, and a plurality of second retaining elements 186 (the retaining elements are not shown in FIG. 5 for ease of visualization of the bridges 182). As used herein, a retaining element includes one or more of a strand, filament, monofilament, multifilament (whether braided, woven, twisted or an otherwise associated group of filaments), a bead of material, a thread, a suture, a rolled film, a multilayer lay-up of material, a wire, an embossed or other feature providing the functionality described herein.

The first and second retaining elements 184, 186 are optionally molded, adhered, and/or heat bonded, or otherwise coupled to the leaflet construct 104 as desired. As used herein, couple means to join, connect, attach, adhere, affix, or bond, whether directly or indirectly, and whether permanently or temporarily.

In some examples, the first retaining elements 184 are not present. For example, the retaining elements 184*a*, 184*b* may be unnecessary in instances where there is a desired amount of support/retention provided by the second retaining elements 186.

As shown in FIGS. 5 and 6, other than location and orientation, each of the plurality of leaflets 180 has a similar design, although examples where the leaflets differ from one another in various respects are also contemplated. Regardless, for ease of understanding, the features of each of the leaflets 180 will be described in association with a first leaflet 180*a*. The features of the first leaflet 180*a* will generally be referenced with a numeral followed by an "a." Similar features of a second leaflet may be subsequently referenced with the same numeral as the first leaflet, but followed by a "b." Similar features of a third leaflet may be subsequently referenced with the same numeral as the first leaflet 180*a*, but followed by a "c." Similarly, when features of each of the leaflets 180 are referenced collectively, those features are referenced with the same numeral as identified for the first leaflet 180*a*, but not followed by a letter.

As indicated on FIG. 5, the first leaflet 180*a* optionally includes a body portion 190*a*, a plurality of attachment tabs 192*a* extending from the body portion 190*a*, a first commissure tab 194*a* extending from the body portion 190*a*, and a second commissure tab 196*a* extending from the body portion 190*a* (e.g., at opposite ends of free edge 206*a*). As previously discussed, the second and leaflets 180*b*, 180*c* optionally include similar features. For example, as shown in FIG. 5, the second leaflet 180*b* includes a first commissure tab 194*b* and a second commissure tab 196*b*. As shown, the first commissure tab 194*a* is positioned adjacent the second commissure tab 196*b* and the second commissure tab 196*a* is positioned adjacent a first commissure tab 194*c* of the third leaflet 180*c*.

The body portion 190*a*, also described as a leaflet belly, or belly portion, is bounded in broken lines for understanding purposes. The body portion 190*a* of the first leaflet 180*a* is the moving portion of the first leaflet 180*a* in the prosthetic valve 100. It should be appreciated that when assembled to the frame 102, the boundaries of the body portion 190*a* are defined and the body portion 190*a* takes on a three dimensional shape, rather than the flat shape shown in FIG. 5. As such, the broken lines are provided for general visualization purposes of the body portion 190*a*. In various examples, the shape of the body portion 190*a* is generally dictated by the lines, or areas of attachment to the frame 102. The edges of the body portion 190*a* generally correspond to fold lines where the attachment tabs 192*a* and the first commissure tab 194*a* and the second commissure tab 196*a* are secured to the frame 102 (FIG. 2). As will be described below, the leaflet construct 104 may be attached to the frame 102 using attachment element 106 (FIG. 1), which in turn, may contribute to shape defined by the leaflet attachment regions 160 and the ultimate shape of the body portion 190*a*.

As shown, the body portion 190*a* of the first leaflet 180*a* has the general shape of an isosceles trapezoid. Regardless of the exact shape, the body portion 190*a* generally has a first side 200*a*, a second side 202*a*, a base 204*a*, and a free edge 206*a* opposite the leaflet base 204*a* for coaptating with respective free edges 206 of respective other leaflets 180. In general terms, the shape of the body portion 190*a* corresponds to the first side 162*a*, the second side 164*a*, and the base 166*a* of the first leaflet attachment region 160*a* (FIG. 4). As shown, the two sides 200*a*, 202*a* diverge from the leaflet base 204*a*, and the leaflet base 204*a* will be substantially straight in a transverse plane relative to the central longitudinal Xf of the frame 102. In different terms, leaflet base 204*a* is perpendicular to the central longitudinal axis Xf of the frame 102 following assembly.

Although the body portion 190*a* is shown to take on the general shape of an isosceles trapezoid, any number of shapes is contemplated, and the body portion 190*a* need not be trapezoidal in overall appearance. For example, the body portion 190*a* may include a central region that defines a shape substantially that of an isosceles trapezoid, with side regions on each side that have a shape substantially that of a triangle. In still other embodiments, the body portion 190*a* may outline a shape that can be described as U-shaped, parabolic shaped, or a V-shaped, depending on the geometric outline defined by the first leaflet attachment region 160*a*.

The first leaflet 180*a* generally defines a fold over portion 198*a*, also described as a fold over region, outside of the body portion 190*a*, as demarcated by the broken line in FIG. 5. The fold over portion 198*a* of the first leaflet 180*a* is the portion that is used to secure the first leaflet 180*a* to the frame 102, where the remaining leaflets 180 optionally include similar features for securing to the frame 102. The leaflet attachment frame elements 170 (FIG. 4) fit into a fold that is formed between the body portion 190*a* and the fold over portion 198*a*. In general terms, the leaflets 180 extend radially inward from the frame 102 when coupled to the frame 102. The body portion of each leaflet 180 includes enough material between the commissure posts 120 of the frame 102 so that the leaflet free edges 206 of the three leaflets 180 can come together or coapt in the interior of the prosthetic valve 100 to close the prosthetic valve 100 as shown in FIG. 1.

As shown, the plurality of attachment tabs 192*a* located in the fold over portion 198*a* are positioned about a perimeter of the body portion 190*a* and are separated from one another by openings 208*a* for receiving frame elements 122 (e.g., leaflet attachment frame elements 170) of the frame 102. One or more of the plurality of attachment tabs 192*a* optionally includes a plurality of apertures (not shown) through the thickness of the attachment tabs 192*a*. The apertures may assist with coupling or otherwise securing the attachment tabs 192*a* to the frame 102 (e.g., directly or via the attachment element 106) using adhesives or bonding (e.g., to provide additional surface area for adhesion/bonding), fastening elements (e.g., holes for sutures), or combinations thereof.

In various examples, the first commissure tab 194*a* and the second commissure tab 196*a* assist with securing the first leaflet 180*a* to the first commissure post 120*a* and second commissure post 120*b* (FIGS. 2, 4). As shown in FIG. 5, the first commissure tab 194*a* extends from the first side 200*a* of the body portion 190*a* and the second commissure tab 196*a* extends from a second side 202*a* of the body portion 190*a*. The first commissure tab 194*a* extends from a first end 210*a*, also described as a leaflet end, to a terminal end 212*a* (FIG. 6). Similarly, the second commissure tab 196*a* extends from a first end 214*a* to a terminal end 216*a* (FIG. 6). The first commissure tab 194*a* and second commissure tab 196*a* are shown with an optional taper toward the terminal ends 212*a*, 216*a*.

Figure 6A:
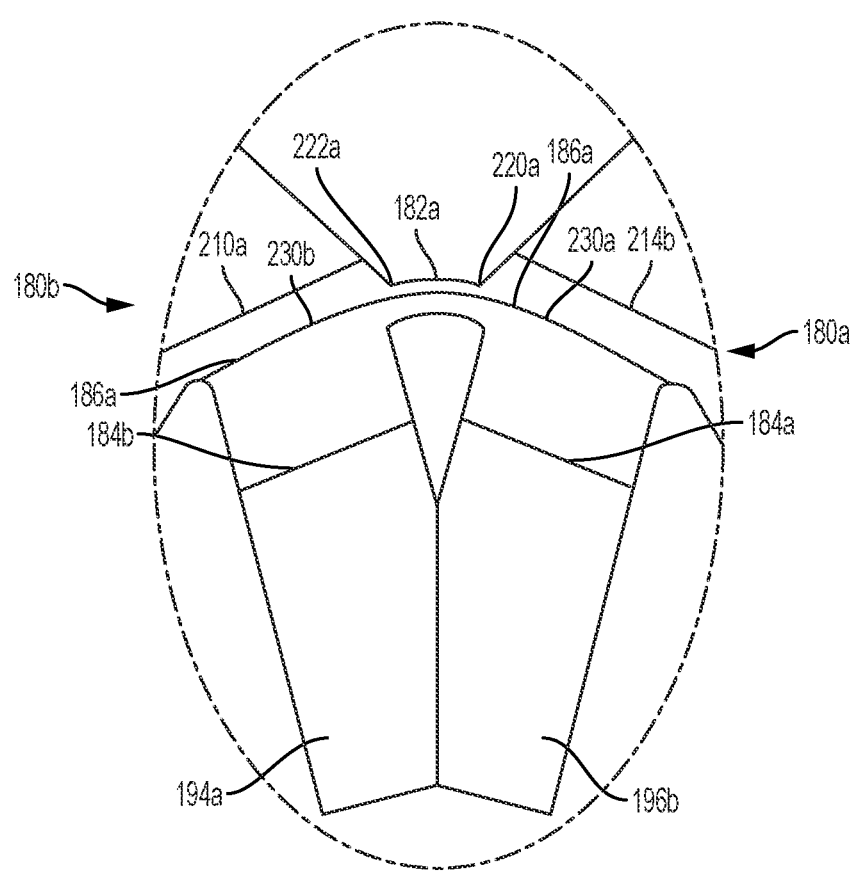
FIG. 6A is an enlarged flat view of the leaflet construct of FIG. 6, shown with retaining elements, according to some embodiments.

As shown, the plurality of bridges 182 extend between and interconnect the plurality of leaflets 180. FIG. 6A is an enlarged view of a portion of FIG. 6, and illustrates a bridge 182*a* of the plurality of bridges 182. Each of the bridges 182 is optionally substantially similar, and as such can be described cumulatively with reference to the bridge 182*a* (although varying bridge designs from bridge-to-bridge are also contemplated). As shown in FIG. 6A, the bridge 182*a* interconnects, or otherwise extends between a first end 220*a* adjacent to the first leaflet 180*a* and a second end 222*a* adjacent the second leaflet 180*b*. When the leaflet construct 104 is folded into a cylindrical shape and the leaflet construct 104 is folded onto frame 102, the bridge 182*a* (and each of the bridges 182) defines a loop between the first end 220*a* and the second end 222*a*. The loops defined by the bridges 182, as well as the remaining portions of the leaflets 180 that are secured to the commissure posts 120 can also be described as coaptation necks. In some embodiments, These coaptation necks are operable to pass through the slots of the commissure posts 120, such as the slot 134*a* of the first commissure post 120*a*, so that the loop formed by folding the bridge 182*a* is adjacent to the outer side 112 of the frame 102, which also corresponds to the outer side of the first commissure post 120*a* (FIG. 2).

As shown, the first leaflet 180*a* includes a first retaining element 184*a* that is located on the first commissure tab 194*a* and the second leaflet 180*b* includes a first retaining element 184*b* that is located on the second commissure tab 196*b* of the second leaflet 180*b* near the first end 214*b* of the second commissure tab 196*b*. The first retaining elements 184*a*, 184*b* of the respective leaflets 180*a*, 180*b* are separate and discontinuous from one another and they are not formed as a single or contiguous piece. In turn, the second retaining element 186*a* extends across, or overlays, the bridge 182*a* and onto each of the first leaflet 180*a* and the second leaflet 180*b* and is optionally a single, connected and continuous (e.g., contiguous) member or element. The second retaining element 186*a* defines a first portion 230*a* on the first leaflet 180*a* and a second portion 230*b* on the second leaflet 180*b*. Each of the portions is optionally individually referred to as elements as well. In different terms, the first leaflet 180*a* includes second retaining element 186*a*, the second leaflet 180*b* includes second retaining element 186*b*, and the second retaining elements 186*a*, 186*b* are connected and continuous (e.g., contiguous) with one another as a single piece to define the second retaining element 186*a*. As shown, the first retaining elements 184*a*, 184*b* are spaced apart from the second retaining element 186*a*. In some examples, the first retaining elements 184 (e.g., 184*a*, 184*b*) are spaced apart from their adjacent second retaining elements 186 (e.g., 186*a*) a distance at least as wide as the thickness of a corresponding commissure post 120 (e.g., 120*a*) as measured from the inner side 110 to the outer side 112 of the frame 102.

As previously referenced, the various retaining elements can take a variety of forms. In some examples, the first retaining elements 184 are formed as beads of material on the commissure tabs of the leaflets 180, whereas the second retaining elements 186 are fibers (e.g., coated fibers). The various retaining elements are optionally molded, adhered and/or bonded to the underlying material of the leaflets 180, such as by thermal bonding. In some examples, the second retaining elements 186 help reinforce the bridges 182, provide connections between the leaflets 180, and/or are used to affect retention of the first and the second commissure tabs 194, 196 in the slots 134 of the commissure posts 120. As will be described below, in some examples, the second retaining elements 186 are located adjacent the slots 134 at the outer side 112 and the first retaining elements 184 are located adjacent the slots 134 at the inner side 110 of the frame 102. The second retaining elements 186 are optionally used to help prevent the first and the second commissure tabs 194, 196 and bridges 182 from pulling inwardly through the slots 134, wherein the first retaining elements 184 are optionally used to help prevent the leaflets 180 from pulling outwardly through the slots 134 to the outer side 112 of the frame 102. For example, cross-sectional areas of the retaining elements 184, 186 and portions of the commissure tabs 194, 196 looped over them are greater than the widths of the slots 134.

The first retaining elements 184 and/or the second retaining elements 186 can be formed from polymeric or metallic materials, fluoropolymers, one or more of FEP, PEEK, ePTFE filament(s) (mono- or multi-), nitinol, stainless steel, multiple folds or layers of material (e.g., ePTFE film), combinations thereof, or any of a variety of features configured to resist movement relative to the slot(s) and/or hanging feature(s).

Figure 7:
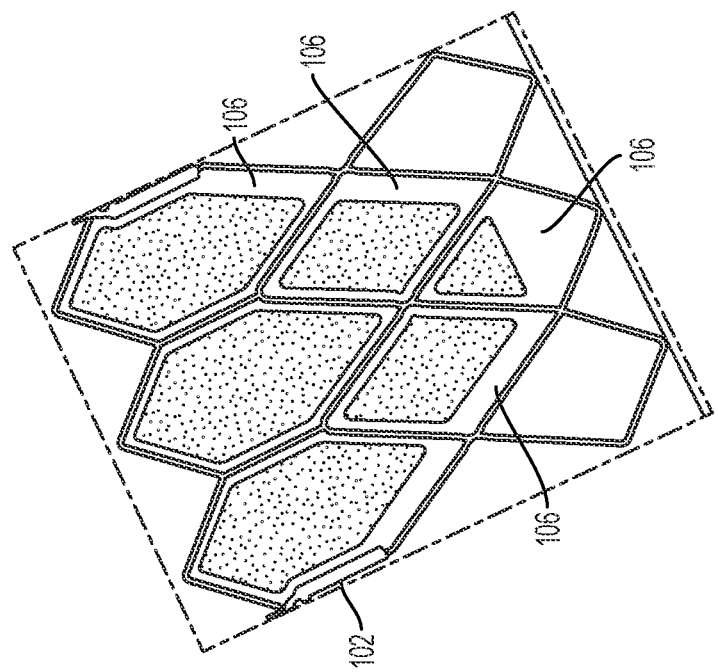
FIG. 7 is an enlarged, schematic view of a portion of the frame of FIG. 3 corresponding to a first leaflet attachment region, according to some embodiments.

FIG. 7 is a schematic, flat view of a portion of the frame 102 and attachment element 106. The gray area in FIG. 7 represents locations where the attachment element 106 is not present. For example, the attachment element is optionally one or more layers of material applied to the frame material. If desired, the openings, or gray areas in the attachment element 106 are optionally formed via laser cutting (e.g., where the attachment element is applied to the frame 102 as part of a tape wrapping process. Several locations of the attachment element 106 are marked on FIG. 7 for ease of understanding. As previously referenced, the prosthetic valve 100 optionally includes attachment element 106, which can also be described as an attachment substrate or an attachment treatment. The attachment element 106 is optionally one or more layers of material attached to the frame 102. In some examples, the outer side 112 of the frame 102 is covered with the attachment element 106, which is in the form of one or more layers of film material. One or more portions of the leaflet construct 104 can then be attached to the attachment element 106, thereby helping to define the shapes of the leaflets 180.

Figure 8:
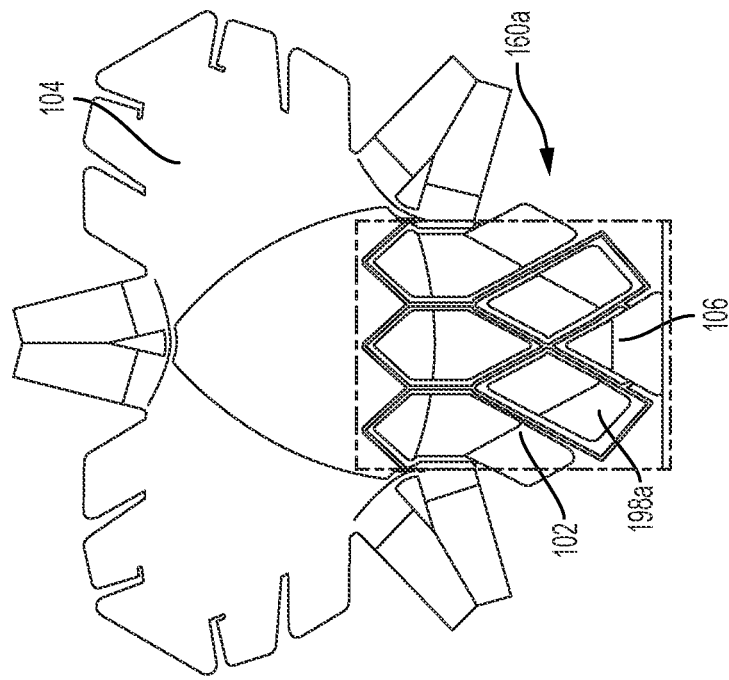
FIG. 8 is a schematic, flat view showing a portion of the frame of FIG. 3 corresponding to a first leaflet attachment region superimposed on a portion of the leaflet construct of FIG. 6 corresponding to a first leaflet, according to some embodiments.

FIG. 8 shows an overlay of the frame 102, the leaflet construct 104, and the attachment element 106 in an area of the first leaflet attachment region 160a, for understanding, where similar principles of which apply in assembling the remaining leaflets 180 to leaflet attachment regions of the frame 102. As referenced above, the leaflet construct 104 is attached to the frame 102 and/or attachment element 106 using fold over portions, such as the fold over portion 198a of the first leaflet 180a. Attachment tabs, such as the attachment tabs 192a of the first leaflet 180a are received over portions of the frame 102 and/or attachment element 106 and attached thereto to attach the leaflet construct 104 to the frame at the body portions of the leaflets 180, such as the body portion 190a (FIG. 5). As should be understood, one or more of the attachment tabs 192a may be folded to the attachment element 106, rather than the frame 102. As shown in FIG. 8, the lowermost attachment tab 192a may be folded to a relatively flat area at the bottom of the attachment element 106, to define a relatively flat base corresponding to that shown for the body portion 190a in FIG. 5. In different terms, the attachment tabs do not necessarily have to follow the geometry of the frame 102, but can follow a geometry separate from the frame 102 as defined by the attachment element 106, for example.

Figure 9:
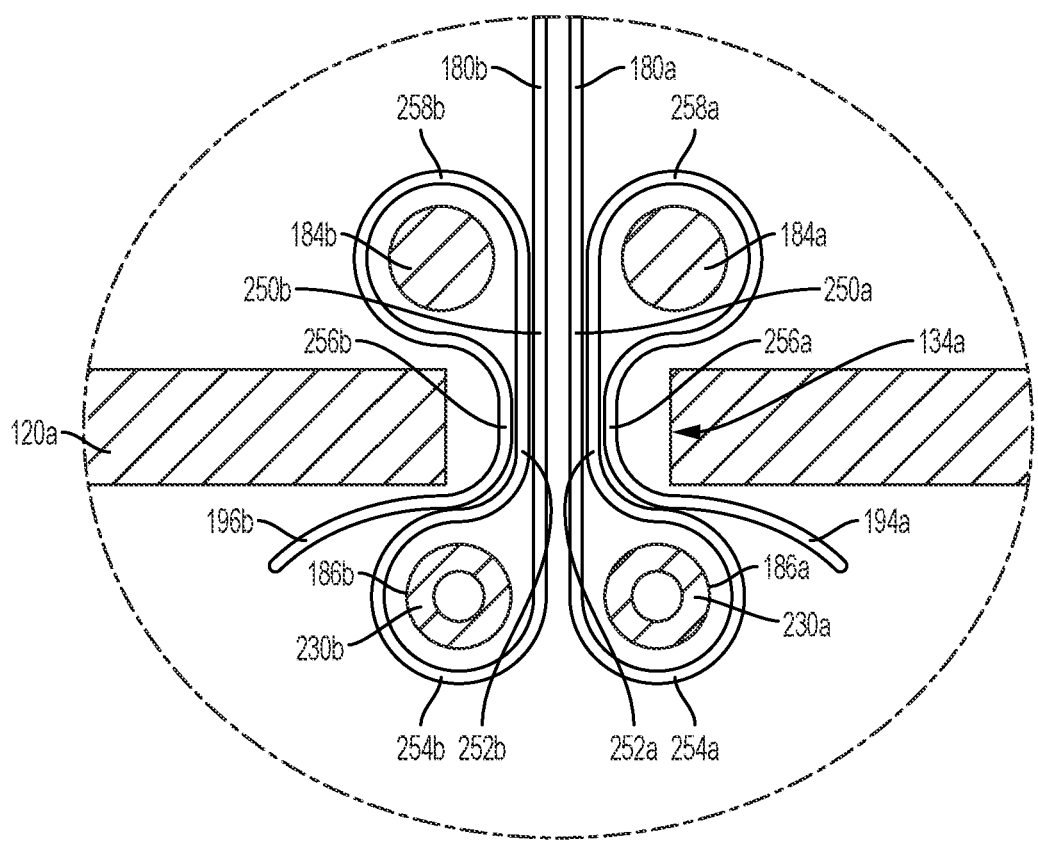
FIG. 9 is a sectional view showing a loop configuration of the prosthetic valve of FIG. 1, according to some embodiments.
Figure 10:
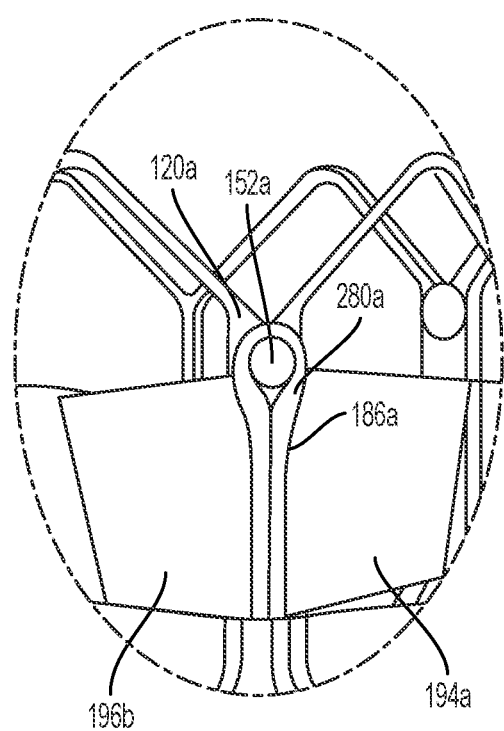
FIG. 10 is an enlarged view of a portion of the prosthetic valve of FIG. 1 during assembly, according to some embodiments.

FIGS. 9 and 10 illustrate attachment of the leaflets 180 to the commissure posts 120 according to some examples. FIG. 9 is a transverse cross-section through the commissure post 120a at the slot 134a and FIG. 10 is an isometric view of the prosthetic valve 100 in the area of the first commissure post 120a. Although relatively sharp corners are shown in FIG. 9 at the slot 134a of the first commissure post 120a, it should be understood that chamfers, rounds, reliefs coatings and other features may be provided to avoid stress concentrations or other wearing of the leaflets 180a, 180b at those slot edges. And, although FIGS. 9 and 10 provide a specific example with regard to the first commissure post 120a, first leaflet 180a, and second leaflet 180, it should be readily understood that similar techniques are employable for attaching the commissure tabs of the remaining leaflets 180 to the remaining commissure posts 120 of the frame 102.

As shown in FIG. 9, the first commissure tab 194a of the first leaflet 180a and the second commissure tab 196b of the second leaflet 180b each pass through the slot 134a of the first commissure post 120a several times, with the first retaining elements 184a, 184b positioned on the inner side 110 of the frame 102, and thus on the inner side of the first commissure post 120a, and the first portion 230a and the second portion 230b of the second retaining element 186a (FIG. 10) on the outer side 112 of the frame 102, and thus the outer side of the first commissure post 120a. As shown, the first retaining elements 184a, 184b secure the first and the second commissure tabs 194a, 196b, respectively, from being pulled outwardly relative to the frame 102. In turn, the first and second portions 230a, 230b of the second retaining element 186a secure the first and the second commissure tabs 194a, 196b, respectively, from being pulled inwardly relative to the frame 102. If desired, sutures, film layers, adhesives, thermal bonding or other features can be used to help secure or otherwise couple the first retaining elements 184a, 184b and/or the second retaining elements 186a, 186b.

As shown, the first commissure tab 194a of the first leaflet 180a defines a first pass 250a through the slot 134a (inside-out relative to the first commissure post 120a) and a second pass 252a through the slot 134a (outside-in relative to the first commissure post 120a) to define a first loop 254a through the slot 134a. The first portion 230a of the second retaining element 186a is positioned within the first loop 254a to form a widened cross-section for the first loop 254a on the outer side 112 of the frame 102. The width of the first loop 254a is selected to resist, or be restrained from, pulling through the slot 134a. The first commissure tab 194a of the first leaflet 180a defines a third pass 256a through the slot 134a (outside-in relative to the first commissure post 120a) to define a second loop 258a passing through the slot 134a. The first retaining element 184a is positioned within the second loop 258a such that the second loop 258a encircles the first retaining element 184a to form a widened cross-section for the second loop 258a on the outer side 112 of the frame 102. The width of the second loop 258a is selected to resist, or be restrained from, pulling through the slot 134a. As shown, the first pass 250a is positioned adjacent the second pass 252a, which is positioned adjacent the third pass 256a within the slot 134a.

As shown, the second commissure tab 196b of the second leaflet 180b defines a first pass 250b through the slot 134a (inside-out relative to the first commissure post 120a) and a second pass 252b through the slot 134a (outside-in relative to the first commissure post 120a) to define a first loop 254b through the slot 134a. The second portion 230b of the second retaining element 186b (FIG. 10) is positioned within the first loop 254b such that the first loop 254b encircles the second retaining element 186b to form a widened cross-section for the first loop 254b on the outer side 112 of the frame 102. The width of the first loop 254b is selected to resist, or be restrained from, pulling through the slot 134a. The second commissure tab 196b of the second leaflet 180b defines a third pass 256b through the slot 134a (outside-in relative to the first commissure post 120a) to define a second loop 258b passing through the slot 134a.

The first retaining element 184b is positioned within the second loop 258b such that the first retaining element 184b is encircled by the second loop 258b to form a widened cross-section for the second loop 258b on the outer side 112 of the frame 102. The width of the second loop 258b is selected to resist, or be restrained from, pulling through the slot 134a. As shown, the first pass 250b is positioned adjacent the second pass 252b, which is positioned adjacent the third pass 256b within the slot 134a.

The first loops 254a,b, are optionally described as outer loops and the second loops 258a,b are optionally described as inner loops. In some examples, one or more of the passes 250a,b, 252a,b, 256a,b are coupled to one another (e.g., by molding, heat sealing/bonding, adhesives, sutures, or other coupling means). Whether coupled or uncoupled (e.g., bonded or unbonded), the various passes can be inserted into the slot 134a with the first retaining elements 184a on the inner side 110 of the frame 102 and the second retaining element 186a outer side of the frame 102 by sliding the first commissure tab 194a and the second commissure tab 196b into the slot 134a through the first end 140a (FIG. 3) of the slot 134a, which is an open end. In some other examples, the first commissure tab 194a and the second commissure tab 196b are threaded through the slot 134a inside-out and outside in to form the first loops 254a,b and the second loops 258a,b (e.g., as opposed being slid upwardly into the first slots 1134a and the second slots 1136a). Although three passes are shown for each of the commissure tabs in FIG. 9, fewer passes (two, where a single loop is desired) or more (e.g., where additional loops are desired) are contemplated.

FIG. 10 shows the second retaining element 186a (which includes the bridge 182a (FIG. 6A) received over the hanging feature 136a (head portion 152a is shown), and in particular behind the head portion 152a within the channel 156a (FIG. 3) formed between the head portion 152a and the frame 102. The second retaining element 186a thus defines a hanging loop 280a for supporting the first leaflet 180a and the second leaflet 180b (FIG. 9) to which the second retaining element 186a is attached. The remaining first and second commissure tabs 194, 196 of the leaflets 180 are secured to and supported from the remaining commissure posts 120. The relatively smooth turns and reinforcement provided by the retaining elements 184, 186 reduce stress concentrations at the commissure posts 120 due to transverse loading of the leaflet construct 104. And, in turn, the axial support provided the hanging loops, similar to hanging loop 280a, provide axial support the leaflet construct 104 and help to reduce axial stress concentrations at the attachment interfaces between the commissure posts 120 and the leaflets 180 (FIG. 5).

Figure 11:
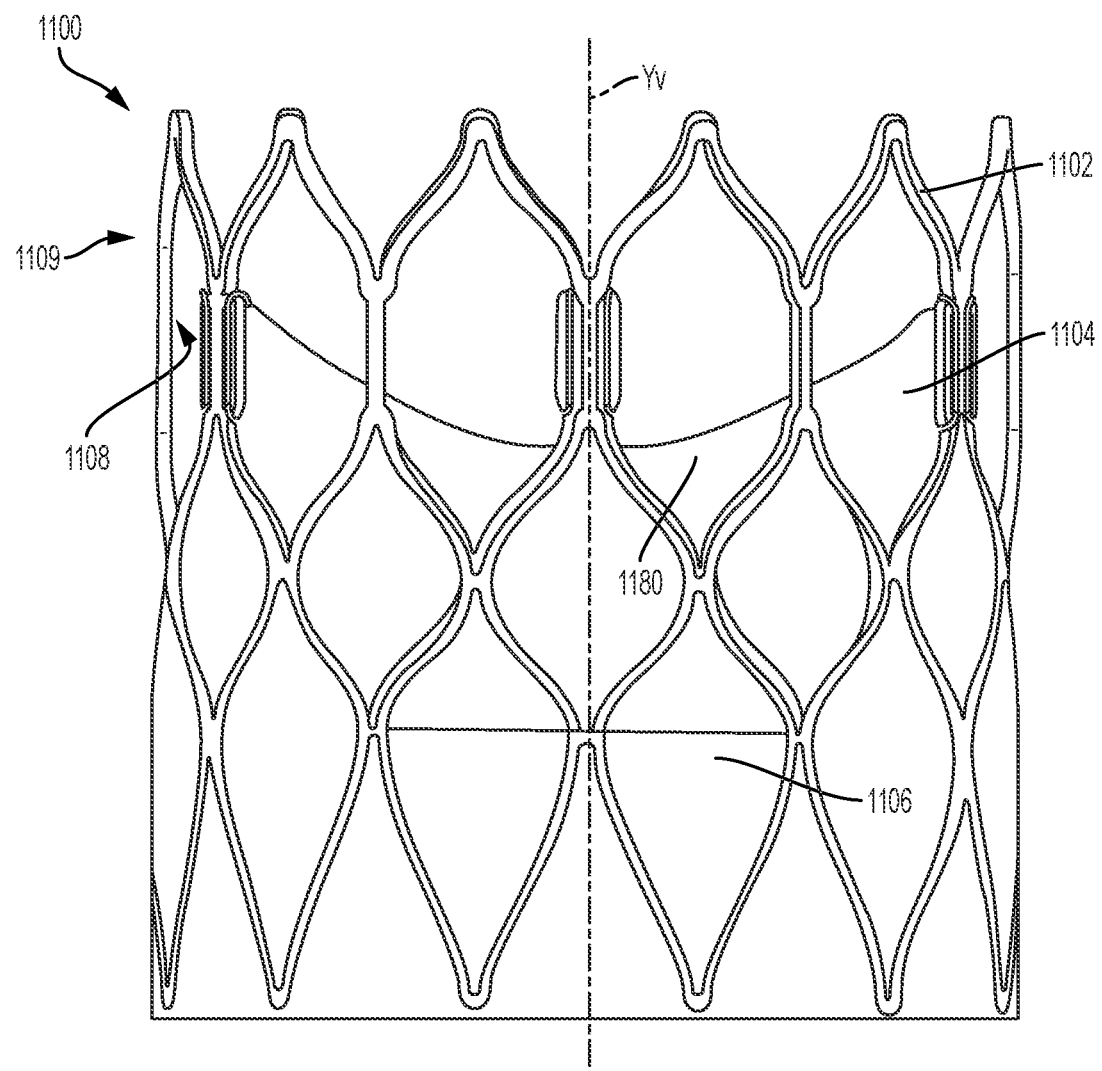
FIG. 11 is a plan view of another prosthetic valve, according to some embodiments.
Figure 11A:
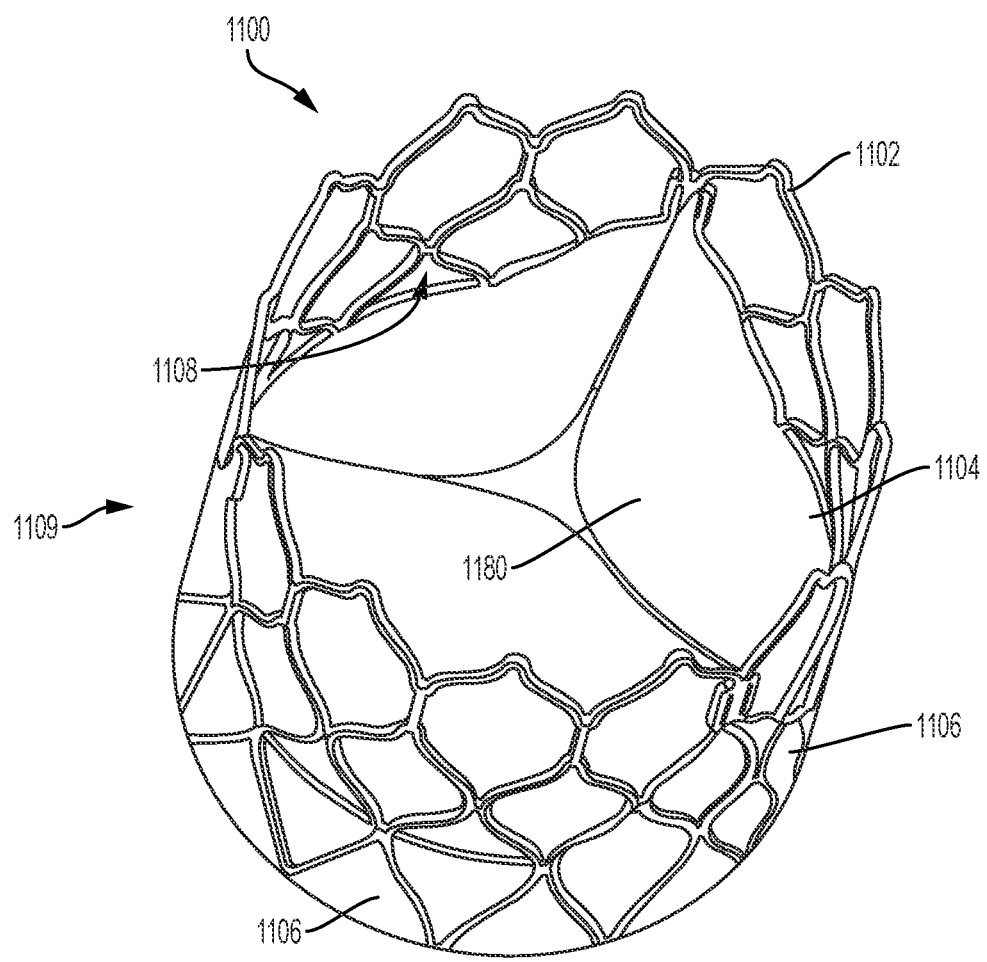
FIG. 11A is an isometric view of the prosthetic valve of FIG. 11, according to some embodiments.

FIG. 11 is a plan view of another prosthetic valve 1100 and FIG. 11A is an isometric view of the prosthetic valve 1100, according to some embodiments. As shown, the prosthetic valve 1100 includes a frame 1102, also described as a frame assembly or leaflet frame, a leaflet construct 1104 including a plurality of leaflets 1180, also described as a leaflet assembly or leaflet module, and an attachment element 1106, which can also be described as an attachment substrate or an attachment treatment. As shown (e.g., FIG. 15), the leaflet construct 1104 may be comprised of a plurality of leaflets 1180 that are formed as individual components and then subsequently assembled to the frame 1102 to form the leaflet construct 1104. The prosthetic valve 1100 can include any of a variety of additional features, such as one or more sealing cuffs, for example. As shown, the prosthetic valve 1100 defines a central longitudinal axis Yv, as well as an inner side 1108 corresponding to a central lumen and an outer side 1109 corresponding to the exterior of the prosthetic valve 1100. The leaflet construct 1104 has three leaflets that come together, and in particular free edges that come together at a coaptation region in a Y-shaped pattern (when viewed from above), to close the prosthetic valve 1100. The prosthetic valve 1100 closes in this fashion when the pressure of the blood on the outflow side is greater than the pressure of the blood on the inflow side of the prosthetic valve 1100. The leaflet free edges of leaflet construct 1104 move apart to open the prosthetic valve 1100 and to let blood flow through the prosthetic valve 1100 from the inflow side when the pressure of the blood on the inflow side of the prosthetic valve 1100 is greater than the pressure on the outflow side of the prosthetic valve 1100.

Figure 12:
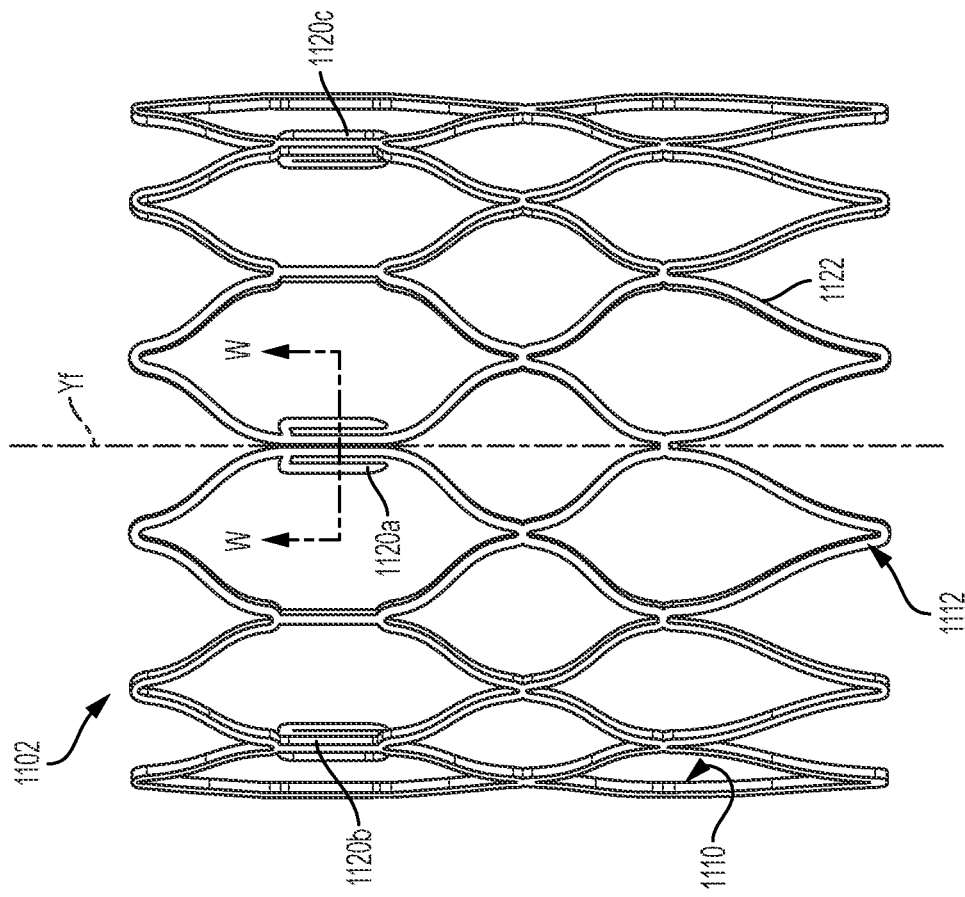
FIG. 12 is a front view of a frame of the prosthetic valve of FIG. 11, according to some embodiments.

FIG. 12 is a perspective view of the frame 1102 of the prosthetic valve 1100, according to some embodiments. In various examples, the frame 1102 serves to operatively support the leaflet construct 1104 in a desired location within the body of a patient (not shown). The frame 1102 is optionally collapsible to a reduced profile, delivery configuration and then expandable (e.g., self-expanding or expanded by the application of an external force, such as a balloon expansion) in situ. As shown in FIG. 12, the frame 1102 is optionally annular, defining a cylinder or cylindrical shape, and has a central longitudinal axis Yf.

Although the frame 1102 generally defines a circular transverse cross-section, it should be understood that any variety of cross-sections (e.g., oval- or rectangular-shaped) cross-sections are also contemplated. The frame 1102 has an inner side 1110 and an outer side 1112 opposite the inner side 1110. The inner side 1110 faces toward the central longitudinal axis Yf, and the outer side 1112 faces outwardly, or away from the central longitudinal axis Yf. As shown, the frame 1102 includes a plurality of commissure posts 1120 and a plurality of frame elements 1122.

The frame 1102 can be etched, cut, laser cut, stamped, three-dimensional printed or wire wound, among other suitable processes. The frame 1102 can comprise, such as, but not limited to, any elastically deformable metallic or polymeric material that is generally biocompatible. The frame 1102 can comprise a shape-memory material, such as nitinol, a nickel-titanium alloy. Other materials suitable for the frame 1102 include, but are not limited to, other titanium alloys, stainless steel, cobalt-nickel alloy, polypropylene, acetyl homopolymer, acetyl copolymer, other alloys or polymers, or any other material that is generally biocompatible having adequate physical and mechanical properties to function as a frame 1102 as described herein.

In some embodiments, the plurality of commissure posts 1120 are spaced from one another, and arranged at desired locations around a circumference of the frame 1102. As shown, the plurality of commissure posts 1120 extend parallel to the central longitudinal axis Yf, although angled configurations (e.g., commissure posts angled inwardly toward the central longitudinal axis Yf or outwardly away from the central longitudinal axis Yf) are also contemplated. Although three commissure posts 1120 are shown, any number of commissure posts are contemplated. The plurality of commissure posts 1120 define circumferentially-adjacent ones, or simply adjacent ones of the plurality of commissure posts 1120 moving about the perimeter of the frame 1102.

Figure 13:
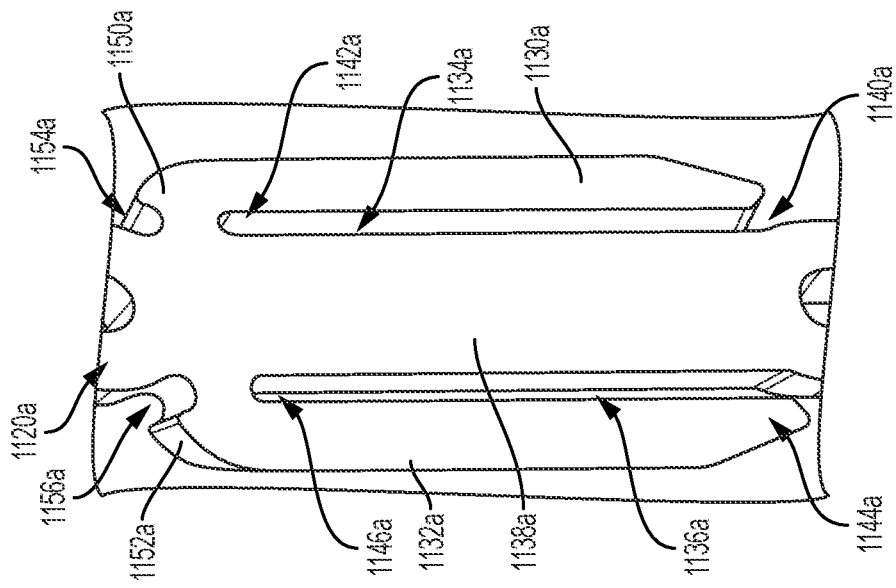
FIG. 13 is an enlarged view of a commissure post of the frame of FIG. 12, according to some embodiments.

As shown in FIG. 12, other than location and orientation, each of the commissure posts 1120 has a similar design, although examples where the commissure posts differ from one another in various respects are also contemplated. Regardless, for ease of understanding, the features of each of the commissure posts 1120 will be described in association with a first commissure post 1120*a*, an enlarged view of which is shown in FIG. 13. The features of the first commissure post 1120*a* will generally be referenced with a numeral followed by an "a." Similar features of a second commissure post may be subsequently referenced with the same numeral as the first commissure post, but followed by a "b." Similar features of a third commissure post may be subsequently referenced with the same numeral as the first commissure post 1120*a*, but followed by a "c." Similarly, when features of each of the commissure posts 1120 are referenced collectively, those features are referenced with the same numeral as identified for the first commissure post 1120*a*, but not followed by a letter.

As shown in FIG. 13, the first commissure post 1120*a*, includes a first leg 1130*a*, a second leg 1132*a*, a first slot 1134*a*, which can also be described as a first post slot, and a second slot 1136*a*, which can also be described as a second post slot. The first slot 1134*a* and the second slot 1136*a* are each located between the first leg 1130*a* and the second leg 1132*a*. As shown, the first commissure post 1120*a* also includes an intermediate leg 1138*a* positioned between the first leg 1130*a* and the second leg 1132*a*. The first commissure post 1120*a* defines the first slot 1134*a* between the first leg 1130*a* and the intermediate leg 1138*a* and the second slot 1136*a* between the second leg 1132*a* and the intermediate leg 1138*a*. The first commissure post 1120*a* has an outer side corresponding to the frame outer side 1112 and a post inner side corresponding to the frame inner side 1110.

As shown, the first leg 1130*a* and the second leg 1132*a* extend longitudinally, or in a longitudinal direction. In some examples, the first leg 1130*a* and the second leg 1132*a* extend in a longitudinal direction that is parallel to the central longitudinal axis Yf (FIG. 12) of the frame 1102. In other examples, the first leg 1130*a* and the second leg 1132*a* extend longitudinally, but at some offset relative to the central longitudinal axis Yf (e.g., angularly offset inwardly, toward the central longitudinal axis Yf, angularly offset transversely relative to the central longitudinal axis Yf, or a combination thereof).

As shown, each of the first slot 1134*a* and the second slot 1136*a* extends through a thickness of the first commissure post 1120*a*, from the inner side 1110 (FIG. 12) of the frame 1102 to the outer side 1112 (FIG. 12) of the frame 1102. The slots 1134*a*, 1136*a* are formed through the frame in a radial direction relative to a central longitudinal axis Yf of the frame 1102 or the slot is formed at an angle to a radial direction relative to the central longitudinal axis Yf of the frame 1102. In various examples, one or both of the first slot 1134*a* and the second slot 1136*a* extend in a longitudinal direction that is parallel to the central longitudinal axis Yf (FIG. 12) of the frame 1102. In other examples, one or both of the first slot 1134*a* and the second slot 1136*a* extend longitudinally, but at some offset relative to the central longitudinal axis Yf (e.g., angularly offset inwardly, toward the central longitudinal axis Yf, angularly offset transversely relative to the central longitudinal axis Yf, or a combination thereof). As shown, one or both of the first slot 1134*a* and the second slot 1136*a* are elongate in shape, with lengths, or heights, much greater than their widths (e.g., more than 2×, 5×, 10×, 20×, or 30×, although a variety of dimensions are suitable).

In some examples, the first slot 1134*a* extends from a first end 1140*a* to a second end 1142*a* and the second slot 1136*a* extends from a first end 1144*a* to a second end 1146*a*. As shown, the first ends 1140*a*, 1144*a* are open and the second ends 1142*a*, 1146*a* are closed. For example, the first ends 1140*a*, 1144*a* are "open" in the sense that it opens to a much wider area in the frame 1102 (e.g., more than 5×, 10×, or 20×), whereas the second ends 1142*a*, 1146*a* are "closed" in the sense that it terminates at the width of the first slot 1134*a* and the second slot 1136*a*. The widths of the first slot 1134*a* and the second slot 1136*a* are generally selected to allow a desired number of passes or loops of leaflet material through the first slot 1134*a* and the second slot 1136*a*.

In some embodiments, the first commissure post 1120*a* defines a first hanging feature 1150*a*, also described as a protuberance, hook, or projection, and a second hanging feature 1152*a*, also described as a protuberance, hook, or projection. Each of the first and second hanging features 1150*a*, 1152*a* is optionally described as a hanger, shoulder, pin, or hook, for example. The first hanging feature 1150*a* optionally projects longitudinally from the first leg 1130*a* (e.g., parallel to the longitudinal axis Yf of the frame 1102). The second hanging feature 1152*a* optionally projects longitudinally from the second leg 1132*a* (e.g., parallel to the longitudinal axis Yf of the frame 1102). The first commissure post 1120*a* optionally defines a first channel 1154*a* between the first hanging feature 1150*a* and the intermediate leg 1138*a*. The first commissure post 1120*a* also optionally defines a second channel 1156*a* between the second hanging feature 1152*a* and the intermediate leg 1138*a*. The depths and widths of the channels 1154*a*, 1156*a* are generally selected to receive and retain filaments or other desired portions of the leaflet construct 1104 for axially supporting the leaflet construct 1104. As shown, the hanging features 1150*a*, 1152*a* are each located longitudinally-adjacent the second ends 1142*a*, 1146*a* of the slots 1134*a*, 1136*a* and generally in alignment with the first slot 1134*a* and the second slot 1136*a*. In other examples, the hanging features 1150*a*, 1152*a* are offset from the first slot 1134*a* and the second slot 1136*a* (e.g., laterally/circumferentially).

Figure 14:
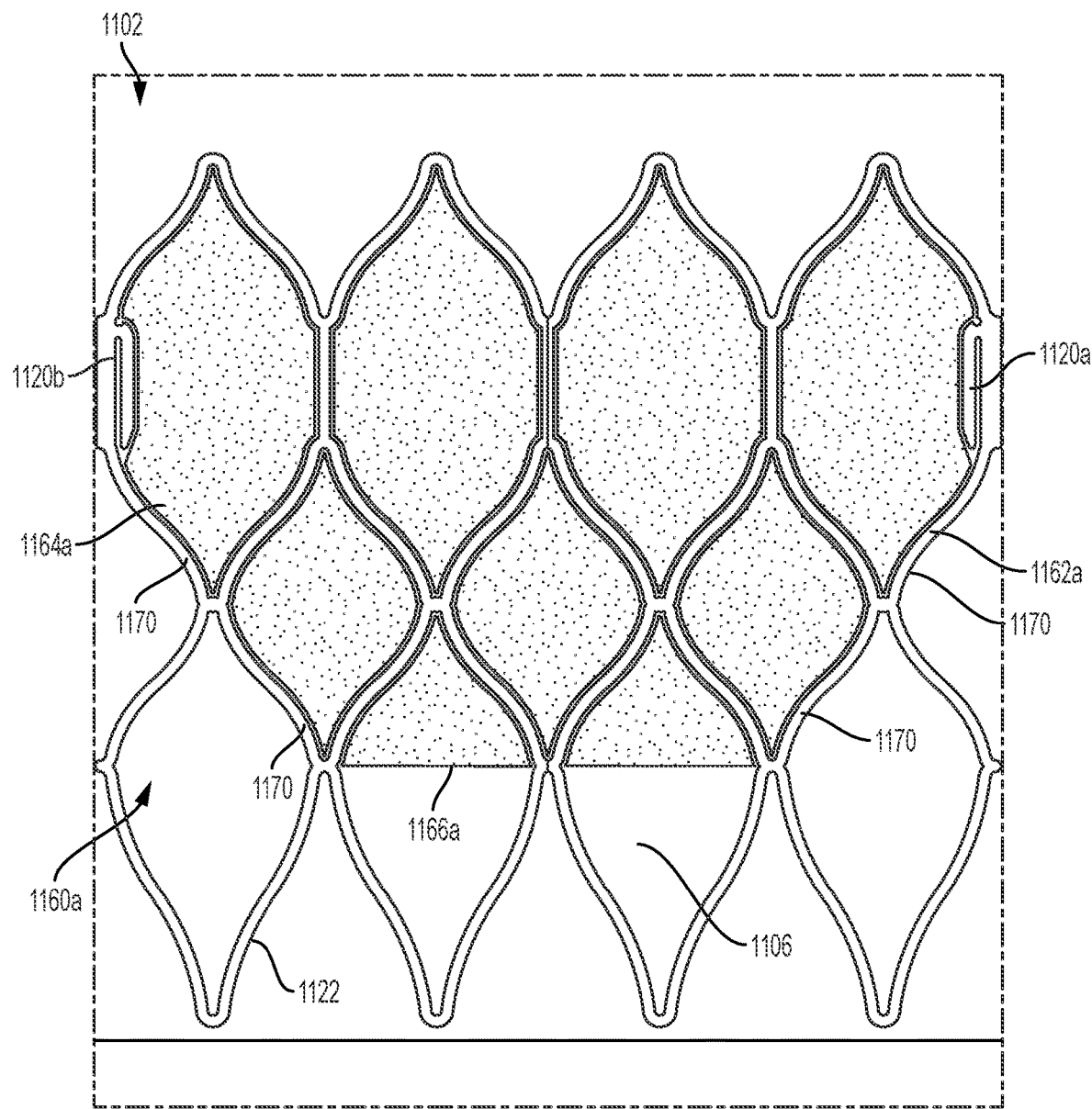
FIG. 14 is a flat, schematic view of a portion of the frame of FIG. 12, according to some embodiments.

FIG. 14 is an enlarged, flattened view of a portion of the frame 1102 between two adjacent commissure posts 1120, according to some embodiments. Similar portions of the frame 1102 are defined between each of the adjacent commissure posts 1120, according to some embodiments. In FIG. 14, the portion of the frame 1102 is represented in a flattened form for ease of illustration, although it should be understood that the frame 1102 is three-dimensional and generally annular. As shown in FIG. 14, the first commissure post 1120*a* is located at a first side of the portion of the frame 1102 and a second commissure post 1120*b* of the plurality of commissure posts 1120 is located at a second side of the portion of the frame 1102 shown in FIG. 4. In particular, the frame 1102 defines a first leaflet attachment region 1160*a* between the first commissure post 1120*a* and the second commissure post 1120*b*, as well as leaflet attachment regions 1160 between the remaining commissure posts 1120. The first leaflet attachment region 1160*a* defines a first side 1162*a*, a second side 1164*a*, and a base 1166*a*. Similar leaflet attachment regions 1160 are defined between each of the adjacent commissure posts 1120, according to some embodiments.

In some embodiments, the frame elements 1122 of the frame 1102 include a plurality of leaflet attachment frame elements 1170, or simply leaflet attachment elements, that define the leaflet attachment regions, including the first leaflet attachment region 1160*a* shown in FIG. 14. The leaflet attachment frame elements 1170 are arranged to support the leaflet construct 1104 and to help define a shape of a leaflet of the leaflet construct 1104, where that leaflet will project from the first leaflet attachment region 1160*a*. In the example shown in FIG. 12, the frame 1102 defines three sets of the leaflet attachment frame elements 1170 that each generally follows the shape of an outline of a leaflet of the leaflet construct 1104. In different terms, the leaflet attachment frame elements 1170 optionally support leaflets around the leaflet perimeters except at the free edges.

Figure 15:
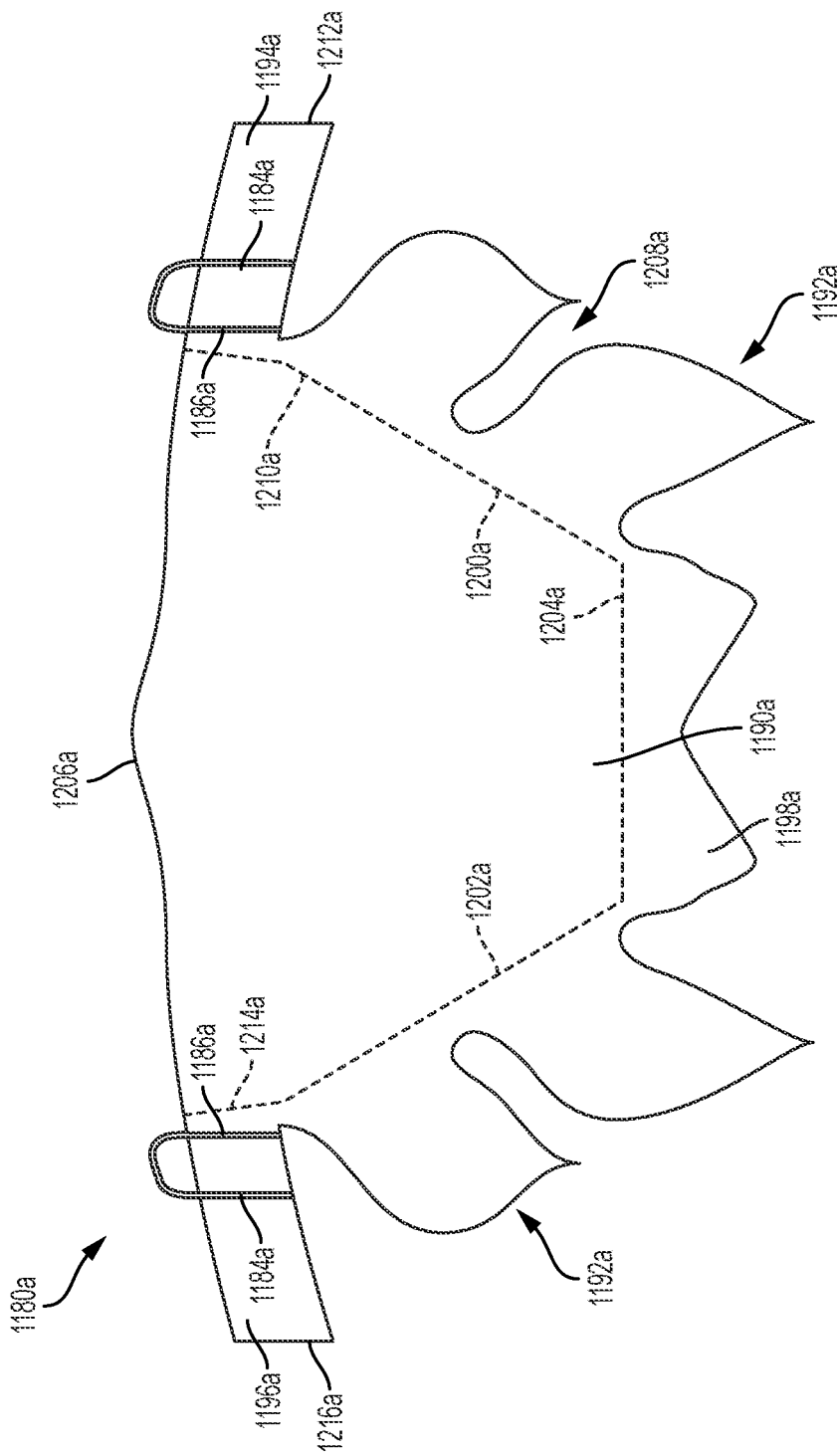
FIG. 15 is a view of a leaflet pattern of the prosthetic valve of FIG. 11, according to some embodiments.

As shown in FIG. 11, the leaflet construct 1104 includes a plurality of leaflets 1180. FIG. 15 shows a first leaflet 1180a of a plurality of leaflets 1180 (FIG. 11) from a flattened, plan view prior to assembly with the frame 1102. This flattened plan view can also be described as a cut pattern, or simply a leaflet pattern. From FIG. 11, for example, it should be understood that the leaflet construct 1104 is folded and turned into a cylindrical shape when assembled to the frame 1102, with each of the plurality of leaflets 1180 being attached circumferentially about the frame 1102. As should be understood from FIG. 15, the plurality of leaflets 1180 are optionally formed as separate components, which are then separately assembled to the frame 1102. It should also be understood, however, that similar to the leaflet construct 104, the leaflet construct 1104 optionally includes a plurality of bridges, or bridge regions (e.g. such as bridges 182), interconnecting circumferentially-adjacent leaflets 1180. In such embodiments, the leaflet pattern defines a connected and continuous (e.g., contiguous) annular ring including the plurality of leaflets and bridges between each of the plurality of leaflets. As shown, the plurality of leaflets 1180 are spaced from one another, and arranged, or otherwise distributed at desired locations around a circumference of the leaflet construct 1104.

Although three leaflets 1180 are shown in FIG. 11, any number of leaflets is contemplated. The plurality of leaflets 1180 define circumferentially-adjacent ones, or simply adjacent ones of the plurality of leaflets 1180 moving about the circumference of the leaflet construct 1104. The leaflet construct 1104 can be formed in a variety of manners, including cutting a cylinder of polymer material into a desired shape, cutting a sheet of polymer material into a desired shape, and/or molding (e.g., compression or injection molding) the leaflet construct 1104 with a desired shape.

According to various examples, other than location and orientation, each of the plurality of leaflets 1180 has a similar design, although examples where the leaflets differ from one another in various respects are also contemplated. Regardless, for ease of understanding, the features of each of the leaflets 1180 will be described in association with a first leaflet 1180a. The features of the first leaflet 1180a will generally be referenced with a numeral followed by an "a." Similar features of a second leaflet may be subsequently referenced with the same numeral as the first leaflet, but followed by a "b." Similar features of a third leaflet may be subsequently referenced with the same numeral as the first leaflet 1180a, but followed by a "c." Similarly, when features of each of the leaflets are referenced collectively, those features are referenced with the same numeral, but not followed by a letter. Similarly, when features of each of the leaflets 1180 are referenced collectively, those features are referenced with the same numeral, but not followed by a letter.

As shown in FIG. 15, the first leaflet 1180a includes a plurality of first retaining elements 1184a and a plurality of second retaining elements 1186a, where each of the leaflets 1180 optionally includes a similar first retaining element 1184 and second retaining elements 1186. The first plurality of retaining elements 1184a and the second plurality of retaining elements 1186a are optionally molded, adhered and/or heat bonded, or otherwise coupled to the leaflet construct 1104 (FIG. 11) as desired.

As indicated on FIG. 15, the first leaflet 1180a optionally includes a body portion 1190a, a plurality of attachment tabs 1192a extending from the body portion 1190a, a first commissure tab 1194a extending from the body portion 1190a, and a second commissure tab 1196a extending from the body portion 1190a.

The body portion 1190a, also described as a leaflet belly, or belly portion, is bounded in broken lines for understanding purposes. The body portion 1190a of the first leaflet 1180a is the moving portion of the first leaflet 1180a in the prosthetic valve 1100 (FIG. 11). It should be appreciated that when assembled to the frame 1102, the boundaries of the body portion 1190a are defined and the body portion 1190a takes on a three dimensional shape, rather than the flat shape shown in FIG. 15. As such, the broken lines are provided for general visualization purposes of the body portion 1190a. In various examples, the shape of the body portion 1190a is generally dictated by the lines, or areas of attachment to the frame 1102. The edges of the body portion 1190a generally correspond to fold lines where the attachment tabs 1192a and first commissure tab 1194a and the second commissure tab 1196a are secured to the frame 1102. As will be described below, the leaflet construct 1104 may be attached to the frame 1102 using attachment element 1106 (FIG. 11), which in turn, may contribute to shape defined by the leaflet attachment regions 1160 and the ultimate shape of the body portion 1190a.

As shown in FIG. 15, the body portion 1190a of the first leaflet 1180a has the general shape of an isosceles trapezoid. Regardless of the exact shape, the body portion 1190a generally has a first side 1200a, a second side 1202a, a leaflet base 1204a, and a free edge 1206a opposite the leaflet base 1204a for coaptating with other leaflets 1180. In general terms, the shape of the body portion 1190a corresponds to the sides and base of the first leaflet attachment region 1160a (FIG. 14). As shown, the two sides 1200a, 1202a diverge from the leaflet base 1204a, and the leaflet base 1204a will be substantially straight in a transverse plane relative to the central longitudinal axis Yf of the frame 1102. In different terms, leaflet base 1204a is perpendicular to the central longitudinal axis Yf of the frame 1102 following assembly.

Although the body portion 1190a is shown to take on the general shape of an isosceles trapezoid, any number of shapes is contemplated, and the body portion 1190a need not be trapezoidal in overall appearance. For example, the body portion 1190a may include a central region that defines a shape substantially that of an isosceles trapezoid, with side regions on each side that have a shape substantially that of a triangle. In still other embodiments, the body portion 1190a may outline a shape that can be described as U-shaped or a V-shapes, depending on the geometric outline defined by the first leaflet attachment region 1160a (FIG. 14).

The first leaflet 1180a generally defines a fold over portion 1198a, also described as a fold over region, outside of the body portion 1190a, as demarcated by the broken line in FIG. 15. The fold over portion 1198a of the first leaflet 1180a is the portion that is used to secure the first leaflet 1180a to the frame 1102, where the remaining leaflets 1180 optionally include similar features for securing to the frame 1102. The leaflet attachment frame elements 1170 (FIG. 14) fit into a fold that is formed between the body portion 1190a and the fold over portion 1198a. In general terms, the leaflets 1180 extend radially inward from the frame 1102 when coupled to the frame 1102. The body portion of each leaflet 1180 includes enough material between the commissure posts 1120 of the frame 1102 so that the leaflet free edges of the three leaflet body portions can come together or coapt in the interior of the prosthetic valve 1100 to close the prosthetic valve 1100 as shown in FIG. 11.

As shown, the plurality of attachment tabs 1192a located in the fold over portion 1198a are positioned about a perimeter of the body portion 1190a and are separated from one another by openings 1208a for receiving frame elements 1122 (e.g., leaflet attachment frame elements 1170) of the frame 1102. As shown, one or more of the plurality of attachment tabs 1192a optionally includes apertures (not shown) through the thickness of the attachment tabs 1192a. The apertures may assist with securing the tabs 1192a to the frame 1102 (e.g., directly or via the attachment element 1106) using molding, adhesives and/or bonding (e.g., to provide additional surface area for adhesion/bonding), fastening elements (e.g., holes for sutures), or combinations thereof.

In various examples, the first commissure tab 1194a and the second commissure tab 1196a assist with securing the first leaflet 1180a to the first commissure post 1120a and second commissure post 1120b (FIG. 2). As shown in FIG. 15, the first commissure tab 1194a extends from the first side 1200a of the body portion 1190a and the second commissure tab 1196a extends from a second side 1202a of the body portion 1190a. The first commissure tab 1194a extends from a first end 1210a, also described as a leaflet end, to a terminal end 1212a. Similarly, the second commissure tab 1196a extends from a first end 1214a to a terminal end 1216a. The first commissure tab 1194a and the second commissure tab 1196a are shown as generally rectangular in shape, with a constant width, although tapers (e.g., toward the terminal ends 1212a, 1216a) are also contemplated.

Figure 23:
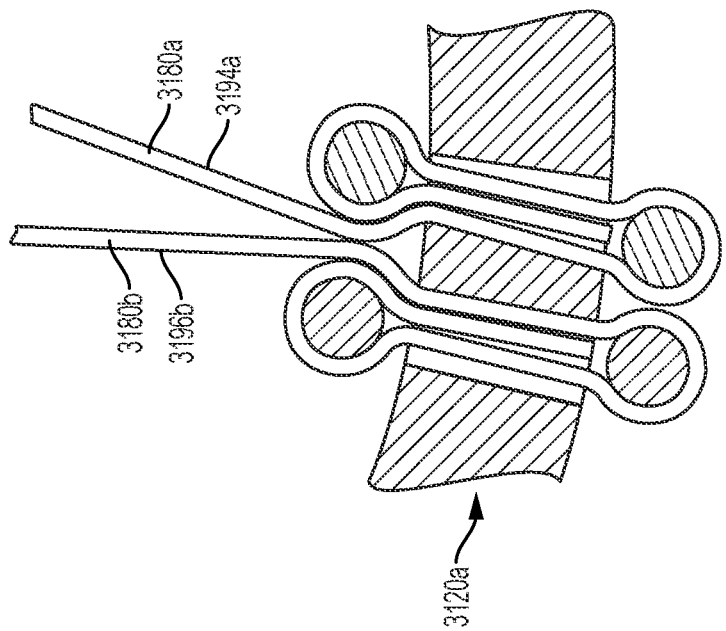
FIGS. 22 and 23 show features of another attachment arrangement between leaflets and a commissure post of a prosthetic valve, according to some embodiments.
Figure 24:
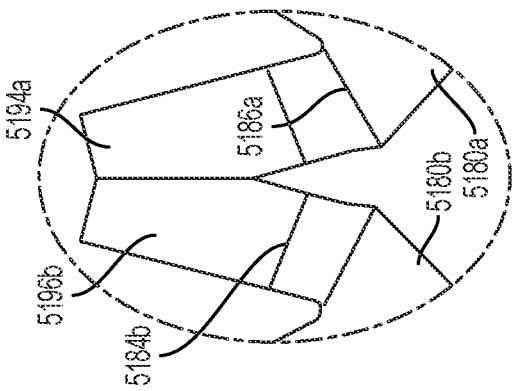
FIGS. 24-28 show various retaining element arrangements usable for leaflets in attachment arrangements between leaflets and commissure posts, according to some embodiments.

Though not shown in FIG. 15, where included (e.g., as shown in FIGS. 23 and 24) bridges extend between and interconnect the plurality of leaflets 1180. For example, each of the bridges is optionally substantially similar and interconnects, or otherwise extends between adjacent leaflets 1180. In such examples, it is also contemplated that, when the leaflet construct 1104 is folded into a cylindrical shape and the leaflet construct 1104 is folded onto frame 1102, the bridges define loops for attachment to the commissure posts 1120.

As shown, the first leaflet 1180a includes first retaining elements 1184a that are located on each of the first commissure tab 1194a and the second commissure tab 1196a. Similarly to those of the first leaflet 180a and the second leaflet 180b of the leaflet construct 104 (FIG. 5), the first retaining elements 1184 of the respective leaflets 1180 are separate and discontinuous from one another (in different terms, they are not contiguous). As shown, the first leaflet 1180a also includes second retaining elements 1186a that are located on each of the first commissure tab 1194a and the second commissure tab 1196a. As shown, the first retaining elements 1184a and the second retaining elements 1186a of the first commissure tab 1194a are optionally connected and continuous with one another (e.g., contiguous) and are distinct and not connected to another one of the leaflets 1180. Similarly, the first retaining elements 1184a and the second retaining elements 1186a of the second commissure tab 1196a are also optionally connected and continuous with one another (e.g., contiguous) and are distinct and not connected to another one of the leaflets 1180. In other examples (e.g., FIGS. 23 and 26), connected and continuous (e.g., contiguous) retaining elements between adjacent leaflets 1180 are contemplated.

In some examples, the first retaining elements 1184a are spaced apart from their adjacent second retaining elements 1186a a distance at least as wide as the thickness of a corresponding commissure post 1120 (e.g., 1120a) as measured from the inner side 1110 to the outer side 1112 of the frame 1102.

As previously referenced, the various retaining elements can take a variety of forms. In some examples, one or both of the first retaining elements 1184, 1186 are formed as beads of material and/or fibers (e.g., coated fibers) on the commissure tabs of the leaflets 1180. The various retaining elements are optionally molded, adhered and/or bonded to the underlying material of the leaflets 1180, such as by thermal bonding.

As will be described below, in some examples, the second retaining elements 1186 (FIG. 15) are located adjacent the slots 1134, 1136 (FIG. 13) at the outer side 1112 (FIG. 11) and the first retaining elements 1184 (FIG. 15) are located adjacent the slots 1134, 1136 at the inner side 1110 of the frame 1102 (FIG. 12). The second retaining elements 1186 are optionally used to help prevent the first and second commissure tabs 1194, 1196 (FIG. 15) from pulling inwardly through the slots 1134, 1136, wherein the first retaining elements 1184 are optionally used to help prevent the commissure tabs 1194, 1196 from pulling outwardly through the slots 1134, 1136 to the outer side 1112 of the frame 1102.

The first retaining elements 1184 and the second retaining elements 1186 can be formed similarly to, and from any of the materials described in association with the first retaining elements 1184 and the second retaining elements 1186.

Figure 16:
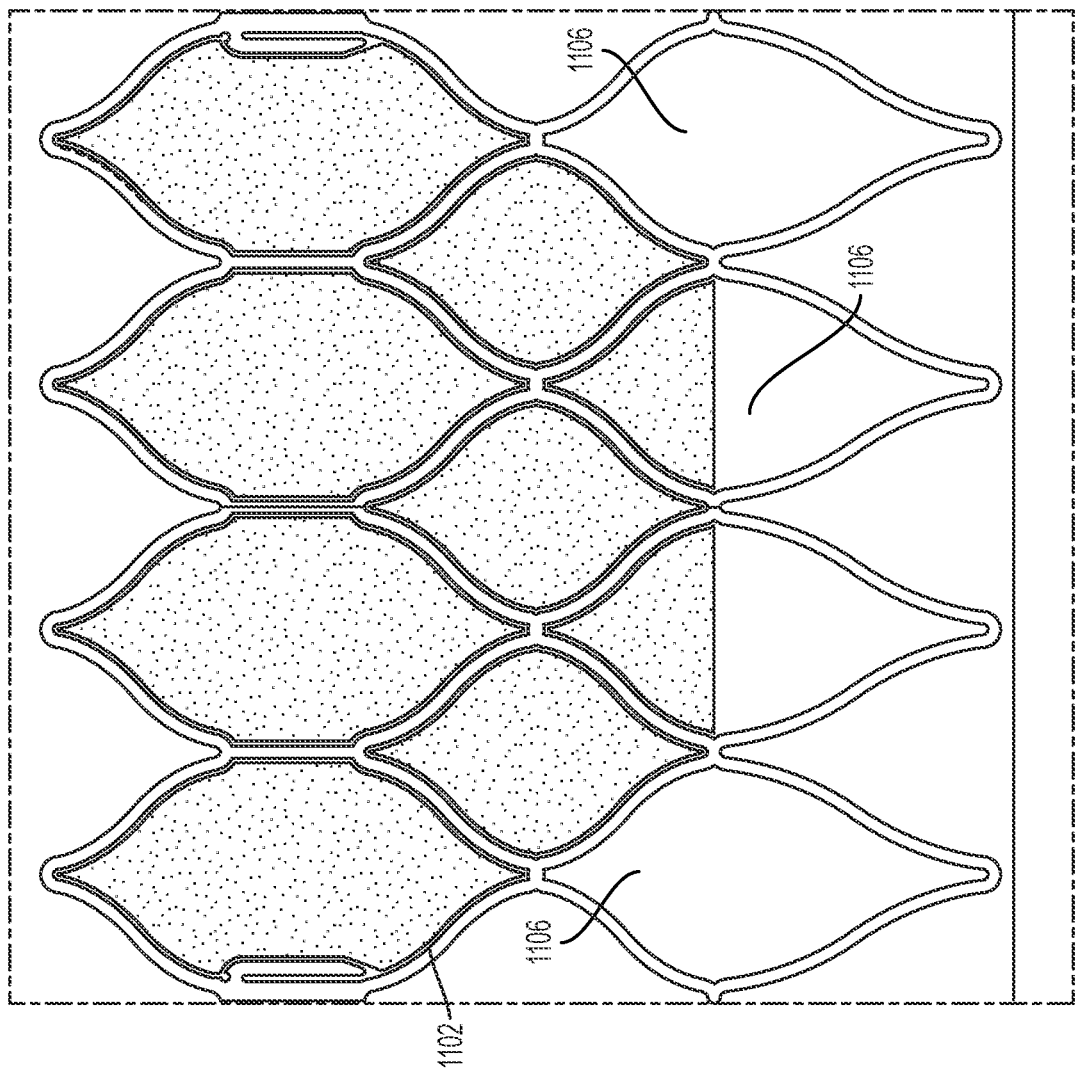
FIG. 16 is a flat, schematic view of a portion of the frame and an attachment element of the prosthetic valve of FIG. 11, according to some embodiments.

FIG. 16 shows a portion of the frame 1102 and attachment element 1106. As previously referenced, the prosthetic valve 1100 optionally includes attachment element 1106, which can also be described as an attachment substrate or an attachment treatment. The shaded area in FIG. 16 represents locations where the attachment element 1106 is not present. For example, the attachment element 1106 is optionally one or more layers of material applied to the frame material. If desired, the openings, or gray areas in the attachment element 1106 are optionally formed via laser cutting (e.g., where the attachment element is applied to the frame 1102 as part of a tape wrapping process. Several locations of the attachment element 1106 are marked on FIG. 7 for ease of understanding. The attachment element 1106 is optionally one or more layers of material attached to the frame 1102. In some examples, the outer side 1112 of the frame 1102 is covered with the attachment element 1106, which is in the form of one or more layers of film material. One or more portions of the leaflet construct 1104 can then be attached to the attachment element 1106, thereby helping to define the shapes of the leaflets 1180.

Figure 17:
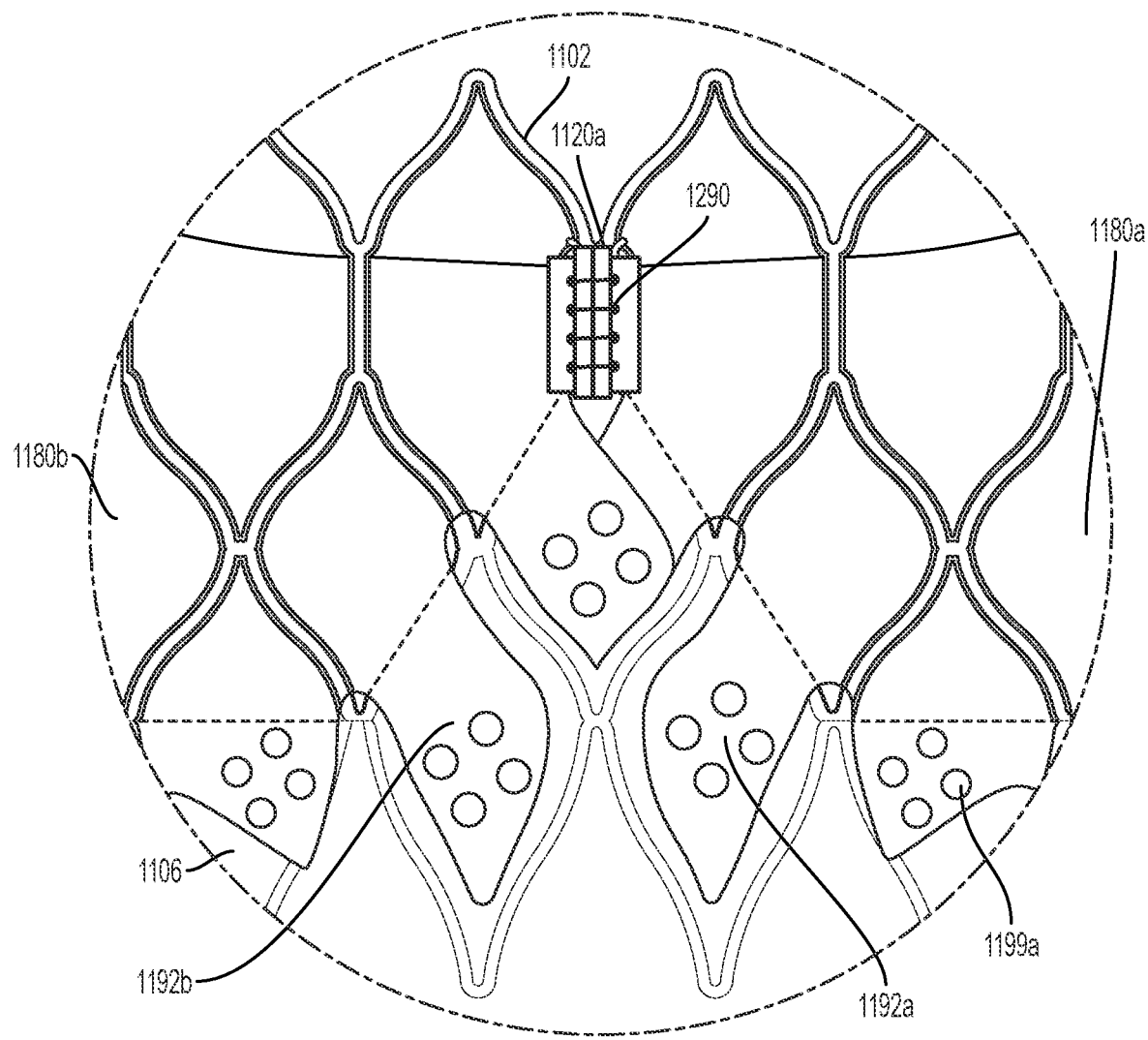
FIG. 17 is an overlay view for understanding assembly of the prosthetic valve of FIG. 11, according to some embodiments.

FIG. 17 shows an overlay of portions of the prosthetic valve 1100 illustrating parts of the frame 1102, first leaflet 1180a and the second leaflet 1180b of the leaflet construct 1104, and the attachment element 1106 in an area of the first commissure post 1120a, for understanding of assembly thereof, where similar concepts apply in assembling the remaining leaflets 1180 to the frame 1102. As referenced above, the leaflet construct 1104 (FIG. 11) is attached to the frame 1102 and/or attachment element 1106 using fold over portions, such as the fold over portion 1198a (FIG. 15) of the first leaflet 1180a. Attachment tabs, such as the attachment tabs 1192a, 1192b of the first leaflet 1180a and the second leaflet 1180b are received over portions of the frame 1102 and/or attachment element 1106 and attached thereto to attach the leaflet construct 1104 to the frame. As should be understood, one or more of the attachment tabs 1192a, 1192b may be folded to the attachment element 1106, rather than the frame 1102. For example, the lowermost attachment tab 1192a may be folded to a relatively flat area at the bottom of the attachment element 1106 (not shown), to define a relatively flat base corresponding to that shown for the body portion 1190a in FIG. 15. In different terms, the attachment tabs do not necessarily have to follow the geometry of the frame 1102, but can be folded or otherwise attached to follow a geometry separate from that of the frame 1102, such as that defined by the attachment element 1106, for example.

The fold over portions can be secured in place using adhesives, sutures, sintering, or by other methods as desired. In some examples, apertures, such as the apertures 1199a are used to assist with coupling (e.g., molding, adhering and/or bonding) and/or to assist with aligning the attachment tabs at their proper positions.

Figure 18:
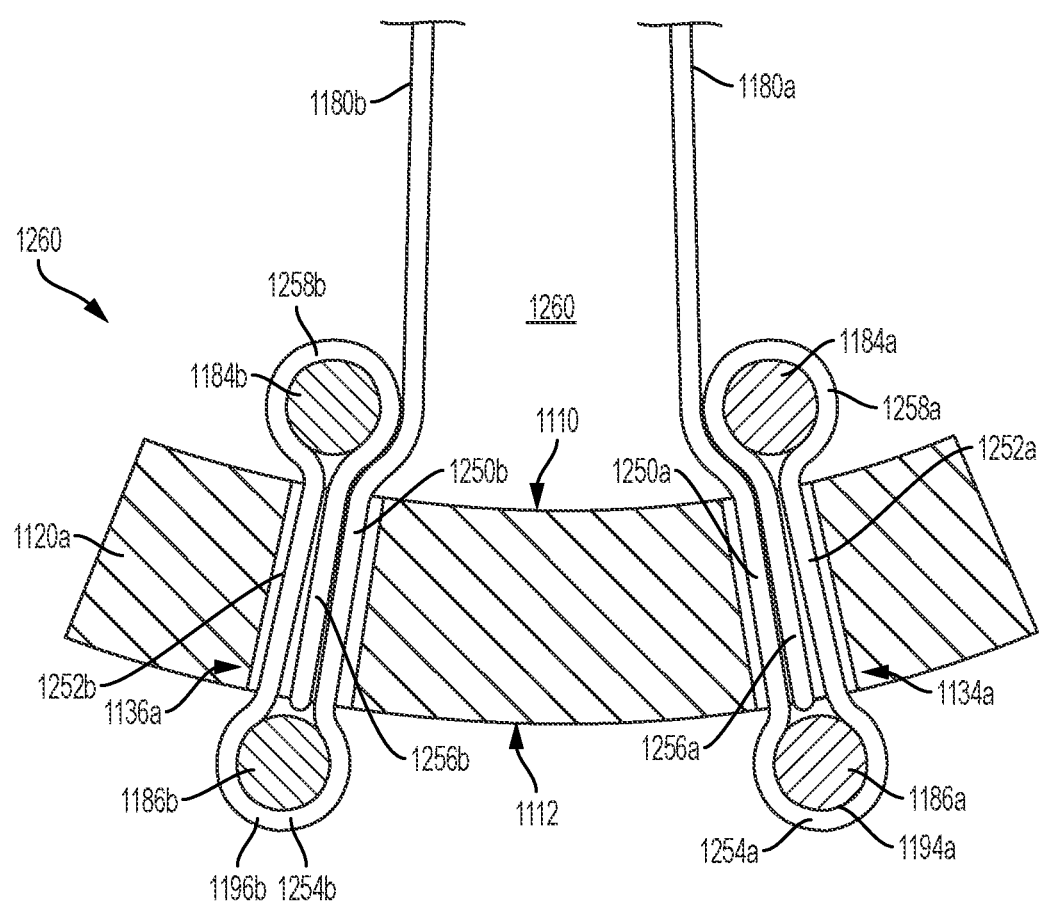
FIG. 18 is a transverse cross-section of the prosthetic valve of FIG. 11 at a commissure post of the prosthetic valve taken along line W-W on FIG. 12, with portions of the prosthetic valve removed for ease of illustration, according to some embodiments.
Figure 20:
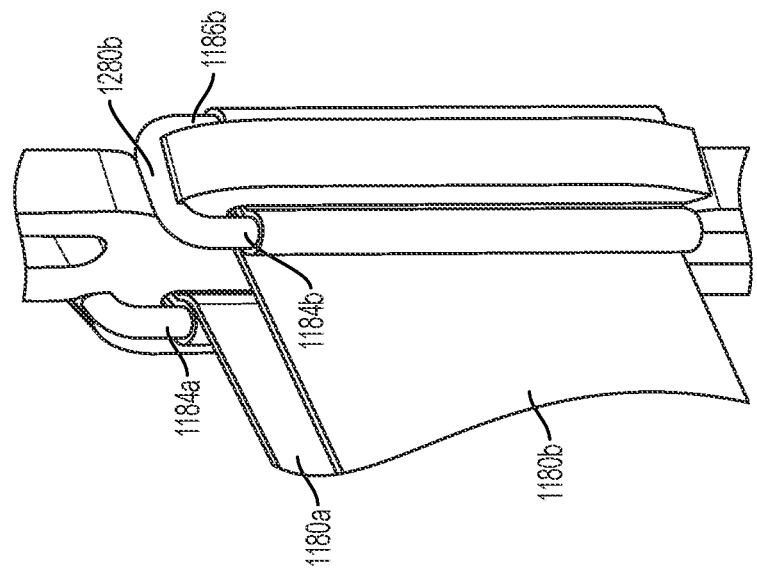
FIGS. 19 and 20 are isometric views of a commissure post of the prosthetic valve, with portions of the prosthetic valve removed for ease of illustration, according to some embodiments.
Figure 19:
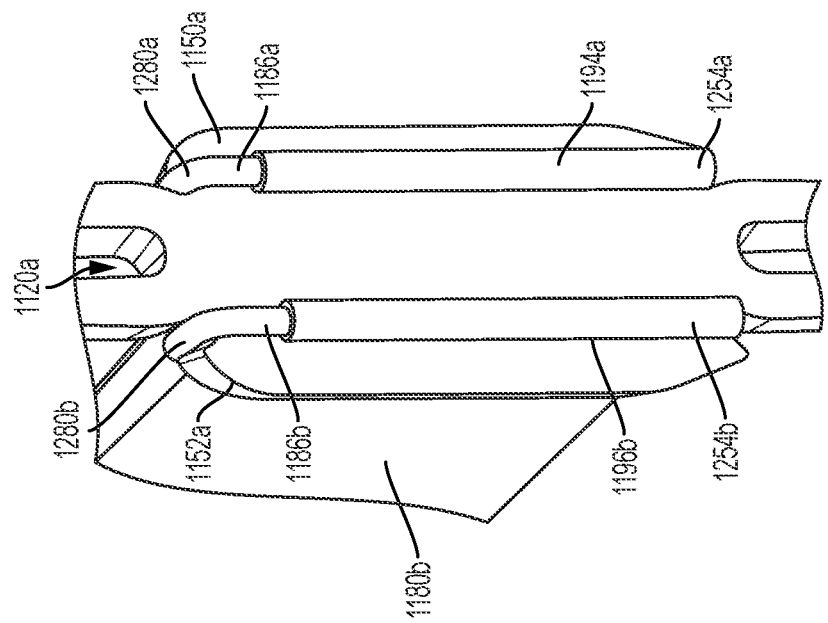

FIGS. 18 to 20 illustrate attachment of the leaflets 1180 to the commissure posts 1120 according to some examples. FIG. 18 is a transverse cross-section through the first commissure post 1120a at the first slot 1134a and the second slot 1136a. Although relatively sharp corners are shown in FIG. 18 at the first and second slots 1134a, 1136a of the first commissure post 1120a, it should be understood that chamfers, rounds, reliefs coatings and other features may be provided to avoid stress concentrations or other wearing of the first and second leaflets 1180a, 1180b at those slot edges. FIGS. 19 and 20 are isometric view of the prosthetic valve 1100 in the area of the first commissure post 1120a. In this regard, a specific example with regard to the first commissure post 1120a, first leaflet 1180a, and second leaflet 1180b is provided, although and as previously mentioned, it should be readily understood that similar techniques are employable for attaching the remaining commissure tabs of the leaflets 1180 to the remaining commissure posts 1120 of the frame 1102.

As shown in FIG. 18, the first commissure tab 1194a of the first leaflet 1180a extends through the first slot 1134a and the second commissure tab 1196b of the second leaflet 1180b extends through the second slot 1136a of the first commissure post 1120a several times, with the first retaining elements 1184a, 1184b positioned on the inner side 1110 of the frame 1102, and thus on the inner side of the first commissure post 1120a. The second retaining elements 1186a, 1186b are shown on the outer side 1112 of the frame 1102, and thus on the outer side of the first commissure post 1120a. As shown, the first retaining elements 1184a, 1184b secure the first and second commissure tabs 1194a, 1196b, respectively, from being pulled outwardly relative to the frame 1102. In turn, the second retaining elements 1186a, 1186b secure the commissure tabs 1194a, 1196b, respectively, from being pulled inwardly relative to the frame 1102. For example, cross-sectional areas of the first and second retaining elements 1184, 1186 and portions of the commissure tabs 1194, 1196 looped over them are greater than the widths of the slots 1134.

As shown, the first commissure tab 1194a of the first leaflet 1180a defines a first pass 1250a through the first slot 1134a (inside-out relative to the first commissure post 1120a) and a second pass 1252a through the first slot 1134a (outside-in relative to the first commissure post 120a) to define a first loop 1254a through the first slot 1134a. The second retaining element 1186a is positioned within the first loop 1254a such that the second retaining element 1186a is encircled to form a widened cross-section for the first loop 1254a on the outer side 1112 of the frame 1102. The width of the first loop 1254a is selected to resist, or be restrained from, pulling through the first slot 1134a. The first commissure tab 1194a of the first leaflet 1180a defines a third pass 1256a through the first slot 1134a (inside-out relative to the first commissure post 1120a) to define a second loop 1258a passing through the first slot 1134a. The first retaining element 1184a is positioned within the second loop 1258a to encircle the first retaining element 1184a and form a widened cross-section for the second loop 1258a on the outer side 1112 of the frame 1102. The width of the second loop 1258a is selected to resist, or be restrained from, pulling through the first slot 1134a. As shown, the first pass 1250a is positioned adjacent, and opposite the second pass 1252a, and adjacent the third pass 1256a, with the third pass 1256a between the first pass 1250a and the second pass 1252a within the first slot 1134a.

As shown, the second commissure tab 1196b of the second leaflet 1180b defines a first pass 1250b through the second slot 1136a (inside-out relative to the first commissure post 1120a) and a second pass 1252b through the second slot 1136a (outside-in relative to the first commissure post 1120a) to define a first loop 1254b through the second slot 1136a. The second retaining element 1186b is positioned within the first loop 1254b to encircle the second retaining element 1186b and form a widened cross-section for the first loop 1254b on the outer side 1112 of the frame 1102. The width of the first loop 1254b is selected to resist, or be restrained from, pulling through the second slot 1136a. The second commissure tab 1196b of the second leaflet 1180b defines a third pass 1256b through the first slot 1134a (inside-out relative to the first commissure post 1120a) to define a second loop 1258b passing through the first slot 1134a. The first retaining element 1184b is positioned within the second loop 1258b to encircle the first retaining element 1184b and form a widened cross-section for the second loop 1258b on the outer side 1112 of the frame 1102. The width of the second loop 1258b is selected to resist, or be restrained from, pulling through the second slot 1136a. As shown, the first pass 1250b is positioned adjacent, and opposite the second pass 1252b, and adjacent the third pass 1256b with the third pass 1256b between the first pass 1250b and the second pass 1252b within the second slot 1136a.

The first loops 1254a,b, are optionally described as outer loops and the second loops 1258a,b are optionally described as inner loops. In some examples, one or more of the passes 1250a,b, 1252a,b, 1256a,b are coupled to one another (e.g., by molding, heat sealing/bonding, adhesives, sutures, or other means). Whether coupled or uncoupled (e.g., bonded or unbonded), the various passes can be inserted into the respective slots 1134a, 1136a with the first retaining elements 1184a, 1184b on the inner side 1110 of the frame 1102 and the second retaining elements 1186a, 1186b outer side of the frame 1102 by sliding the first commissure tab 1194a and the second commissure tab 1196b into the respective first slot 1134a and second slot 1136a through the first ends 1140a, 1144a (FIG. 13) of the first and second slots 1134a, 1136a, respectively. As shown, each of the first ends 1140a, 1144a are open ends. In some other examples, the first commissure tab 1194a and the second commissure tab 1194b are threaded through the slots 1134a, 1136a inside-out and outside-in to form the loops 1254a,b, 1258a,b (e.g., as opposed being slid upwardly into the slots 1134a, 1136a). Additionally, although three passes are shown for each of the commissure tabs in FIG. 18, fewer passes (two, where a single loop is desired) or more (e.g., where additional loops are desired) are contemplated.

As shown, the first leaflet 1180a and the second leaflet 1180b are spaced from one another at the inner side 1110 of the frame 1102, which can be described as the leaflets defining a commissure gap 1260 at the first commissure post

1120a. In some embodiments, the prosthetic valve 1100 defines a similar commissure gap 1260 between each of the circumferentially-adjacent leaflets 1180. In some examples, the commissure gap 1260 helps permit flow (e.g., both forward and backward flow) through the gap 1260, forming a small leak through the gap 1260. This localized flow region (available when valve closed, and also when the valve is open) helps prevent thrombus propagation adjacent the frame 1102, next to the commissure posts 1120, where there might otherwise be low, or stagnant flow.

FIGS. 19 and 20 shows the first retaining element 1184a and the second retaining element 1186a of the first leaflet 1180a received over the first hanging feature 1150a and in within the first channel 1154a (FIG. 13). The first retaining element 1184a and the second retaining element 1186a thus defines a hanging loop 1280a for supporting the first leaflet 1180a, and specifically the first commissure tab 1194a from the first commissure post 1120a. Also shown is the FIGS. 19 and 20 the first retaining element 1184b and the second retaining element 1186b of the second leaflet 1180b similarly received over the second hanging feature 1152a and in within the second channel 1156a (FIG. 13). The first retaining element 1184b and the second retaining element 1186b thus define a hanging loop 1280b for supporting the second leaflet 1180b, and specifically the second commissure tab 1196b from the first commissure post 1120a.

The remaining commissure tabs of the leaflets 1180 are secured to and supported from the remaining commissure posts 1120. Whereas the relatively smooth turns and reinforcement provided by the first and second retaining elements 1184, 1186 reduce stress concentrations at the commissure posts 1120 due to transverse loading of the leaflet construct 1104, the axial support provided the hanging loops, similar to hanging loops 1280a, 1280b provide axial support the leaflet construct 1104 and help to reduce axial stress concentrations at the attachment interfaces between the commissure posts 1120 and the leaflets 1180.

Figure 21:
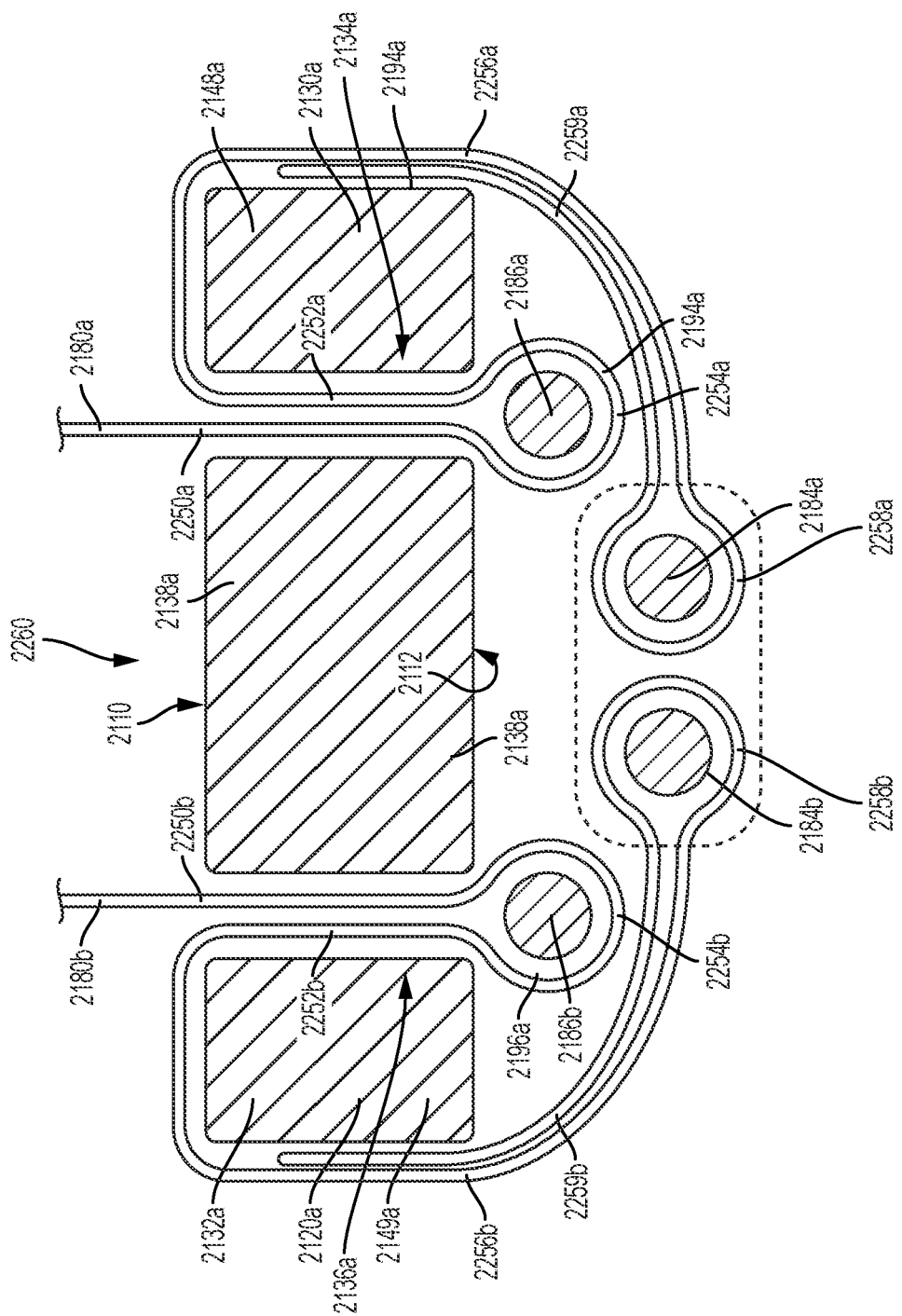
FIG. 21 shows another attachment arrangement between leaflets and a commissure post of a prosthetic valve, according to some embodiments.

FIG. 21 is illustrative of another leaflet attachment configuration between leaflets and commissure posts of a valve, such as the prosthetic valves 100, 1100, for example. FIG. 21 shows a first commissure post 2120a that includes the same features as the first commissure post 1120a unless otherwise indicated. As such, the description of the features and options of the first commissure post 1120a apply equally with respect to the first commissure post 2120a and operation and use of the first commissure post 2120a should be understood with reference to substitution or modification of the features of the prosthetic valve 100 or the prosthetic valve 1100.

As shown in FIG. 21, the first commissure post 2120a includes a first leg 2130a, a second leg 2132a, a first slot 2134a, which can also be described as a first post slot, and a second slot 2136a, which can also be described as a second post slot. The first slot 2134a and the second slot 2136a are each located between the first leg 2130a and the second leg 2132a. As shown, the first commissure post 2120a also includes an intermediate leg 2138a positioned between the first leg 2130a and the second leg 2132a. The first commissure post 2120a defines the first slot 2134a between the first leg 2130a and the intermediate leg 2138a and the second slot 2136a between the second leg 2132a and the intermediate leg 2138a. The first commissure post 2120a has an outer side corresponding to a frame outer side 2112 and a post inner side corresponding to a frame inner side 2110. The first commissure post 2120a further defines a first side 2148a, also described as a first lateral edge, and a second side 2149a, also described as a second lateral edge.

FIG. 21 shows a first leaflet 2180a that optionally includes the same features as the first leaflet 1180a unless otherwise indicated. As such, the description of the features and options of the first leaflet 1180a apply equally with respect to the first leaflet 2180a. As shown, the first leaflet 2180a includes a first commissure tab 2194a, a first retaining element 2184a and a second retaining element 2186a. The first retaining element 2184a and the second retaining element 2186a are optionally similar to the first retaining element 1184a and the second retaining element 1186a, with the first retaining element 2184a and the second retaining element 2186a being connected and continuous (e.g., contiguous) to define a loop (not shown) for hanging the first leaflet 2180a (e.g., from a hanging feature of the first commissure post 2120a similarly to the prosthetic valve 1100). Although the first retaining element 2184a and the second retaining element 2186a are optionally connected and define a loop for hanging, they are optionally separate as desired (e.g., similar to the first retaining element 1184a and the second retaining element 1186a of the first leaflet 1180a).

FIG. 21 shows a second leaflet 2180b that includes the same features as the second leaflet 1180b unless otherwise indicated. As such, the description of the features and options of the second leaflet 1180b apply equally with respect to the second leaflet 2180b. As shown, the second leaflet 2180b includes a second commissure tab 2196b, a first retaining element 2184b and a second retaining element 2186b. The first retaining element 2184b and the second retaining element 2186b are optionally similar to the first retaining element 1184b and the second retaining element 1186b, with the first retaining element 2184b and the second retaining element 2186b being connected and continuous (e.g., contiguous) to define a loop (not shown) for hanging the second leaflet 2180b. Although the first retaining element 2184b and the second retaining element 2186b are optionally connected and define a loop for hanging, they are optionally separate as desired (e.g., similar to the first retaining element 1184b and the second retaining element 1186b of the second leaflet 1180b).

As shown in FIG. 21, the first commissure tab 2194a of the first leaflet 2180a extends through the first slot 2134a a plurality of times (also described as a plurality of passes) and the second commissure tab 2196b of the second leaflet 2180b extends through the second slot 2136a of the first commissure post 2120a a plurality of times (also described as a plurality of passes), with the first retaining elements 2184a, 2184b positioned on the outer side 2112 of the frame 2102, and thus on the outer side of the first commissure post 2120a.

The second retaining elements 2186a, 2186b are also positioned on the outer side 2112 of the frame 2102, and thus the outer side of the first commissure post 2120a. As shown, the first retaining elements 2184a, 2184b secure the commissure tabs 2194a, 2196b, respectively, from being pulled outwardly relative to the frame 2102. In turn, the second retaining elements 2186a, 2186b secure the commissure tabs 2194a, 2196b, respectively, from being pulled inwardly relative to the frame 2102.

As shown, the first commissure tab 2194a of the first leaflet 2180a defines a first pass 2250a through the first slot 2134a (inside-out relative to the first commissure post 2120a) and a second pass 2252a through the first slot 2134a (outside-in relative to the first commissure post 2120a) to define a first loop 2254a through the first slot 2134a. The second retaining element 2186a is positioned within the first loop 2254a to encircle the second retaining element 2186a and form a widened cross-section for the first loop 2254a on the outer side 2112 of the frame 2102. The width of the first loop 2254a is selected to resist, or be restrained from, pulling through the first slot 2134a.

The first commissure tab 2194a of the first leaflet 2180a defines a third pass 2256a around the outside of the first commissure post 2120a, from the inner side 2110 around the first side 2148a to the outer side 2112 and then back from the outer side 2112 to the first side 2148a to define a fourth pass 2259a, the third and fourth passes 2256a, 2259a defining a second loop 2258a passing outside the commissure post 2120a on the first side 2148a. The first retaining element 2184a is positioned within the second loop 2258a to encircle the first retaining element 2184 and form a widened cross-section for the second loop 2258a on the outer side 2112 of the frame 2102. The width of the second loop 2258a is selected as desired (e.g., to fit against the outer side 2112 between the first leaflet 2180a and the second leaflet 2180b. As shown, the first pass 2250a is positioned adjacent, and opposite the second pass 2252a, and the third pass 2256a and fourth pass 2259a are positioned adjacent each other.

The second commissure tab 2196b defines a similar set of features to those of the first commissure tab 2194a, which are labeled on FIG. 21 for reference. As shown, the second commissure tab 2196b of the second leaflet 2180b defines a first pass 2250b through the second slot 2136a (inside-out relative to the first commissure post 2120a) and a second pass 2252b through the second slot 2136a (outside-in relative to the first commissure post 2120a) to define a first loop 2254b through the second slot 2136a. The second retaining element 2186b is positioned within the first loop 2254b to encircle the second retaining element 2186b and form a widened cross-section for the first loop 2254b on the outer side 2112 of the frame 2102. The width of the first loop 2254b is selected to resist, or be restrained from, pulling through the second slot 2136a.

The second commissure tab 2196b of the second leaflet 2180b defines a third pass 2256b around the outside of the first commissure post 2120a, from the inner side 2110 around the second side 2149a to the outer side 2112 and then back from the outer side 2112 to the second side 2149a to define a fourth pass 2259b, the third and fourth passes 2256b, 2259b defining a second loop 2258b passing outside the commissure post 2120a on the second side 2149a. The first retaining element 2184a is positioned within the second loop 2258a to encircle the first retaining element 2184a and form a widened cross-section for the second loop 2258b on the outer side 2112 of the frame 2102. The width of the second loop 2258b is selected as desired (e.g., to fit against the outer side 2112 between the first leaflet 2180a and the second leaflet 2180b).

As shown, the first retaining elements 2184a, 2184b, and thus the second loops 2258a, 2258b are secured together (e.g., with an adhesive or one or more fasteners, such as sutures or staples). In FIG. 21, a secondary coupler 2290 is shown in broken lines secured around the first retaining elements 2184a, 2184b. As shown, the secondary coupler 2290 is a filament, such as a suture or staple, for securing the first retaining elements 2184a, 2184b together. In other examples, the secondary coupler 2290 includes coating(s) or layer(s) of material over molded or otherwise disposed on the exterior and/or interior side of the frame 2102 to help couple the first loops 2254 and the second loops 2258 to one another and the frame 2102. For example, one or more layers of tape may be overwrapped onto first loops 2254 and/or second loops 2258, one or more jackets or covers of material may be placed over and secured to the first loops 2254 and/or second loops 2258, or other techniques may be employed. Generally, such materials may be selected not only to secure the first loops 2254 and the second loops 2258 in place, but may also be employed to form a continuous surface without cracks or other defects, which may help avoid tissue ingrowth and/or thrombus formation where such avoidance is desirable. Similarly, any of the other loop and post arrangements provided in this disclosure may be coupled with one or more secondary couplers (e.g., by one or more sutures, filaments, layers, and/or coatings). With the arrangement shown the second loops 2258a, 2258b can help prevent the first loops 2254a, 2254b from pulling outwardly (radial outward) from the commissure post 2120a.

The first loops 2254a,b, are optionally described as outer loops and the second loops 2258a,b are also optionally described as outer loops. In some examples, one or more of the passes 2250a,b, 2252a,b, 2256a,b, 2259a,b are coupled to one another (e.g., by molding, heat sealing, adhesives, sutures, or other means). Whether coupled or uncoupled (e.g., bonded or unbonded), the passes can be inserted into the first slot 2134a and second slot 2136a, respectively, with the first retaining elements 2184a,b on the outer side 2112 of the frame 2102 and the second retaining elements 2186a,b outer side of the frame 2102 by sliding the first and second commissure tabs 2194a, 2196b into the first slot 2134a and the second slot 2136a through open ends of the slots (not shown, but see the first commissure post 2120a for an example).

In some other examples, the first and second commissure tabs 1194a, 1194b are threaded through the slots 2134a, 2136a and around the sides 2148a, 2149a (e.g., rather than being slid up into the slots 2134a, 2136a and around the first and second legs 2130a, 2132a. Although the described number of passes are shown for each of the commissure tabs in FIG. 21, fewer or greater passes are also contemplated.

With the arrangement shown in FIG. 21, none of the first retaining elements 2184, second retaining elements 2186, first loops 2254, or second loops 2258 resides on the inner side 2110 of the frame 2102. Thus, those features are outside of the flow field and do not interfere with blood flow through the prosthetic valve 1100. Although relatively sharp corners are shown in FIG. 21 at the first and second slots 2134a, 2136a of the first commissure post 2120a, it should be understood that chamfers, rounds, reliefs coatings and other features may be provided to avoid stress concentrations or other wearing of the first and second leaflets 2180a, 2180b at those slot edges.

As shown, the first leaflet 2180a and the second leaflet 2180b are spaced from one another at the inner side 2110 of the frame 2102, which can be described as the leaflets defining a commissure gap 2260 at the commissure post 2120a. In some embodiments, the prosthetic valve (e.g., prosthetic valve 1100) defines similar commissure gaps between each, circumferentially-adjacent leaflets of the prosthetic valve.

Figure 22:
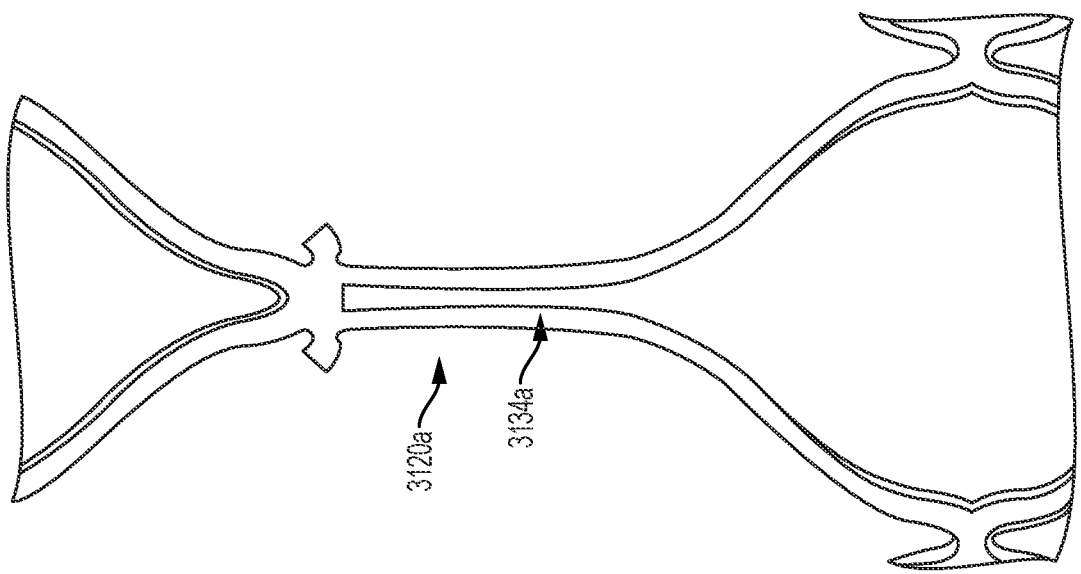

FIG. 22 shows another, first commissure post 3120a for a prosthetic valve, such as the prosthetic valve 100 or prosthetic valve 1100. As shown, the first commissure post 3120a is substantially similar to the first commissure post 1120a, although the first commissure post 3120a forms a single slot 3134a (as opposed to two slots as with the first commissure post 1120a. FIG. 23 shows an example of first leaflet 3180a and the second leaflets 3180b secured to the first commissure post 3120a similarly to the first commissure post 1120a, although the first commissure tab 3194a and the second commissure tab 3196b are secured in the single slot 3134a, rather than two slots as with the first commissure post 1120*a* of the prosthetic valve 1100. That is, the design of the first commissure post 3120*a* and attachment arrangement are optionally employed for the prosthetic valve 1100 for one or more of the commissure posts 1120 as desired. Again, although relatively sharp corners are shown, it should be understood that chamfers, rounds, reliefs coatings and other features may be provided to avoid stress concentrations or other wearing of the leaflets 3180*a*, 3180*b* at the slot edges.

Figure 25:
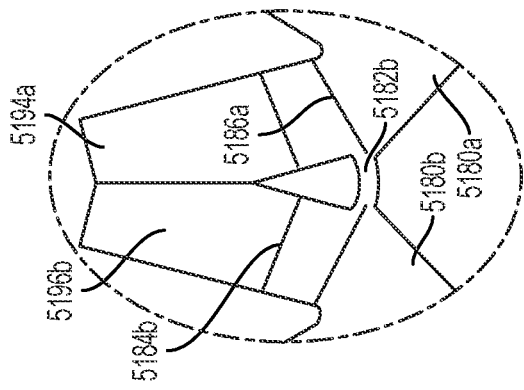
Figure 26:
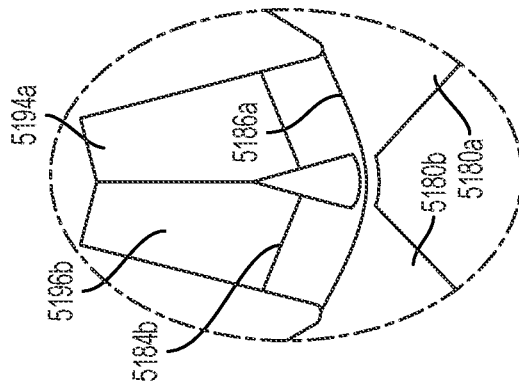
Figure 27:
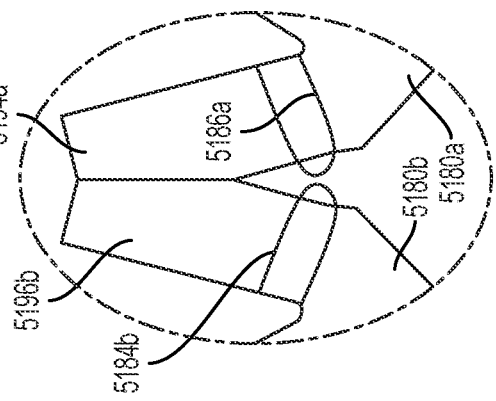
Figure 28:
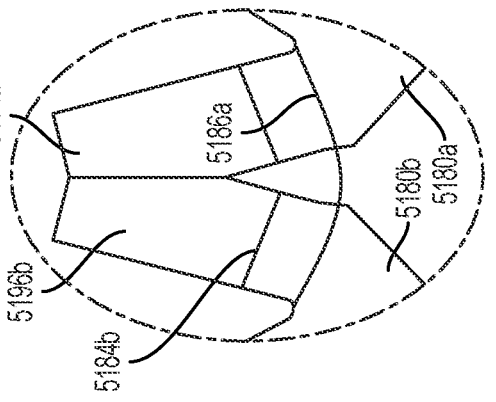

FIGS. 24-28 show various alternative arrangements of first retaining elements 5184 and second retaining elements 5186 on first commissure tabs 5194 and second commissure tabs 5196 of leaflets 5180. As previously mentioned, the suffix "a" generally denotes a first one of the leaflets 5180*a* and "b" a second one of the leaflets 5180*b*. FIG. 24 illustrates a similar arrangement as that of the prosthetic valve 100. FIG. 25 illustrates a similar arrangement as that of the prosthetic valve 100, with the second retaining element 5186 being separate and a bridge 5182 extending between the leaflets 5180. FIG. 26 is similar to FIG. 25, but without a bridge. FIG. 27 shows a similar arrangement as FIG. 24, but without a bridge. Finally, FIG. 28 shows an arrangement without a bridge and with first retaining elements and second retaining elements that are looped, or interconnected on each of the respective commissure tabs 5194, 5196. It should be understood that any of the foregoing arrangements are contemplated and can be employed as appropriate to achieve loop configurations for securing leaflets to commissure posts as described above.

Figure 30:
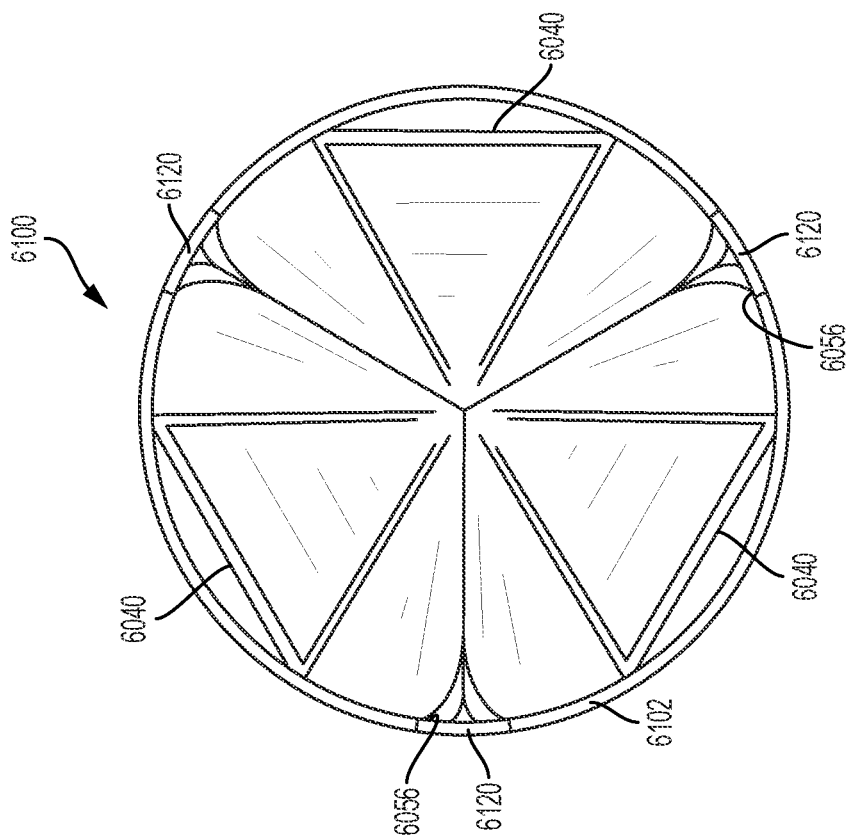
FIGS. 29 to 31 show a potential modification for commissure attachment regions of the prosthetic valve of FIG. 11, according to some embodiments.
Figure 29:
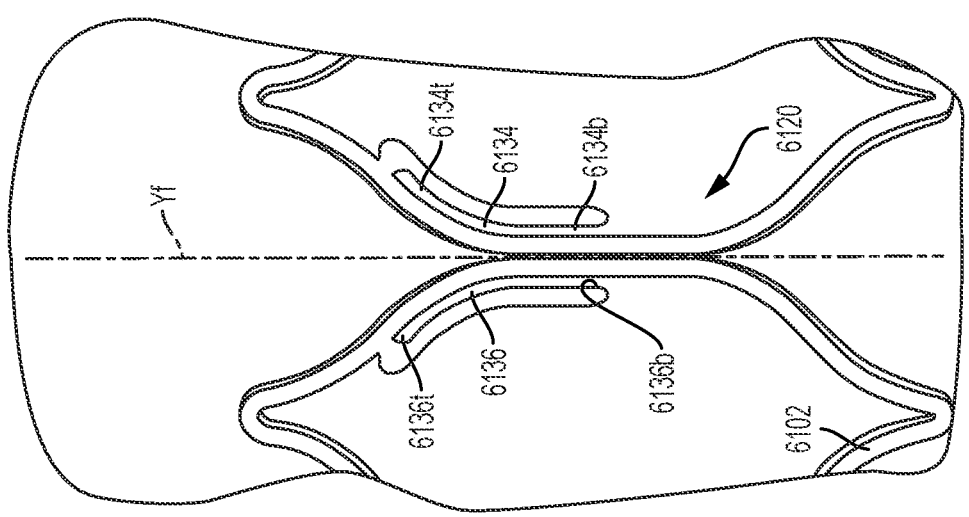

Prosthetic valve leaflets detaching from a support structure, or frame, constitute a high risk to a patient into which it is placed. One factor contributing to leaflet detachment can be peak stress in the leaflet at the commissure region when the prosthetic valve is closed and under fluid backpressure. FIGS. 29 and 30 show a commissure attachment region variation and associated leaflet closing profile at the outflow end that can be employed in any of the embodiments and examples previously described. Adjacent, diverging leaflet attachment regions, may provide beneficial overall stress profiles in the leaflet adjacent the commissure regions of the leaflets.

As shown in FIG. 29, the commissure attachment regions 6034, 6036 (which may correspond to a modified version of the slots 1134, 1136 of FIG. 13 or the slots 2134, 2136 of FIG. 21) of commissure post 6120 (which may correspond to commissure posts 1120 or 2120) are modified to provide means by which to preserve, if not shorten, prosthetic valve height while reducing the peak commissure stress in the leaflet at the commissure post without altering the leaflet material properties.

FIG. 30 shows a prosthetic valve 6100, which may be substantially the same as the prosthetic valve 1100, apart from the diverging commissure attachment region modification. As shown, the prosthetic valve 6100 includes a frame 6102 (designated generally in FIG. 30) including a plurality of the commissure posts 6120 configured similarly to the example of FIG. 29. The prosthetic valve 6100 also includes a plurality of leaflets 6040 coupled to and supported by the frame 6102.

As shown in FIG. 29, the upper most portion of adjacent commissure attachment regions 6134, 6136 (e.g., the slots 1134, 1136 or the slots 2134, 2136) on the frame (e.g., the frame 1102 or 2102) have been modified from being non-divergent (e.g., parallel as shown in FIGS. 1, 11A, and 22) to being divergent. For example, the adjacent commissure attachment regions 6134, 6136 of each commissure post 6120 optionally terminate by extending away from a middle axis Yf positioned centrally between each of the adjacent commissure attachment regions 6134, 6136, the pair diverging from a location below the commissure post tip in the outflow direction. The adjacent commissure attachment regions 6134, 6136 may diverge along their entire heights, or may have a base portion 6134*b*, 6136*b* that is parallel or otherwise non-diverging and a terminal portion 6134*t*, 6136*t* that is diverging as shown in FIG. 29.

Figure 31:
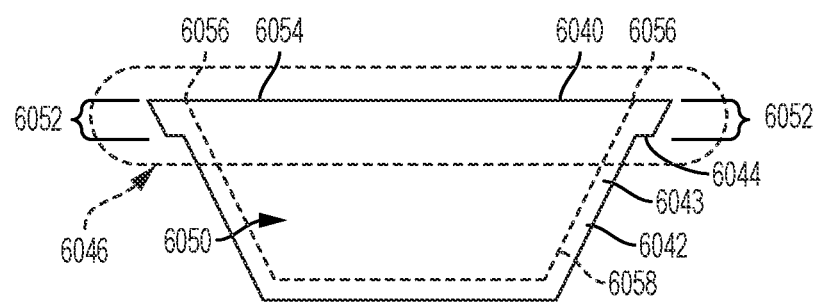

FIG. 31 is a schematic view of one of the plurality of leaflets 6040 (e.g., which may correspond to one of the plurality of leaflets 1180 or one of the plurality of leaflets 2180) having a cusp 6050, a free edge 6054, and commissure regions 6052. The free edge 6054 extends to two termini 6056. The two termini 6056 are defined at an intersection of the leaflet free edge 6054 and the leaflet attachment region 6043. The leaflet attachment regions 6043 of adjacent leaflets 6040 are configured to be coupled to the commissure posts 6120 at locations on the adjacent leaflets 6040 that are adjacent the termini 6056 of the adjacent leaflets 6040.

As illustrated schematically in FIG. 31, a (dashed) fold line 6058 defines an outer margin 6042 of the cusp 6050 and commissure regions 6052 used to secure the leaflet 6040 to the frame 6102 (e.g., frame 1102 or frame 2102). A free edge region 6046 is that location of the leaflet 6040 including and adjacent to the leaflet free edge 6054. The outer margin 6042 of each leaflet 6040 is coupled to the frame 6102, and the free edge 6054 of the leaflet 6040 extends across a cylindrical region defined by the frame 6102. In terms of the first leaflet 1180*a* (FIG. 15) of the plurality of leaflets 1180, the cusp 6050 of FIG. 31 corresponds to the body portion 1190*a* and the outer margin 6042 corresponds to the fold over portion 1198*a*, with the free edge 6054 corresponding to the free edge 1206*a* (FIG. 15). The same features of the leaflets 2180 similarly correspond to those of the leaflet 6040. As previously described in association with the leaflets 1180, 2180, the outer margin 6042 (the fold over portions) are used to secure the leaflet 6040 onto a frame, such as the frame 1102 or frame 2102.

In various examples, the commissure regions 6052 of adjacent ones of the leaflets 6040 are operable to pass through the adjacent commissure attachment regions 6134, 6136 (e.g., slots) in a side-by-side relationship. The commissure regions 6052 of adjacent leaflets 6040 are coupled to the frame 6020 at the diverging commissure attachment regions 6134, 6136. Because the commissure post 6120 defines diverging commissure attachment regions 6134, 6136 that diverge in the outflow direction towards the commissure post tip the commissure regions 6052 of adjacent, respective leaflets 6040 will also diverge from a location away from the commissure post tip in the outflow direction when adjacent leaflets are in a closed, coapted position.

Non-diverging commissure attachment regions (e.g., such as those shown in FIGS. 11 and 22) may have a maximal stress at the region corresponding to the terminus 6056 when a leaflet is in the closed position. It turn, use of diverging commissure attachment regions (e.g., as shown in FIGS. 29 and 30), may help translate the region of maximal stress away from the termini 6056 of adjacent leaflets 6040, to be distributed over a larger area, and to also have a reduced magnitude. For example, stress force vectors within the leaflets 6040 along diverging regions proximate the termini 6056 may be reduced relative to the same basic frame and leaflet arrangement but with non-diverging commissure attachment regions by a reduction of 41% of peak stress in the leaflets 6040 in the free edges 6054 at the termini 6056 for a given frame length. The stress within the leaflets 6040 along the diverging region (e.g., in the free edges 6054 at the termini 6056) may be reduced more than 40% relative to a non-diverging attachment when exposed to peak closing pressures of about 135 mmHg for a given support structure length. It has been demonstrated that the location of maximum loaded stress can be moved to a predetermined and more favorable location and the magnitude and distribution of stress that a given region of the leaflet 6040 experiences can be changed by changing the geometry of the support attachment region (i.e., by using diverging attachment regions for adjacent leaflets), and similar results are expected by modifying the divergence and curvature of the slots 1134, 1136 and slots 2134, 2136 similar to that of the leaflet attachment regions 6134, 6136, for example.

Although some examples have been provided, it should be understood that similar diverging attachment regions may be implemented with cut tube, wire frame, or any other type of frame (or frame material) as desired to achieve reduced, and more distributed stresses from the leaflet termini. The attachment configurations described above can be particularly advantageous when employed with polymeric (e.g., ePTFE-based) leaflets, although any of a variety of leaflet materials are contemplated.

Leaflet Materials

In various examples, any of the leaflet constructs described herein (e.g., leaflet construct 104 or 1104) may be formed of a biocompatible, synthetic material (e.g., including ePTFE and ePTFE composites, or other materials as desired). Other biocompatible polymers which can be suitable for use in synthetic leaflets include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

In other examples, such leaflet construct is formed of a natural material, such as repurposed tissue, including bovine tissue, porcine tissue, or the like.

As used herein, the term "elastomer" refers to a polymer or a mixture of polymers that has the ability to be stretched to at least 1.3 times its original length and to retract rapidly to approximately its original length when released. The term "elastomeric material" refers to a polymer or a mixture of polymers that displays stretch and recovery properties similar to an elastomer, although not necessarily to the same degree of stretch and/or recovery. The term "non-elastomeric material" refers to a polymer or a mixture of polymers that displays stretch and recovery properties not similar to either an elastomer or elastomeric material, that is, considered not an elastomer or elastomeric material.

In accordance with some embodiments herein, the leaflet construct comprises a composite material having at least one porous synthetic polymer membrane layer having a plurality of pores and/or spaces and an elastomer and/or an elastomeric material and/or a non-elastomeric material filling the pores and/or spaces of the at least one synthetic polymer membrane layer. In accordance with other examples, the leaflet construct further comprises a layer of an elastomer and/or an elastomeric material and/or a non-elastomeric material on the composite material. In accordance with some examples, the composite material comprises porous synthetic polymer membrane by weight in a range of about 10% to 90%

An example of a porous synthetic polymer membrane includes expanded fluoropolymer membrane having a node and fibril structure defining the pores and/or spaces. In some examples, the expanded fluoropolymer membrane is expanded polytetrafluoroethylene (ePTFE) membrane. Another example of porous synthetic polymer membrane includes microporous polyethylene membrane.

Examples of an elastomer and/or an elastomeric material and/or a non-elastomeric material include, but are not limited to, copolymers of tetrafluoroethylene and perfluoromethyl vinyl ether (TFE/PMVE copolymer), (per)fluoroalkyl-vinylethers (PAVE), urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing. In some examples, the TFE/PMVE copolymer is an elastomer comprising essentially of between 60 and 20 weight percent tetrafluoroethylene and respectively between 40 and 80 weight percent perfluoromethyl vinyl ether. In some examples, the TFE/PMVE copolymer is an elastomeric material comprising essentially of between 67 and 61 weight percent tetrafluoroethylene and respectively between 33 and 39 weight percent perfluoromethyl vinyl ether. In some examples, the TFE/PMVE copolymer is a non-elastomeric material comprising essentially of between 73 and 68 weight percent tetrafluoroethylene and respectively between 27 and 32 weight percent perfluoromethyl vinyl ether. The TFE and PMVE components of the TFE-PMVE copolymer are presented in wt %. For reference, the wt % of PMVE of 40, 33-39, and 27-32 corresponds to a mol % of 29, 23-28, and 18-22, respectively.

In some examples, the TFE-PMVE copolymer exhibits elastomer, elastomeric, and/or non-elastomeric properties.

In some examples, the composite material further comprises a layer or coating of TFE-PMVE copolymer comprising from about 73 to about 68 weight percent tetrafluoroethylene and respectively from about 27 to about 32 weight percent perfluoromethyl vinyl ether.

In some examples, the leaflet construct is an expanded polytetrafluoroethylene (ePTFE) membrane having been imbibed with TFE-PMVE copolymer comprising from about 60 to about 20 weight percent tetrafluoroethylene and respectively from about 40 to about 80 weight percent perfluoromethyl vinyl ether, the leaflet construct further including a coating of TFE-PMVE copolymer comprising from about 73 to about 68 weight percent tetrafluoroethylene and respectively about 27 to about 32 weight percent perfluoromethyl vinyl ether on the blood-contacting surfaces.

As discussed above, the elastomer and/or an elastomeric material and/or a non-elastomeric material may be combined with the expanded fluoropolymer membrane such that the elastomer and/or the elastomeric material and/or the non-elastomeric material occupies substantially all of the void space or pores within the expanded fluoropolymer membrane.

In accordance with an embodiment, the composite material can include an expanded fluoropolymer material made from porous ePTFE membrane, for instance as generally described in U.S. Pat. No. 7,306,729 to Bacino.

The expanded fluoropolymer membrane, used to form some of the composites described, can comprise PTFE homopolymer. In alternative embodiments, blends of PTFE, expandable modified PTFE and/or expanded copolymers of PTFE can be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

Frame Materials

The various frames can be etched, cut, laser cut, stamped, three-dimensional printed or wire wound, among other suitable processes. The frames can be self-expanding or balloon expandable (e.g., when configured for transcatheter implantation) or non-expandable (e.g., when configured for surgical implantation). The various frames can comprise materials, such as, but not limited to, any metallic or polymeric material, such as an elastically (e.g., nitinol) or plastically (e.g., stainless steel) deformable metallic or polymeric material that is generally biocompatible. Other materials suitable for any of the frames described herein include, but are not limited to, other titanium alloys, stainless steel, cobalt-nickel alloy, polypropylene, acetyl homopolymer, acetyl copolymer, a drawn filled tube (e.g., nitinol wire with a platinum core), other alloys or polymers, or any other material that is generally biocompatible having adequate physical and mechanical properties to function as a frame as described herein.

Methods of Making

Various methods of making prosthetic valves are contemplated for the various prosthetic valves described herein. Generally, the methods include providing a frame and a leaflet construct according to any of the above-described embodiments and securing the leaflet construct to the frame.

In some methods, the leaflet construct is at least partially coupled to the frame by a looped structure. For example, in some methods part of the leaflet construct (e.g., the bridge and/or the retaining element) is secured over the hanging element of the frame to axially support the leaflet construct from the hanging element. Additionally or alternatively, the commissure tabs of the leaflet construct define one or more loops that are passed through slots in the commissure posts of the frames, such as the commissure posts according to any of the frame embodiments previously described. In some examples, inner retaining elements pass through one or more of the loops to help widen the loops and help prevent the loop(s), or passes of material, from pulling outwardly through the slots in the commissure posts. Outer retaining elements additionally or alternatively help prevent the loop(s), or passes of material, from pulling inwardly through the slots in the commissure posts. In various examples, the loop(s) of material are optionally coupled to one another and/or to the frame (e.g., bonded, over molded, coated, adhered by an outer wrap of film, sutured, and/or otherwise secured) to help secure the commissure tabs to the commissure posts. The body portions of the leaflets are optionally attached to the frame using attachment tabs secured through and folded over the outer side of the frame and/or attachment element.

Transcatheter Delivery System

Figure 32:
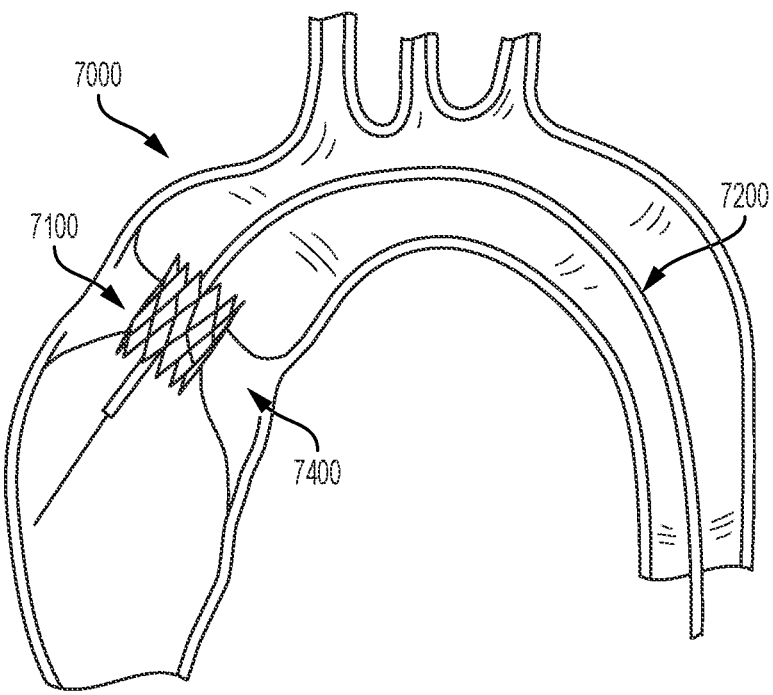
FIGS. 32 and 33 show methods of implanting a prosthetic valve, according to some embodiments.

In some embodiments, with reference to FIG. 32, a prosthetic valve delivery system 7000 comprises a prosthetic valve 7100 (such as any of the prosthetic valves previously described) configured as a transcatheter prosthetic valve having a collapsed configuration and an expanded configuration and an elongated flexible catheter 7200, such as a balloon catheter, configured to deploy the prosthetic valve 7100 via catheter. The catheter 7200 can comprise a balloon to expand the prosthetic valve 7100 and/or if required, to touch up the prosthetic valve 7100 to ensure proper seating. The prosthetic valve 7100 can be mounted to the distal section of the catheter 7200 for delivery through the vasculature. In order to hold the prosthetic valve 7100 in a collapsed configuration on the catheter 6200, the prosthetic valve delivery system 7000 may further comprise a removable sheath (not shown) to closely fit over the transcatheter prosthetic valve 7100.

Some methods of delivery include the steps of radially compressing a prosthetic valve (such as any of the prosthetic valves previously described) into its collapsed configuration onto the distal end of an elongate flexible catheter having proximal and distal ends; delivering the prosthetic valve to a tissue orifice, such as a native aortic valve orifice 7400, via a transfemoral or transapical route, and expanding the prosthetic valve into the tissue orifice 7400. The prosthetic valve can be expanded by inflating a balloon or can be self-expanding, for example.

Some methods of delivery include the steps of radially compressing a prosthetic valve (such as any of the prosthetic valves previously described) into its collapsed configuration, onto the distal section of an elongated flexible catheter having proximal and distal ends. A restraint, which can be connected to a tether that passes through the orifice of prosthetic valve and the lumen of the catheter, is fitted around the posts of the prosthetic valve. The prosthetic valve is then delivered to a native valve orifice, such as a native aortic valve orifice, via a route of delivery and expanded into the native orifice. The route of delivery can comprise a transfemoral or transapical route, for example. The prosthetic valve can be expanded by inflating a balloon or can be self-expanding, for example.

Surgical Embodiments

Figure 33:
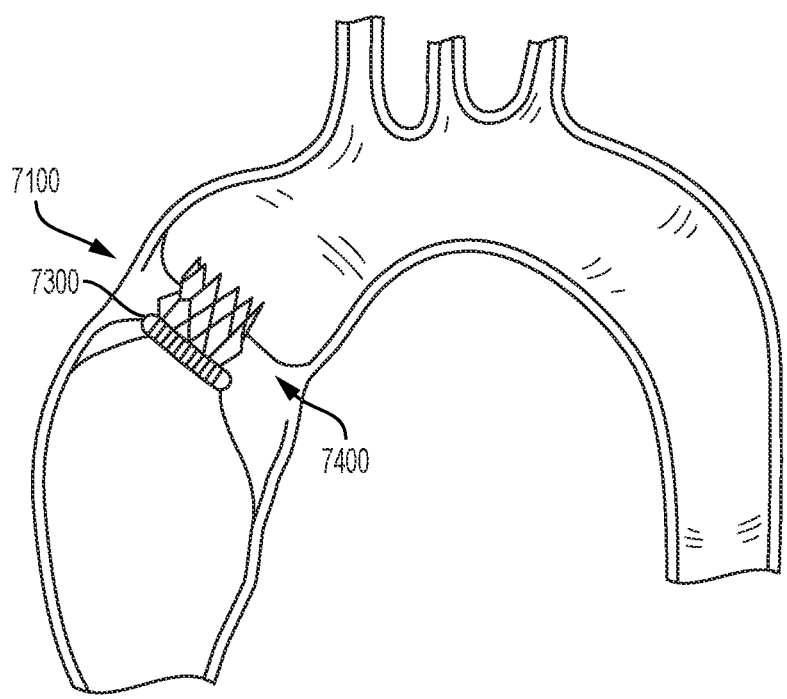

It is appreciated that any of the prosthetic valves previously described may be surgically implanted rather than using transcatheter techniques. As shown in FIG. 33, a surgically implanted prosthetic valve 7100 (such as any of the prosthetic valves previously described) may be substantially the same as those described above, with the addition of a sewing cuff 7300 adjacent to the frame outer side. The sewing cuff 7300, which is well known in the art, is operable to provide structure that receives suture for coupling the prosthetic valve 7100 to an implant site, such as the tissue orifice 7400. The sewing cuff may comprise any suitable material, such as, but not limited to, double velour polyester. The sewing cuff may be located circumferentially around the frame of the prosthetic valve 7100 or perivalvular depending from the frame of the prosthetic valve 7100.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A prosthetic valve comprising:
   a leaflet construct including a first leaflet;
   a first retaining element coupled to the first leaflet;
   a second retaining element coupled to the first leaflet; and
   a frame having an inlet end, an outlet end, and a central longitudinal axis extending from the inlet end to the outlet end, and a slot operable to receive a portion of the first leaflet therethrough such that the first leaflet defines a first outer loop portion on an outer side of the frame and a first inner loop portion on an inner side of the frame, wherein a portion of the first retaining element is received within the first outer loop portion and wherein a portion of the second retaining element is received within the first inner loop portion;

wherein the first outer loop portion encircles the portion of the first retaining element, and the first inner loop portion encircles the portion of the second retaining element; and wherein the portion of the first retaining element extends along a first single axis in a direction parallel to the central longitudinal axis from an upper end of the first outer loop portion to a lower end of the first outer loop portion entirely within the first outer loop portion, and wherein the portion of the second retaining element extends along a second single axis in a direction parallel to the central longitudinal axis from an upper end of the first inner loop portion to a lower end of the first inner loop portion entirely within the first inner loop portion.

2. The prosthetic valve of claim 1, wherein the frame further includes a projection over which the first retaining element is received to axially support the leaflet construct.

3. The prosthetic valve of claim 2, wherein the leaflet construct includes a second leaflet and a bridge interconnecting the first and the second leaflets, wherein the bridge hangs over the projection.

4. The prosthetic valve of claim 1, wherein the first leaflet includes a body portion, a first tab portion extending from a first side of the body portion to a terminal end, and a second tab portion extending from a second side of the body portion to a terminal end, the first tab portion forming the first inner loop portion and the first outer loop portion and the terminal end of the first tab portion is positioned outside side of the frame.

5. The prosthetic valve of claim 1, wherein the slot is a closed slot or where the slot extends from an open end to a closed end.

6. The prosthetic valve of claim 1, wherein the slot is formed through the frame in a radial direction relative to the central longitudinal axis of the frame or the slot is formed at an angle to a radial direction relative to the central longitudinal axis of the frame.

7. The prosthetic valve of claim 1, wherein tension on the first leaflet reduces a width of the slot.

8. The prosthetic valve of claim 1, wherein a cross-sectional area of the first retaining element and the first outer loop portion is greater than a width of the slot.

9. The prosthetic valve of claim 1, wherein the first leaflet defines a plurality of attachment tabs around a perimeter of the first leaflet that extend over the frame and coupled to the outer side of the frame.

10. The prosthetic valve of claim 9, wherein each of the attachment tabs is separated from an adjacent attachment tab by an opening for receiving a portion of the frame and optionally wherein the attachment tabs of the first leaflet each include a plurality of apertures.

11. The prosthetic valve of claim 1, wherein the frame defines a plurality of commissure posts each including a first post leg and a second post leg that are spaced to define the slot.

12. The prosthetic valve of claim 11, wherein the leaflet construct includes a plurality of leaflets interconnected with one another by a plurality of bridges that pass through the slots of the commissure posts.

13. The prosthetic valve of claim 1, wherein the frame includes a plurality of frame elements that define a plurality of leaflet attachment regions each having a shape of an isosceles trapezoid having two leaflet attachment region sides diverging from a leaflet base.

14. The prosthetic valve of claim 13, wherein the leaflet base is perpendicular to the frame central longitudinal axis.

15. The prosthetic valve of claim 1, wherein the leaflet construct comprises at least one expanded fluoropolymer membrane layer.

16. The prosthetic valve of claim 15, wherein a second material is contained within a porous structure of the expanded fluoropolymer membrane layer, coated on one or both sides of the expanded fluoropolymer membrane layer, or a combination of coated on and contained within the expanded fluoropolymer membrane layer.

17. The prosthetic valve of claim 1, wherein the leaflet construct comprises a composite having more than one fluoropolymer membrane layer.

18. The prosthetic valve of claim 1, wherein the frame comprises a shape memory metal, stainless steel, and/or a nickel-titanium alloy.

19. The prosthetic valve of claim 1, wherein the leaflet construct comprises a fluoropolymer membrane layer including ePTFE.

20. The prosthetic valve of claim 1, wherein the leaflet construct defines a continuous annular ring.

21. The prosthetic valve of claim 1, wherein the first leaflet has a first tab portion and a second tab portion and the leaflet construct includes a second leaflet with a first tab portion and a second tab portion;

wherein the first tab portion of the first leaflet defines a first pass, a second pass, and a third pass through the slot, the first pass and the second pass of the first tab portion of the first leaflet forming the first outer loop portion and the second pass and third pass of the first tab portion of the first leaflet forming the first inner loop portion;

wherein the second tab portion of the second leaflet defines a first pass, a second pass, and a third pass through the slot, the first pass and the second pass of the second tab portion of the second leaflet forming a second outer loop portion and the second pass and third pass of the second tab portion of the second leaflet forming a second inner loop portion; and wherein the first outer loop portion and the second outer loop portion are arranged adjacent to each other on the outer side of the frame and the first inner loop portion and the second inner loop portion are arranged adjacent to each other on the inner side of the frame.

22. The prosthetic valve of claim 21, wherein the portion of the first retaining element encircled by the first outer loop portion comprises a first portion, and the first retaining element comprises a second portion that extends through the second outer loop portion.

23. A prosthetic valve comprising:

a leaflet construct including a first leaflet having a body portion, a first tab portion extending from the body portion, and a second tab portion extending from the body portion opposite to the first tab portion, wherein the body portion, the first tab portion and the second tab portion are formed from a single, continuous piece of material;

a first retaining element coupled to the first leaflet; and a frame having a central longitudinal axis and a slot through which the first tab portion extends multiple times, including a first pass, a second pass, and a third pass through the slot.

24. The prosthetic valve of claim 23, wherein the first pass and the third pass are coupled and positioned adjacent to one other.

25. The prosthetic valve of claim 23, wherein the first pass is adjacent the second pass which is adjacent the third pass.

26. The prosthetic valve of claim 23, wherein the first, second, and third passes are coupled to each other.

27. The prosthetic valve of claim 23, wherein the second pass and the third pass of the first tab portion form a first inner loop portion adjacent an inner side of the frame and that is restrained from pulling through the slot.

28. The prosthetic valve of claim 27, wherein the first pass and the second pass of the first tab portion form a first outer loop portion adjacent an outer side of the frame and that is restrained from pulling through the slot.

29. The prosthetic valve of claim 28, wherein the first retaining element extends along a first single axis through the first outer loop portion in a direction parallel to the central longitudinal axis of the frame such that the first outer loop portion extends around the first retaining element along an entire length of the first outer loop portion between an upper end of the first outer loop portion and a lower end of the first outer loop portion.

30. The prosthetic valve of claim 29, wherein the first retaining element is coupled to the first outer loop portion.

31. The prosthetic valve of claim 28, wherein a second retaining element extends along a second single axis through the first inner loop portion in a direction parallel to the central longitudinal axis of the frame such that the first inner loop portion extends around the second retaining element along an entire length the first inner loop portion between an upper end of the first inner loop portion and a lower end of the first inner loop portion.

32. The prosthetic valve of claim 31, wherein the second retaining element is coupled to the first inner loop portion.

33. The prosthetic valve of claim 23, wherein the first tab portion forms a first loop, and the leaflet construct further includes a second leaflet having a second tab portion defining a second loop, and further wherein the first retaining element extends into the first loop of the first leaflet and into the second loop of the second leaflet.

* * * * *